(12) United States Patent
Duijsens et al.

(10) Patent No.: US 9,555,234 B2
(45) Date of Patent: Jan. 31, 2017

(54) IMPLANTABLE MEDICAL LEADS

(71) Applicant: Medtronic, Inc., Minneapolis, MN (US)

(72) Inventors: Victor Duijsens, Grevenbicht (NL); Paulus C. van Venrooij, Hoensbroek (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/396,239

(22) PCT Filed: Feb. 14, 2013

(86) PCT No.: PCT/US2013/026141
§ 371 (c)(1),
(2) Date: Oct. 22, 2014

(87) PCT Pub. No.: WO2014/018092
PCT Pub. Date: Jan. 30, 2014

(65) Prior Publication Data
US 2015/0142090 A1    May 21, 2015

Related U.S. Application Data

(60) Provisional application No. 61/676,073, filed on Jul. 26, 2012, provisional application No. 61/676,067, (Continued)

(51) Int. Cl.
*A61N 1/08* (2006.01)
*A61N 1/05* (2006.01)
(Continued)

(52) U.S. Cl.
CPC .............. *A61N 1/0534* (2013.01); *A61N 1/05* (2013.01); *A61N 1/36182* (2013.01); *H05K 3/32* (2013.01);
(Continued)

(58) Field of Classification Search
USPC ............................................. 607/59, 116, 60
See application file for complete search history.

(56) References Cited

U.S. PATENT DOCUMENTS 8,046,909 B2  11/2011  Dye et al.
8,225,504 B2   7/2012  Dye et al.
(Continued)

FOREIGN PATENT DOCUMENTS

WO   2006069322 A2   6/2006
WO   2011028809 A1   3/2011
WO   2012039919 A2   3/2012

OTHER PUBLICATIONS

U.S. Appl. No. 61/676,060, filed Jul. 26, 2012 by Venrooij.
(Continued)

*Primary Examiner* — Carl H Layno
*Assistant Examiner* — Jon Eric C Morales
(74) *Attorney, Agent, or Firm* — Shumaker & Sieffert, P.A.

(57) ABSTRACT

An assembly for a medical lead includes an elongated lead body, and a conductive element located at a distal portion of the lead body. The conductive element substantial!)' encircles a longitudinal axis of the lead body. The assembly further includes a plurality of insulated conductors extending within the lead body, each of the insulated conductors being in electrical contact with the conductive element and extending to a proximal end of the lead body. Each of the insulated conductors contacts a different circumferential portion of the conductive element. The conductive element is configured to facilitate mechanical and electrical separation of different circumferential portions of the conductive element to form two or more electrode segments for the medical lead from the conductive element.

19 Claims, 26 Drawing Sheets

Related U.S. Application Data filed on Jul. 26, 2012, provisional application No. 61/676,060, filed on Jul. 26, 2012.

(51) Int. Cl.
 *A61N 1/36* (2006.01)
 *H05K 3/32* (2006.01)
(52) U.S. Cl.
 CPC ..... *Y10T 29/49155* (2015.01); *Y10T 29/49158* (2015.01)

(56) References Cited

U.S. PATENT DOCUMENTS

2008/0269854 A1 10/2008 Hegland et al.
2012/0071949 A1* 3/2012 Pianca et al. ............... 607/59

OTHER PUBLICATIONS

U.S. Appl. No. 61/676,067, filed Jul. 26, 2012 by Venrooij.
International Search Report and Written Opinion from International Application No. PCT/US2013/026141, dated Aug. 13, 2013, 16 pp.

* cited by examiner

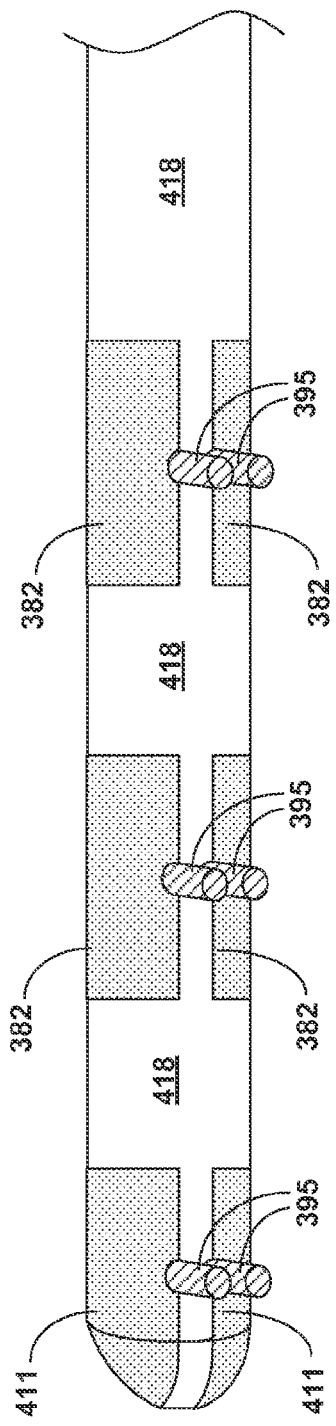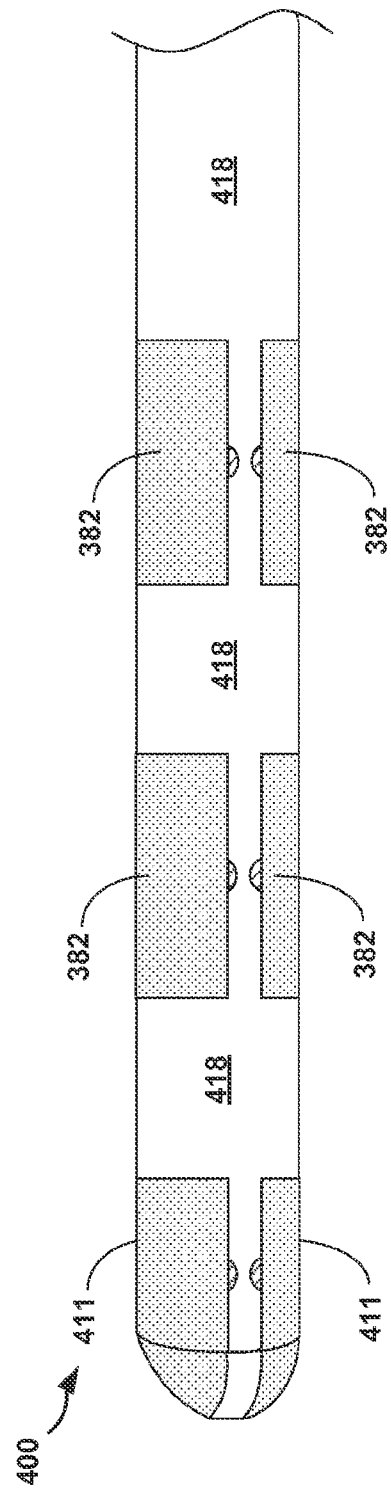

IMPLANTABLE MEDICAL LEADS

TECHNICAL FIELD

The present disclosure relates to medical devices and, more particularly, to medical leads configured for delivering electrical stimulation therapy and/or sensing electrical physiological signals.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target tissues of the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

Implantable medical leads carry electrodes that may be used to deliver electrical stimulation and/or sense electrical physiological signals. Different examples of implantable medical leads include cylindrical leads carrying ring electrodes or segmented electrodes and paddle style leads that carry electrode contacts. Paddle style leads may provide directional stimulation, but often require surgical implantation, although percutaneous implantation is possible. Cylindrical leads with ring or segmented electrodes may be implanted surgically or percutaneously. Ring electrodes may provide a less focused stimulation field that extends radially from the lead in many directions. Segmented electrodes may provide directional stimulation.

SUMMARY

This disclosure includes techniques for the design, manufacture and use of implantable medical leads including electrode segments in a circular or ring arrangement. Medical leads including electrode segments as described herein may be percutaneously implantable while providing directional stimulation and or sensing functionality.

In one example, this disclosure is directed to a method of manufacturing a medical lead comprising removing material from a conductive element to form two or more electrode segments from the conductive element. The conductive element is part of an assembly, the assembly comprising an elongated lead body and the conductive element. The conductive element is located at a distal portion of the lead body. The conductive element substantially encircles a longitudinal axis of the lead body. The assembly further comprises a plurality of insulated conductors extending within the lead body, each of the insulated conductors being in electrical contact with the conductive element and extending to a proximal end of the lead body. Each of the insulated conductors contacts a different circumferential portion of the conductive element before removing material from the conductive element. Each of the insulated conductors contacts a different one of the electrode segments after removing the material from the conductive element to form the electrode segments.

In another example, this disclosure is directed to an assembly for a medical lead comprising an elongated lead body and a conductive element located at a distal portion of the lead body. The conductive element substantially encircles a longitudinal axis of the lead body. The assembly further comprises a plurality of insulated conductors extending within the lead body, each of the insulated conductors being in electrical contact with the conductive element and extending to a proximal end of the lead body. Each of the insulated conductors contacts a different circumferential portion of the conductive element. The conductive element is configured to facilitate mechanical and electrical separation of different circumferential portions of the conductive element to form two or more electrode segments for the medical lead from the conductive element.

In a further example, this disclosure is directed to a system comprising an assembly for a medical lead. The assembly comprises an elongated lead body and a conductive element located at a distal portion of the lead body. The conductive element substantially encircles a longitudinal axis of the lead body. The assembly further comprises a plurality of insulated conductors extending within the lead body, each of the insulated conductors being in electrical contact with the conductive element and extending to a proximal end of the lead body. Each of the insulated conductors contacts a different circumferential portion of the conductive element. The conductive element is configured to facilitate mechanical and electrical separation of different circumferential portions of the conductive element to form two or more electrode segments for the medical lead from the conductive element. The system further comprises a stimulation generator configured to deliver electrical stimulation via a selected combination of the electrode segments of the medical lead once the different circumferential portions of the conductive element are mechanically and electrically separated. A proximal end of the medical lead is configured for coupling the medical lead to the stimulation generator.

As another example, this disclosure is directed to a medical lead comprising an elongated lead body, a set of two or more electrode segments in a circular arrangement at a common longitudinal position along the lead body, and a plurality of conductors extending within the lead body, each of the conductors being in electrical contact with one of the electrode segments and extending to a proximal end of the lead body. Each of the electrode segments includes an exposed outer surface and a protrusion extending into the lead body, wherein the protrusion includes concave features that secure the electrode segment to the lead body.

In another example, this disclosure is directed to a method of manufacturing a medical lead comprising securing a set of two or more electrode segments in a circular arrangement at a common longitudinal position within an elongated mold, each of the electrode segments including an outer surface facing outwardly in the circular arrangement and a protrusion located closer to the center of the circular arrangement than the outer surface, positioning a plurality of conductors within the elongated mold, each of the conductors being in electrical contact with one of the electrode segments and extending to a proximal end of the elongated mold, and injecting a polymeric material into the mold to form an elongated lead body that covers the conductors and the protrusions of the electrode segments. Following the formation of the lead body, the outer surfaces of the electrode segments are exposed and the protrusions of the electrode segments extend into the lead body. The protrusions include concave features that secure the electrode segment to the lead body.

In a further example, this disclosure is directed to a system comprising a medical lead, the medical lead comprising an elongated lead body, a set of two or more electrode segments in a circular arrangement at a common longitudinal position along the lead body, and a plurality of conductors extending within the lead body, each of the conductors being in electrical contact with one of the electrode segments and extending to a proximal end of the lead body. Each of the electrode segments includes an exposed outer surface and a protrusion extending into the lead body. The protrusion includes concave features that secure the electrode segment to the lead body. The system further comprises a stimulation generator configured to deliver electrical stimulation via a selected combination of the electrode segments of the medical lead. A proximal end of the medical lead is configured for coupling the medical lead to the stimulation generator.

As another example, this disclosure is directed to a method of manufacturing a medical lead comprising coupling each of a set of two or more electrode segments to at least one insulative element, and securing the electrode segments and the at least one insulative element within an elongated mold. The at least one insulative element combines with the mold to constrain the electrode segments in a circular arrangement at a common longitudinal position within the mold. The method further comprising injecting a polymeric material into the mold to form an elongated lead body, wherein, following the formation of the lead body, each of the electrode segments includes an exposed outer surface.

In a further example, this disclosure is directed to a medical lead comprising an elongated lead body, and an assembly including a set of two or more electrode segments coupled to at least one insulative element in a circular arrangement within the elongated lead body. Each of the electrode segments includes an exposed outer surface.

In another example, this disclosure is directed to a system comprising a medical lead, the medical lead comprising an elongated lead body, and an assembly including a set of two or more electrode segments coupled to at least one insulative element in a circular arrangement within the elongated lead body. Each of the electrode segments includes an exposed outer surface. The system further comprises a stimulation generator configured to deliver electrical stimulation via a selected combination of the electrode segments of the medical lead. A proximal end of the medical lead is configured for coupling the medical lead to the stimulation generator.

The details of the present disclosure are set forth in the accompanying drawings and the description below.

BRIEF DESCRIPTION OF DRAWINGS

FIGS. 24A-24E illustrate techniques for manufacturing a medical lead including overmolding protrusions on electrode segments to facilitate holding the electrode segments in a circular arrangement during molding of a lead body.

DETAILED DESCRIPTION

While the description primarily refers to implantable electrical stimulation leads and implantable medical devices that deliver electrical stimulation therapy to a patient's brain, e.g., DBS, the features and techniques described herein are useful in other types of medical device systems, which may include other types of implantable medical leads and implantable medical devices. For example, the features and techniques described herein may be used in systems with medical devices that deliver electrical stimulation therapy to a patient's heart, e.g., pacemakers, and pacemaker-cardioverter-defibrillators. As other examples, the features and techniques described herein may be embodied in systems that deliver other types of electrical stimulation therapy (e.g., spinal cord stimulation, peripheral nerve stimulation, pelvic nerve stimulation, gastric nerve stimulation or vagal nerve stimulation), stimulation of at least one muscle or muscle groups, stimulation of at least one organ such as gastric system stimulation, stimulation concomitant to gene therapy, and, in general, stimulation of any tissue of a patient.

In addition, while the examples shown in the figures include leads coupled at their proximal ends to a stimulation therapy controller, e.g., implantable medical device, located remotely from the electrodes, other configurations are also possible and contemplated. In some examples, a lead comprises a portion of a housing, or a member coupled to a housing, of stimulation generator located proximate to or at the stimulation site, e.g., as a microstimulator. In other examples, a lead comprises a member at stimulation site that is wirelessly coupled to an implanted or external stimulation generator or generator.

Figure 1:
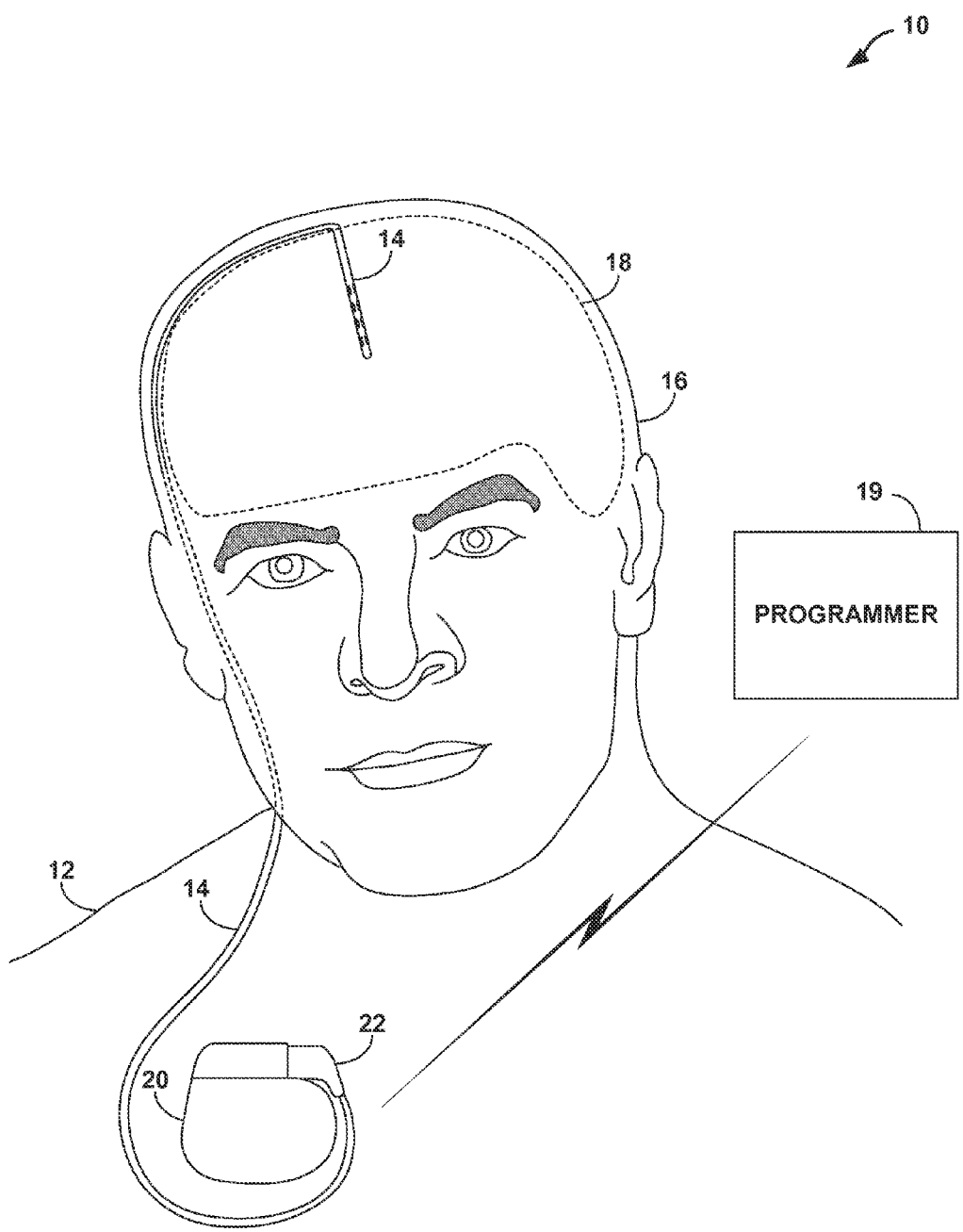
FIG. 1 is a conceptual diagram illustrating an example stimulation system with a stimulation lead implanted in the brain of a patient.

FIG. 1 is a conceptual diagram illustrating an example stimulation system with a stimulation lead implanted in the brain of a patient. As shown in FIG. 1, stimulation system 10 includes implantable medical device (IMD) 20 and lead 14 implanted within patient 12. Lead 14 includes lead plug 22 and lead body 24. Specifically, lead 14 enters through cranium 16 and is implanted within brain 18 to deliver deep brain stimulation (DBS). One or more electrodes of lead 14 provides electrical pulses to surrounding anatomical regions of brain 18 in a therapy that may alleviate a condition of patient 12. In some examples, more than one lead 14 may be implanted within brain 18 of patient 12 to stimulate multiple anatomical regions of the brain. As shown in FIG. 1, system 10 may also include a programmer 19, which may be a handheld device, portable computer, or workstation that provides a user interface to a clinician. The clinician interacts with the user interface to program stimulation parameters.

DBS may be used to treat dysfunctional neuronal activity in the brain which manifests as diseases or disorders such as Huntington's Disease, Parkinson's Disease, or movement disorders. The exact reasons why electrical stimulation therapy is capable of treating such conditions of the brain is unknown, but symptoms of these diseases can be lessened or eliminated with electrical stimulation therapy. Certain anatomical regions of brain 18 are responsible for producing the symptoms of such brain disorders. As one example, stimulating an anatomical region, such as the Substantia Nigra, in brain 18 may reduce the number and magnitude of tremors experienced by patient 12. Other anatomical regions may include the subthalamic nucleus, globus pallidus interna, ventral intermediate, and zona inserta. Anatomical regions such as these are targeted by the clinician during lead 14 implantation. In other words, the clinician may attempt to position the lead as close to these regions as possible.

While DBS may successfully reduce symptoms of some neurological diseases, the stimulation commonly may cause unwanted side effects as well. Side effects may include incontinence, tingling, loss of balance, paralysis, slurred speech, loss of memory, and many other neurological problems. Side effects may be mild to severe; however, most side effects are reversible when stimulation is stopped. DBS may cause one or more side effects by inadvertently providing electrical stimulation pulses to anatomical regions near the targeted anatomical region. For this reason, the clinician typically programs the stimulation parameters in order to balance effective therapy and minimal side effects.

Typical DBS leads include one or more electrodes placed along the longitudinal axis of the lead, such as lead 14. Each electrode is typically a ring electrode that resides along the entire circumference of the lead. Therefore, electrical current from the ring electrodes propagates in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects. Implanting a lead with a complex electrode array geometry may help to customize the stimulation field and provide improved therapy while decreasing side effects. In this manner, specific electrodes of the complex electrode array geometry may be selected to produce a stimulation field at desired portions of the circumference instead of always producing a stimulation field around the entire circumference of the lead. Also, the complex electrode array geometry may require a three dimensional method for a clinician to define which electrodes to use.

Lead 14 has a complex electrode array geometry in the preferred example, but the lead may also include one or more single ring electrodes along the longitudinal axis in other examples. For example, the disclosure may be applicable to leads having all ring electrodes, or one or more ring electrodes in combination with electrode segments at different axial positions and angular positions around the circumference of the lead. As an example, lead 14 includes a plurality of electrodes positioned at different axial positions along the longitudinal axis of the lead and a plurality of electrodes positioned at different angular positions around the circumference of the lead (which may be referred to as electrode segments). In this manner, electrodes may be selected along the longitudinal axis of lead 14 and along the circumference of the lead. Selectively activating electrodes of lead 14 can produce customizable stimulation fields that may be directed to a particular side of lead 14 in order to isolate the stimulation field around the target anatomical region of brain 18.

Producing irregular stimulation fields with a lead 14 with a complex electrode geometry not only may allow system 10 to more effectively treat certain anatomical regions of brain 18, but the system can also reduce or eliminate side effects from more spherical stimulation fields produced by a conventional array of ring electrodes. The center of the stimulation field may be moved away from lead 14 to avoid unwanted stimulation or compensate for inaccurately placed leads. If leads migrate within brain 18 slightly, a customizable stimulation field may provide a longer duration of effective therapy as stimulation needs of patient 12 change.

Programming lead 14 is more involved and complex when compared to traditional leads because of the increased number of possible electrode combinations and resulting stimulation fields. Effective programming may be difficult for the clinician if the clinician is required to systematically select each electrode of lead 14 in order to find the electrode combinations that provide therapy and minimal side effects. While the clinician may still desire the ability to manually select certain general areas of electrodes of lead 14, e.g., the group of circumferential electrodes at one level or length of the lead, programming time may be reduced if the clinician uses a user interface that enables the clinician to define a stimulation field and automatically generate the stimulation parameters that would produce the stimulation field in patient 12.

The user interface of programmer 19 displays a representation of the anatomical regions of patient 12, specifically anatomical regions of brain 18. The 3D space of the anatomical regions may be displayed as multiple 2D views or one 3D visualization environment. Lead 14 may also be represented on the display of the user interface, positioned according to the actual implantation location by the clinician or directly from an image taken of the lead within brain 18.

The clinician interacts with the user interface to manually select and program certain electrodes of lead 14 and adjust the resulting stimulation field with the anatomical regions as guides, or defining one or more stimulation fields only affect anatomical regions of interest. Once the clinician has defined the one or more stimulation fields, system 10 automatically generates the stimulation parameters associated with each of the stimulation fields and transmits the parameters to IMD 20.

System 10 may provide the clinician with additional tools that allow the clinician to accurately program the complex electrode array geometry of lead 14 for therapy. These tools may include creating and displaying a stimulation template set that corresponds to the stimulation field defined by the clinician. The stimulation template set may indicate to the clinician the actual stimulation that will occur based upon the stimulation field. Alternatively, system 10 may provide an electrical field or activation field to the clinician that illustrates the exact structures of the anatomical region that will be affected by the stimulation field. The electrical field may be indicative of the electrical propagation through the tissue surrounding lead 14, while the activation field may be indicative of the actual neurons within the electrical field that are activated by the therapy. Further, instead of or in addition to defining a stimulation field over an anatomical region of the patient, system 10 may provide a reference anatomical region of a reference anatomy, or an atlas, that allows the clinician to directly select the structures of the atlas that are targeted for therapy. The atlas may be mapped to the anatomical region of the patient anatomy or morphed together with the patient specific imaging to create a morphed atlas that indicates where each structure of the patient specific imaging resides. System 10 may then generate stimulation parameters to stimulate the selected structures. These alternative aspects of system 10 will be described in detail below.

Because clinicians are more familiar with physiology and anatomy than the operation and programming of stimulation parameters, clinicians may spend much less time configuring therapy for patient 12 by choosing what structures of the anatomical region should be stimulated. In some cases, system 10 may even indicate which structures the clinician has selected through the use of a pop-up bubble or structure list.

Alternatively, the clinician may be able to select one or more specific outcomes from a list, e.g., outcome selection input, where the outcome is a common result of stimulation to one or more structures of patient 12. Less clinician programming time with the user interface may result in a greater number of patients receiving effective therapy with potentially less side effects from time induced clinician mistakes.

The user interface provided in many different examples may allow a clinician to define a stimulation field which is used to generate stimulation parameters for IMD 20 and lead 14. A first example may utilize 2D views, or sections, of the anatomical regions of brain 18. The clinician may place a lead icon over the anatomical regions in each 2D view to represent the actual location of implanted lead 14. Once the lead icon is present, the clinician may select an electrode level and adjust the stimulation field position and magnitude by switching between different 2D views. Example 2D views may include coronal, sagittal, and axial slices of brain 18.

Another example is similar to the first example in that multiple 2D views are provided to the clinician to represent the 3D anatomical regions. The clinician defines, with an outline for example, one or more stimulation fields on three 2D views of the anatomical regions of patient 12. A 3D stimulation field volume is therefore defined by the 2D outlines and programmer 19 automatically generates appropriate stimulation parameters to at least approximate the defined field. The clinician may adjust the stimulation field by reviewing the 2D views and moving the outline. The outline may be established automatically by the programmer or the clinician may draw the outline using a stylus and touchscreen or other input media.

Further examples of system 10 allow the user to define a stimulation field on each of multiple 2D views in accordance to which structures of the anatomical region should be stimulated. System 10 then creates a stimulation template set that best fits the defined stimulation field. The stimulation template set that best fits the stimulation field may be presented to the clinician via the user interface over the defined stimulation field. If the clinician is not satisfied with the stimulation template set that is provided, the clinician may change the stimulation field until a template set is acceptable.

Other examples of system 10 provide an atlas to the clinician to reduce the difficulty of finding the desired structure to stimulate. In this case, the clinician may select the desired structure by selecting the structure from a simple drop down menu or from a graphical representation of the atlas. The atlas may be overlaid with the anatomical region of the patient anatomy for easy identification of structures of the patient. Alternatively, system 10 may generate a morphed atlas based upon the atlas and the patient anatomical region. Essentially, the locations of structures in the atlas are mapped to the patient anatomical region for selection.

Further examples of system 10 provide an electrical field model or an activation field model to the clinician over the anatomical region to indicate which structures will actually be affected by the defined stimulation. After defining the stimulation field and viewing the resulting electrical field or activation field, the clinician may be able to increase or decrease the amplitude to adjust the model according to what structures need to be stimulated by lead 14.

An additional example utilizes a 3D visualization environment that enables the clinician to view a 3D representation of anatomical regions of brain 18. The clinician places a 3D stimulation field within the anatomical regions and manipulates the shape, size, and placement of the 3D stimulation field to stimulate the target anatomical regions. The clinician may rotate and zoom the view to see exactly what anatomical regions the stimulation field will reach. A 3D lead icon may be present to show the clinician how the stimulation field relates to the position of implanted lead 14.

The 3D visualization environment may also incorporate an atlas, a morphed atlas, a stimulation template set, an electrical field model, or an activation model to assist the clinician in programming the stimulation therapy. The 3D environment allows the physician to rotate and zoom in on any portion of the 3D anatomical region represented in the 3D environment. The clinician can easily see which structures will be stimulated according to the defined stimulation field and which structures will be left unaffected. The 3D environment may reduce the amount of time the clinician must spend to initially program the stimulation therapy and optimize the therapy.

Other examples of the user interface are also contemplated, such as combinations of elements of the three examples described briefly above. For example, the clinician may select an electrode level of a lead icon in the 3D environment and manipulate the stimulation field provided by the electrodes of that electrode level. Some examples may begin with 2D views of the 3D anatomical regions and generate a 3D view of the defined stimulation field within the anatomical structures. In any example, the user interface may restrict clinician defined stimulation fields based upon the stimulation abilities of IMD 20 and lead 14. For example, the clinician may not make the stimulation field larger when the voltage cannot be increased or no more electrodes are available in the direction of the stimulation field. Additionally, the user interface may restrict the clinician from applying the stimulation field to an anatomical region or structure specifically banned from stimulation.

Stimulation of these areas may severely alter the physiology of patient 12 and cause detrimental side effects or irreversible side effects.

The stimulation field defined by the clinician using a user interface described herein is associated with certain stimulation parameter values. Programmer 19 automatically generates the stimulation parameters required by the stimulation field and wirelessly transmits the parameters to IMD 20. The parameters may also be saved on programmer 19 for review at a later time. In some cases, programmer 19 may not be capable of generating stimulation parameters that can produce the defined stimulation field within brain 18. Programmer 19 may display an error message to the clinician alerting the clinician to adjust the stimulation field. Programmer 19 may also display a reason why the stimulation field cannot be provided, such as the field is too large or an electrode is malfunctioning and cannot be used. Other errors may also be displayed to the clinician.

Generally, the user interface is not used to provide real-time programming to IMD 20. The clinician will use the user interface to define stimulation fields, and programmer 19 automatically generates the stimulation parameters when the clinician has determined the stimulation field is ready for therapy. In this manner, stimulation therapy perceived by patient 12 does not change at the same time the clinician changes the stimulation field. However, the user interface could be used as such in a real-time programming environment to provide immediate feedback to the clinician. In this manner, System 10 may also include multiple leads 14 or electrodes on leads of other shapes and sizes. The user interface may allow the clinician to program each lead simultaneously or require the clinician to program each lead separately. In some DBS patients, two leads 14 are implanted at symmetrical locations within brain 18 for bilateral stimulation. In particular, a first lead is placed in the right hemisphere of brain 18 and a second lead is placed at the same location within the left hemisphere of the brain. Programmer 19 may allow the clinician to create a stimulation field for the first lead and create a mirrored stimulation field for the second lead. The clinician may be able to make fine adjustment to either stimulation field do accommodate the slight anatomical region differences between the left and right hemispheres.

While lead 14 is described for use in DBS applications throughout this disclosure as an example, lead 14, or other leads, may be implanted at any other location within patient 12. For example, lead 14 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 12 and adjacent to sensitive nerve tissue. Therapy may also be changed if leads migrate to new locations within the tissue or patient 12 no longer perceives therapeutic effects of the stimulation.

Figure 2A:
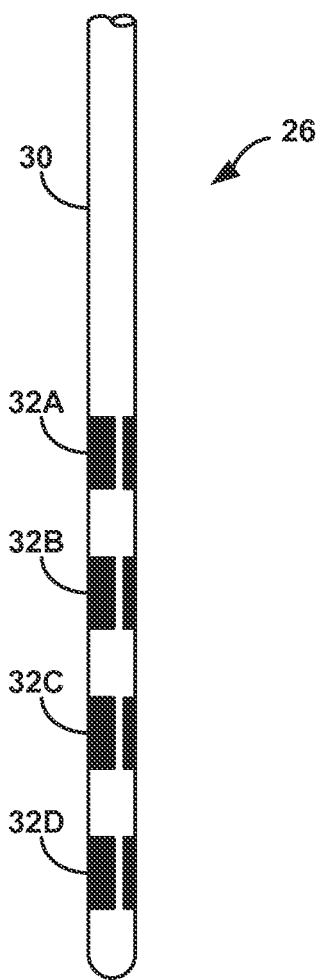
FIGS. 2A and 2B are conceptual diagrams illustrating two different implantable stimulation leads.
Figure 2B:
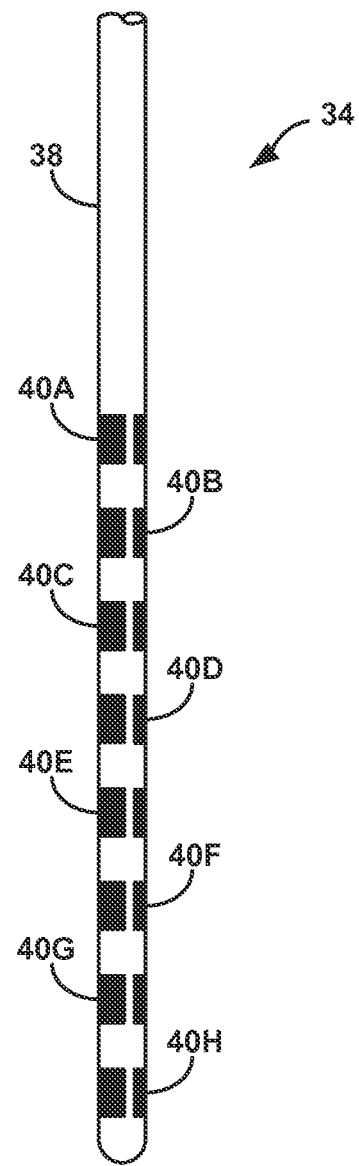

FIGS. 2A and 2B are conceptual diagrams illustrating two different implantable stimulation leads. Leads 26 and 34 are examples of lead 14 shown in FIG. 1. As shown in FIG. 2A, lead 26 includes four electrode levels 32 (includes levels 32A-32D) mounted at various lengths of lead housing 30. Lead 26 is inserted into through cranium 16 to a target position within brain 18.

Lead 26 is implanted within brain 18 at a location determined by the clinician to be near an anatomical region to be stimulated. Electrode levels 32A, 32B, 32C, and 32D are equally spaced along the axial length of lead housing 30 at different axial positions. Each electrode level 32 may have two or more electrodes located at different angular positions around the circumference of lead housing 30. Electrodes of one circumferential location may be lined up on an axis parallel to the longitudinal axis of lead 26. Alternatively, electrodes of different electrode levels may be staggered around the circumference of lead housing 30. In addition, lead 26 or 34 may include asymmetrical electrode locations around the circumference of each lead or electrodes of the same level that have different sizes. These electrodes may include semi-circular electrodes that may or may not be circumferentially aligned between electrode levels.

Lead housing 30 may include a radiopaque stripe (not shown) along the outside of the lead housing. The radiopaque stripe corresponds to a certain circumferential location that allows lead 26 to the imaged when implanted in patient 12. Using the images of patient 12, the clinician can use the radiopaque stripe as a marker for the exact orientation of lead 26 within the brain of patient 12. Orientation of lead 26 may be needed to easily program the stimulation parameters by generating the correct electrode configuration to match the stimulation field defined by the clinician. In other examples, a marking mechanism other than a radiopaque stripe may be used to identify the orientation of lead 14. These marking mechanisms may include something similar to a tab, detent, or other structure on the outside of lead housing 30. In some examples, the clinician may note the position of markings along lead body 24 during implantation to determine the orientation of lead 14 within patient 12.

FIG. 2B illustrates lead 34 that includes more electrode levels than lead 26. Similar to lead 26, lead 34 is inserted though a burr hole in cranium 16 to a target location within brain 18. Lead 34 includes lead housing 38. Eight electrode levels 40 (40A-40H) are located at the distal end of lead 34. Each electrode level 40 is evenly spaced from the adjacent electrode level and includes one or more electrodes. In a preferred example, each electrode level 40 includes four electrodes distributed around the circumference of lead housing 38. Therefore, lead 34 includes 32 electrodes in a preferred example. Each electrode may be substantially rectangular in shape. Alternatively, the individual electrodes may have alternative shapes, e.g., circular, oval, triangular, or the like.

In alternative examples, electrode levels 32 or 40 are not evenly spaced along the longitudinal axis of the respective leads 26 and 34. For example, electrode levels 32C and 32D may be spaced approximately 3 millimeters (mm) apart while electrodes 32A and 32B are 10 mm apart. Variable spaced electrode levels may be useful in reaching target anatomical regions deep within brain 18 while avoiding potentially dangerous anatomical regions. Further, the electrodes in adjacent levels need not be aligned in the direction as the longitudinal axis of the lead, and instead may be oriented diagonally with respect to the longitudinal axis.

Leads 26 and 34 are substantially rigid to prevent the implanted lead from varying from the expected lead shape. Leads 26 or 34 may be substantially cylindrical in shape. In other examples, leads 26 or 34 may be shaped differently than a cylinder. For example, the leads may include one or more curves to reach target anatomical regions of brain 18. In some examples, leads 26 or 34 may be similar to a flat paddle lead or a conformable lead shaped for patient 12. Also, in other examples, leads 26 and 34 may any of a variety of different polygonal cross sections taken transverse to the longitudinal axis of the lead.

Lead housings 30 and 38 may continue directly into lead body 24. A retention device may be used to squeeze the lead and shape it to approximately a 90 degree angle as it exits cranium 16. In some examples, lead housing 30 or 38 may include a right angle connector that allows lead 26 and 34 to be inserted into cranium 16 via a burr hole cap. In examples of system 10 including two or more leads 14, two or more leads may be connected to a common lead body 24. In this case, a connector at the surface of cranium 16 may couple each lead 14 to lead body 24.

Figure 3A:
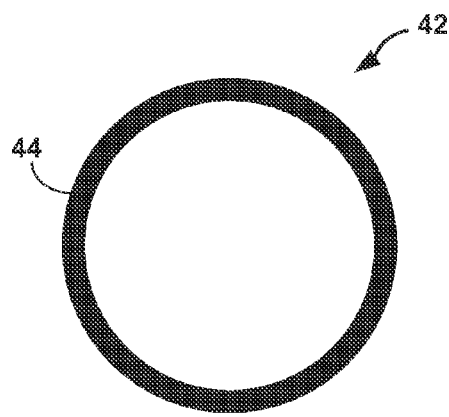
FIGS. 3A-3D are cross-sectional diagrams of example stimulation leads having one or more electrodes around the circumference of the lead.

FIGS. 3A-3D are transverse cross-sections of example stimulation leads having one or more electrodes around the circumference of the lead. As shown in FIGS. 3A-3D, one electrode level, such as one of electrode levels 32 and 40 of leads 26 and 34, respectively, are shown to include one or more circumferential electrodes. FIG. 3A shows electrode level 42 that includes circumferential electrode 44. Circumferential electrode 44 encircles the entire circumference of electrode level 42. Circumferential electrode 44 may be utilized as a cathode or anode as configured by the user interface.

Figure 3B:
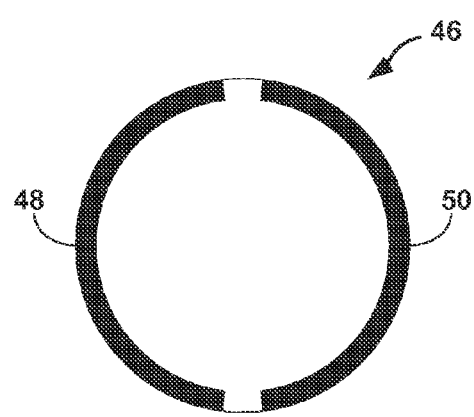

FIG. 3B shows electrode level 46 which includes two electrodes 48 and 50. Each electrode 48 and 50 wraps approximately 170 degrees around the circumference of electrode level 46. Spaces of approximately 10 degrees are located between electrodes 48 and 50 to prevent inadvertent coupling of electrical current between the electrodes. Each electrode 48 and 50 may be programmed to act as an anode or cathode.

Figure 3C:
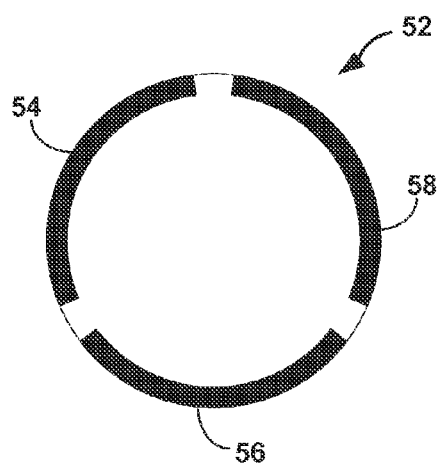

FIG. 3C shows electrode level 52 which includes three equally sized electrodes 54, 56 and 58. Each electrode 54, 56 and 58 encompass approximately 110 degrees of the circumference of electrode level 52. Similar to electrode level 46, spaces of approximately 10 degrees separate electrodes 54, 56 and 58. Electrodes 54, 56 and 58 may be independently programmed as an anode or cathode for stimulation.

Figure 3D:
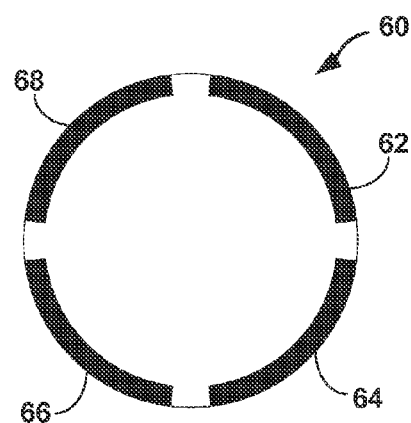

FIG. 3D shows electrode level 60 which includes four electrodes 62, 64, 66 and 68. Each electrode 62-68 covers approximately 80 degrees of the circumference with approximately 10 degrees of insulation space between adjacent electrodes. In other examples, up to ten or more electrodes may be included within an electrode level. In alternative examples, consecutive electrode levels of lead 14 may include a variety of electrode levels 42, 46, 52 or 60. For example, lead 14 may include electrode levels that alternate between electrode levels 52 and 60 depicted in FIGS. 3C and 3D. In this manner, various stimulation field shapes may be produced within brain 18 of patient 12. Further the above-described sizes of electrodes within an electrode level are merely examples, and other electrode sizes may be used within the spirit of this disclosure.

Also, the insulation space, or non-electrode surface area, may be of any size. Generally, the insulation space is between approximately 1 degree and approximately 20 degrees. More specifically, the insulation space may be between approximately 5 and approximately 15 degrees. Smaller insulation spaces may allow a greater volume of tissue to be stimulated. In alternative examples, electrode size may be varied around the circumference of an electrode level. In addition, insulation spaces may vary in size as well. Such asymmetrical electrode levels may be used in leads implanted at tissues needing certain shaped stimulation fields.

Figure 4:
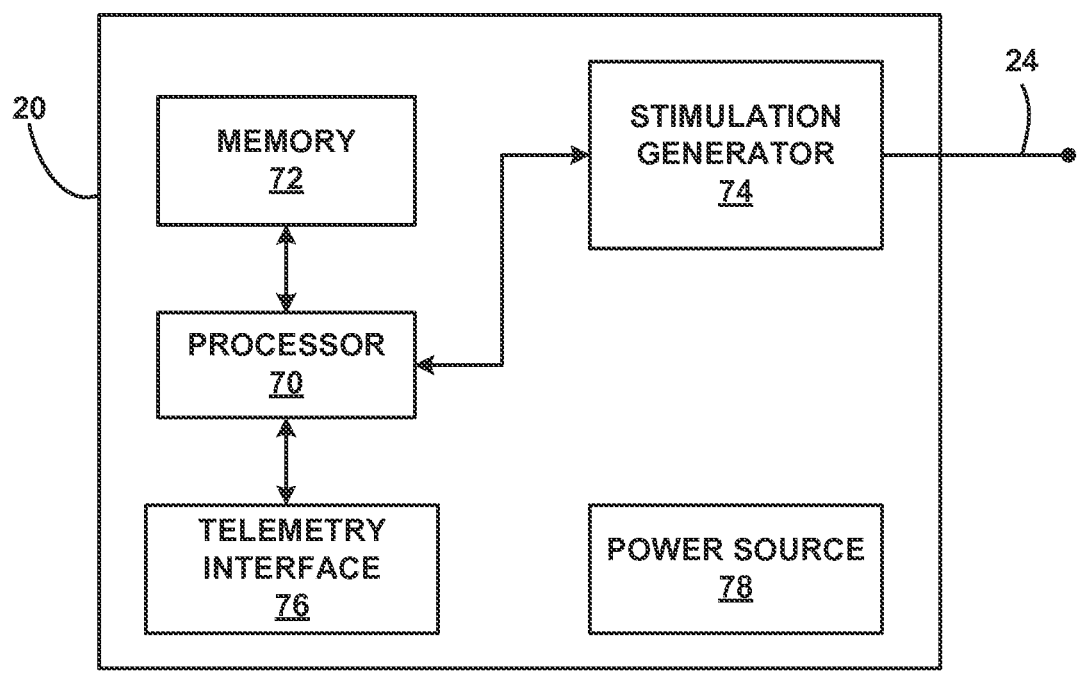
FIG. 4 is a functional block diagram of an example implantable medical device that generates electrical stimulation pulses.

FIG. 4 is a functional block diagram of an example implantable medical device that generates electrical stimulation signals. FIG. 4 illustrates components of IMD 20, which can be utilized by any of the IMD examples described herein. In the example of FIG. 4, IMD 20 includes a processor 70, memory 72, stimulation generator 74, telemetry interface 76, and power source 78. As shown in FIG. 4, stimulation generator 74 is coupled to lead body 24 (which includes lead 14). Alternatively, stimulation generator 74 may be coupled to a different number of leads as needed to provide stimulation therapy to patient 12.

Processor 70 controls stimulation generator 74 to deliver electrical stimulation therapy according to programs generated by a user interface and stored in memory 72 and/or received from programmer 19 via telemetry interface 76. As an example, a new program received from programmer 19 may modify the electrode configuration and amplitude of stimulation. Processor 70 may communicate with stimulation generator 74 to change the electrode configuration used during the therapy and modify the amplitude of stimulation. Processor 70 may then store these values in memory 72 to continue providing stimulation according to the new program. Processor 70 may stop the previous program before starting the new stimulation program as received from programmer 19. In some examples, amplitude of the stimulation signal may be ramped down or ramped up as a program is being turned off or turned on. In this manner, no abrupt stimulation changes may be perceived by patient 12. A ramp up of the new program may provide patient 12 time to stop stimulation if the new program is uncomfortable or even painful.

Processor 70 may comprise any one or more of a microprocessor, digital signal processor (DSP), application specific integrated circuit (ASIC), field-programmable gate array (FPGA), or other digital logic circuitry. Memory 72 stores instructions for execution by processor 70, e.g., instructions that when executed by processor 70 cause the processor and IMD to provide the functionality ascribed to them herein, as well as stimulation programs. Memory 72 may include any one or more of a random access memory (RAM), read-only memory (ROM), electronically-erasable programmable ROM (EEPROM), flash memory, or the like.

Stimulation generator 74 may provide stimulation in the form of pulses to patient 12. Alternatively, stimulation generator 74 may provide therapy in the form of some continuous signal such as a sine wave or other non-pulse therapy. Stimulation parameters for each stimulation program may include electrode configuration, current or voltage amplitude, pulse width, pulse rate, or duty cycle. Other parameters may be used depending on the therapy to be provided to patient 12. Stimulation generator 74 may independently utilize any circumferential electrodes 32 or 40 or leads 26 and 34, respectively. In this manner, stimulation generator 74 may be utilized to deliver stimulation via numerous different electrode configurations to provide therapy for a wide variety of patient conditions. In addition, stimulation generator 74 may test the functionality of electrodes on lead 14. Based upon the impedance testing, specific electrodes may be removed from possible use in therapy when the test indicates that the impedance is above or below normal operating limits.

Telemetry interface 76 may include circuitry known in the art for facilitating wireless telemetry, e.g., via radio frequency (RF) communication or proximal inductive interaction with similar circuitry within external programmer 19. Power source 78 delivers operating power to the components of IMD 20. Power source 78 may include a battery and a power generation circuit to produce the operating power. In some examples, the battery may be rechargeable to allow extended operation. Recharging may be accomplished through proximal inductive interaction between an external charger and an inductive charging coil within IMD 20. In other examples, non-rechargeable batteries may be used. As a further alternative, an external power supply could transcutaneously power IMD 20 whenever stimulation is needed or desired.

Figure 5:
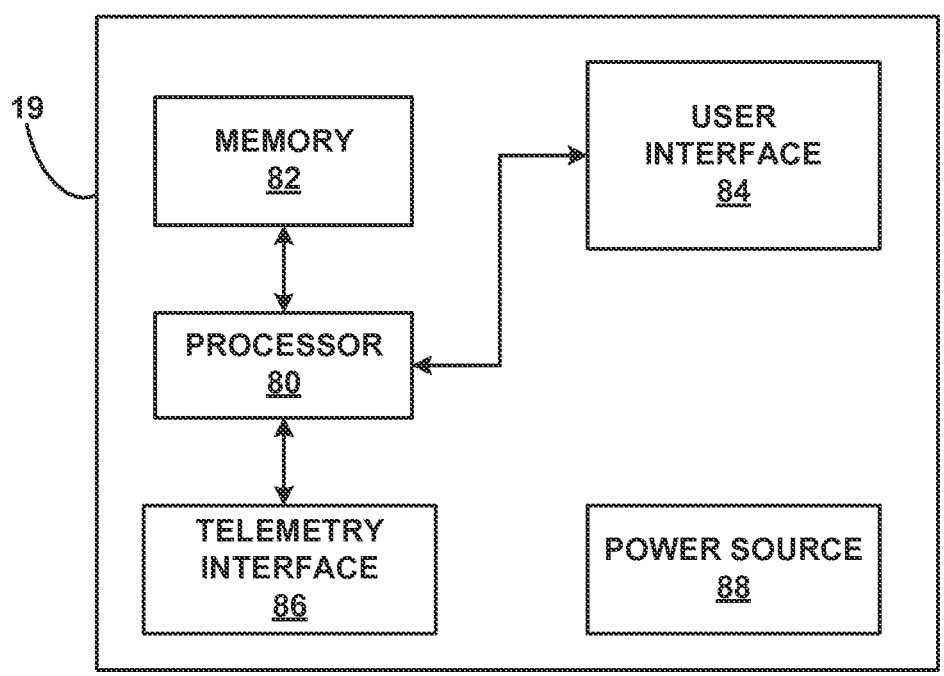
FIG. 5 is a functional block diagram of an example programmer for an implantable medical device.

FIG. 5 is a functional block diagram of an example programmer. As shown in FIG. 5, external programmer 19 includes processor 80, memory 82, user interface 84, telemetry interface 86, and power source 88. Programmer 19 may be used to present anatomical regions to the user via user interface 84, select stimulation programs, generate new stimulation programs with stimulation fields, and transmit the new programs to IMD 20. As described herein, programmer 19 may allow a clinician to define stimulation fields and generate appropriate stimulation parameters. For example, as described herein processor 80 may store stimulation parameters as one or more programs in memory 82. Processor 80 may send programs to IMD 20 via telemetry interface 86 to control stimulation automatically and/or as directed by the user.

Programmer 19 may be one of a clinician programmer or a patient programmer in some examples, i.e., the programmer may be configured for use depending on the intended user. A clinician programmer may include more functionality than the patient programmer. For example, a clinician programmer may include a more featured user interface, allow a clinician to download usage and status information from IMD 20, and allow a clinician to control aspects of the IMD not accessible by a patient programmer example of programmer 19.

A user, either a clinician or patient 12, may interact with processor 80 through user interface 84. Any of the user interface examples described herein may be examples of user interface 84, such as user interfaces 90, 314, 380, 456, 554, 600, 652, 730, 798, 850, 876, 916, 964, 1072, 1114, 1162, 1198. User interface 84 may include a display, such as a liquid crystal display (LCD), light-emitting diode (LED) display, or other screen, to show information related to stimulation therapy, and buttons or a pad to provide input to programmer 19. In examples where user interface 84 requires a 3D environment, the user interface may support 3D environments such as a holographic display, a stereoscopic display, an autostereoscopic display, a head-mounted 3D display, or any other display that is capable of presenting a 3D image to the user. Buttons may include an on/off switch, plus and minus buttons to zoom in or out or navigate through options, a select button to pick or store an input, and pointing device, i.e. a mouse, trackball, pointstick or stylus. Other input devices may be a wheel to scroll through options or a touch pad to move a pointing device on the display. In some examples, the display may be a touch screen that enables the user to select options directly from the display screen.

As described, the display may be more involved for the 3D user interface 189. In this case, programmer 19 may be a workstation within a laboratory, clinic room, or surgical room. The clinician may need to immerse within the display to fully utilize the functionality of the user interface. In some cases, programmer 19 may be a hand held device for all features except the 3D environment when the 3D environment necessitates a larger system. However, programmer 19 may still be integrated with or communicate with the 3D environment to simplify system 10 for the user.

Processor 80 processes instructions from memory 82 and may store user input received through user interface 84 into the memory when appropriate for the current therapy. In addition, processor 80 provides and supports any of the functionality described herein with respect to each example of user interface 84. Processor 80 may comprise any one or more of a microprocessor, digital signal processor (DSP), application specific integrated circuit (ASIC), field-programmable gate array (FPGA), or other digital logic circuitry.

Memory 82 may include instructions for operating user interface 84, telemetry interface 86 and managing power source 88. Memory 82 also includes instructions for generating stimulation fields and stimulation parameters from the stimulation fields. These instructions may include a set of equations needed to characterize brain tissue and interpret stimulation field dimensions. Memory 82 may include any one or more of a random access memory (RAM), read-only memory (ROM), electronically-erasable programmable ROM (EEPROM), flash memory, or the like. Processor 80 may comprise any one or more of a microprocessor, digital signal processor (DSP), application specific integrated circuit (ASIC), field-programmable gate array (FPGA), or other digital logic circuitry.

Memory 82 may store program instructions that, when executed by processor 80, cause the processor and programmer 19 to provide the functionality ascribed to them herein. For example, memory 82 may include a plurality of stimulation templates that are used by processor 80 to create a stimulation template set. Memory 82 may also include instructions for generating stimulation parameters based upon the defined stimulation field. In addition, instructions that allow processor 80 to create electrical field models and activation field models may be stored within memory 82. An atlas or reference anatomical region may also be stored in memory 82 for presentation to the clinician. In some examples, memory 82 does not contain instructions for all functionality for the user interfaces and programming of stimulation parameters as described herein. In this case, memory 82 may only hold the necessary instructions for the specific example that the user desires. Memory 82 may be reformatted with different sets of instructions when needed.

Wireless telemetry in programmer 19 may be accomplished by radio frequency (RF) communication or proximal inductive interaction of programmer 19 with IMD 20. This wireless communication is possible through the use of telemetry interface 86. Accordingly, telemetry interface 86 may include circuitry known in the art for such communication.

Power source 88 delivers operating power to the components of programmer 19. Power source 88 may include a battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries may be used. In addition, programmer 19 may be directly coupled to an alternating current source, such would be the case with a stationary workstation for 3D visualization environments.

Figure 6A:
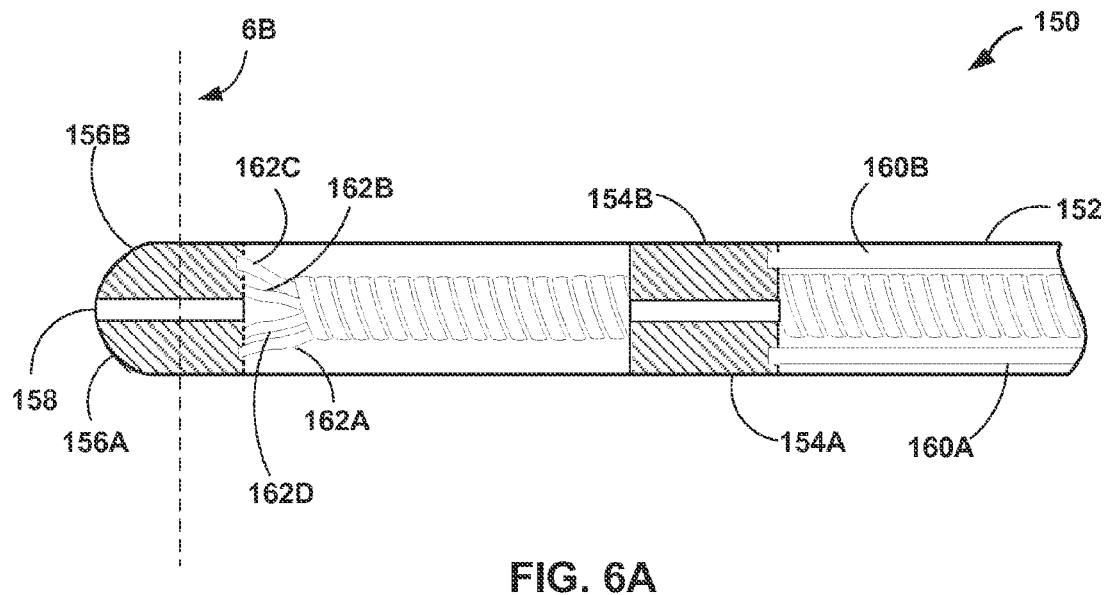
FIG. 6A is a side view of a distal end of an example lead including electrode segments at its distal tip.

FIG. 6A is a side view of a distal end of an example of a lead 150, which may, for example, correspond to lead 14 of FIG. 1. A proximal end (not shown) of lead 150 may be coupled to an IMD (e.g., IMD 20 of FIG. 1). Lead 150 includes a lead body 152 and electrodes 154A, 154B, and 156A-156D (electrodes 156C and 156D are not shown in FIG. 6A). Lead body 152 may be formed from a insulative biocompatible material. Exemplary biocompatible material includes at least one covers of polyurethane, silicone, and fluoropolymers such as tetrafluroethylene (ETFE), polytetrafluroethylene (PTFE), and/or expanded PTFE (i.e. porous ePTFE, nonporous ePTFE). Electrodes 154A, 154B, and 156A-156D are exposed to tissue of the patient, which allows data to be sensed from the tissue and/or therapy delivered to the patient.

As shown in FIG. 6A, electrodes 154A and 154B are substantially congruent with an outer surface of lead body 22, e.g., isodiametric with lead body 22 and may be segmented electrodes, each of the electrode segments 154A and 154B extending along an arc less than 360 degrees (e.g., 90-120 degrees). Segmented electrodes may be useful for providing an electrical stimulation field that is predominantly focused in a particular transverse direction relative to the longitudinal axis of lead 150, and/or targeting a particular stimulation site. In other examples, instead of or in addition to electrodes 154A and 154B, lead 150 may include a ring electrode extending substantially around the entire periphery, e.g., circumference, of lead 150.

Figure 6B:
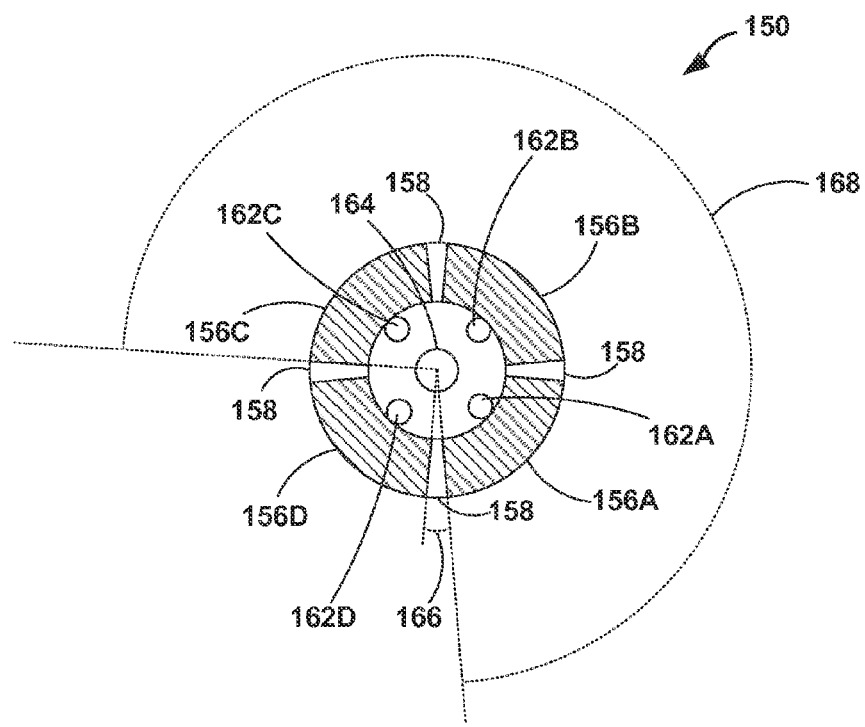
FIGS. 6B-6D are cross-sectional views of the electrode segments at the distal tip of the lead of FIG. 6A and an electrical field propagating directionally from the electrode segments.

In the illustrated example, electrodes 156A-156D are also segmented electrodes, which do not extend substantially around the entire periphery of the lead body 152. Electrodes 156C and 156D are located on the circumferential portion of lead body 152 not visible in FIG. 6A. As described in further detail below, FIG. 6B is a cross-sectional view of electrodes 156A-156D along line 6B in FIG. 6A, and illustrates the approximate locations of electrodes 156C and 156D. Electrodes 156A-156D may, but need not be, located at the same axial position along the length of lead body 152. When electrodes 156A-156D are located at the same axial position of lead body 152, electrodes 156A-156D may form a row of electrode segments. In some examples, electrodes 156A-156D may be evenly spaced around the periphery of lead 150. Additionally, each of individual electrode segments 156A-156D may be separated by insulative material 158, which may aid in electrically isolating each of electrodes 156A-156D.

Each of electrodes 154A, 154B, and 156A-156D can be made from an electrically conductive, biocompatible material, such as platinum iridium. In addition, in some examples, at least one of electrodes 154A, 154B, and 156A-156D may function as a sensing electrode that monitors internal, physiological, electrical signals of patient 12 (FIG. 1), such as electrical activity of brain 18 (FIG. 1) of patient 12. The configuration, type, and number of electrodes 154A, 154B, and 156A-156D are merely exemplary. In other examples, lead 150 may include any configuration, type, and number of electrodes 154A, 154B, and 156A-156D, and is not limited to the example illustrated in FIGS. 6A and 6B.

Within lead body 152, lead 150 also includes insulated electrical conductors 160A and 160B coupled to electrodes 154A and 154B, and insulated electrical conductors 162A-162D coupled to electrode segments 156A-156D, respectively. In the illustrated example, conductors 162A-162D are coiled along the length of lead body 152 (e.g., in a multiconductor coil), and conductors 160A and 160B lie axial to conductors 162A-162D. Conductors 160A and 160B may or may not be coiled. In the example illustrated in FIG. 6A, each of conductors 160A, 160B, and 162A-162D is electrically coupled to a single one of electrodes 154A, 154B, and 156A-156D, respectively. In this manner, each of electrodes 154A, 154B, and 156A-156D may be independently activated. In other examples, lead including multiple electrodes may include a multiplexer or other switching device such that the lead may include fewer conductors than electrodes, while allowing each of the electrodes to be independently activated. The switching device may be responsive to commands from the IMD or an external source to selectively couple the electrodes to the conductors for delivery of stimulation or for sensing.

The configuration, type, and number of conductors 160A, 160B, and 162A-162D is not limited to the example illustrated in FIG. 6A and, in other examples, lead 150 may include any configuration, type, and number of conductors. As one example, in some examples, each of conductors 160A, 160B, and 162A-162D may be coiled conductors. Additionally or alternatively, one conductor may be electrically coupled to at least two electrodes.

FIG. 6B is a cross-sectional view electrode segments 156A-156D along line 6B in FIG. 6A. As previously described, each of electrode segments 156A-156D is separated by insulative material 158. The center of lead body 152 may include a lumen 164 to accommodate a delivery device such as a stylet, guidewire or a hybrid of a stylet and guidewire. A delivery device may be used to help position lead 150 at a target location during implantation of lead 150. Electrical conductors 162A-162D are coupled to electrode segments 156A-156D, respectively. Each of conductors 162A-162D extends from electrodes 156A-156D to a proximal end of lead body 152 to couple electrodes 156A-156D to an IMD (e.g., IMD 12 of FIG. 1).

Electrode segments 156A-156D may be useful in directing a stimulation field toward a target site and/or away from a non-target, potentially undesirable, site. For example, at least one of electrode segments 156A-156D may be activated (e.g., as a cathode or an anode) to deliver stimulation to patient 12 (FIG. 1). The direction of the stimulation field, e.g., the radial direction relative to the longitudinal axis of elongated lead body 152 or "side" of the lead on which the field is present, may be based on which of electrode segments 156A-156D are activated. Electrode segments 156A-156D may be activated in unipolar combinations with one or more of electrode segments 156A-156D creating a stimulation field in combination with an electrode (e.g., anode) on the IMD housing, or electrode segments 156A-156D may be selectively activated to form bipolar or multipolar combinations of the various segmented electrodes to provide at least one anode and at least one cathode.

Electrodes 154A and 154B may further aid in steering the stimulation field in a particular direction and/or sensing a patient condition on a particular side of lead body 152. Additionally, a controlled current or voltage amplitude may be selected for each of the active electrodes. During movement of lead 20, at least one of the electrodes may produce different amplitudes to further aid in controlling the direction of the stimulation field. All else equal, in a system having two anodes with different amplitudes, each anode adjacent to a cathode, generally, the stimulation field is at least partially biased towards the anode with the higher current or voltage amplitude.

An electrode combination is a selected subset of one or more electrodes located on one or more implantable leads coupled to an implantable stimulator. The electrode combination also refers to the polarities of the electrode segments in the selected subset. The electrode combination, electrode polarities, voltage or current amplitude, pulse width and pulse rate together define a program for delivery of electrical stimulation therapy by an implantable stimulator via an implantable lead or leads. By selecting particular electrode combinations, including selected electrodes and polarities, a physician can target particular anatomic structures. By selecting values for amplitude, pulse width and pulse rate, the physician can attempt to optimize the electrical therapy delivered to the patient via the selected electrode combination or combinations.

In general, a clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width and a pulse rate for stimulation pulses to be delivered to the patient. A group of parameters, including electrode combination, electrode polarity, amplitude, pulse width and pulse rate, may be referred to as a program in the sense that they drive the neurostimulation therapy to be delivered to the patient. In some applications, an implantable stimulator may deliver stimulation therapy according to multiple programs either simultaneously or on a time-interleaved, overlapping or non-overlapping, basis.

As stimulation is moved from one electrode to another electrode around the periphery, e.g., circumference, of a lead, the stimulation may affect entirely different anatomical structures. For this reason, providing the clinician with an interface that shows the electrodes in relation the anatomical regions of the patient may be beneficial to effective and efficient programming. Displaying the anatomy of the patient to the clinician may allow the clinician to focus on configuring a stimulation field such that it is applied to targeted tissue, instead of manually manipulating electrodes of a lead to conform to the anatomical structures of the patient. Once desired stimulation field is "marked" on an anatomical region of the patient, a system may automatically generate the required stimulation parameters needed to approximate the defined stimulation field requested by the clinician. The stimulator then applies the stimulation parameters to produce the field within the patient.

In one example, the IMD (e.g., IMD 20 of FIG. 1) may configure a first electrode segment as a cathode and two adjacent electrode segments at a common axial position, which may be on opposite sides of the first electrode segment, as anodes. This configuration may be referred to as an "anodal shielding" configuration in the sense that the anodes act as a shield around the cathode to substantially prevent propagation of the electrical field from the cathode to tissue that is beyond the anodes, e.g., tissue on an opposite side of the anode than the cathode.

For example, IMD 20 may configure electrode segment 156B as a cathode and adjacent electrode segments 156A and 156C on opposite sides of electrode segment 156B as anodes. Electrode segments 156A and 156C (the anodes) may substantially constrain the electrical field propagating from electrode segment 156B (the cathode) to the side or angular section 168 of lead 150 that includes electrode segment 156B. The electrical field may be centered between electrode segments 156A and 156C and, depending on the stimulation amplitudes for each of electrode segments 156A-156C, may be centered substantially over electrode segment 156B. IMD 20 may activate electrode segments 156A-156D in different configurations based on the desired direction of the stimulation field. At least one of electrode segments 154A and 154B may additionally or alternatively be activated as an anode or cathode to aid in controlling the direction of propagation of the stimulation field.

Anodal shielding may limit the size of the stimulation field. For example, the anodes may determine the extent and shape of a volume of tissue to which the stimulation field propagates. In some examples, an anodal shielding configuration may prevent the stimulation field from extending past the anodes.

The spacing between each of electrode segments 156A-156D may also influence the size of the stimulation field. In the example illustrated in FIG. 6B, electrodes 156A-156D are evenly or about evenly spaced around the periphery of lead 150 with arc 166 separating each of electrodes 156A-156D. Separation arc 166 may be selected based on the desired size of the stimulation field. In other examples, electrode segments 156A-156C may be unevenly spaced around the periphery of lead 150.

Figure 6C:
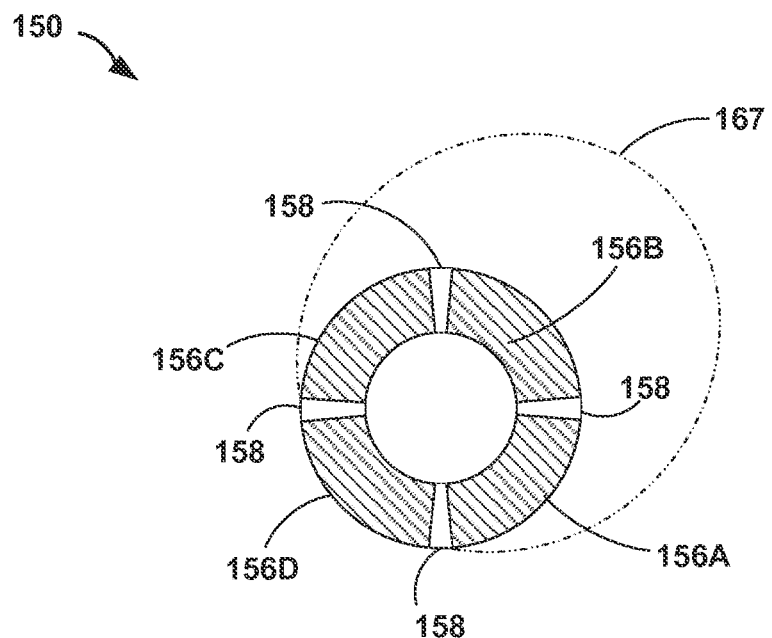

FIG. 6C is another cross-sectional view of electrode segments 156A-156D. FIG. 6C illustrates stimulation field 167 emanating from lead body 152. As described with respect to FIG. 6B, IMD 20 may configure electrode segment 156B as a cathode and adjacent electrodes segments 156A and 156C on opposite sides of electrode segment 156B as anodes. Electrode segments 156A and 156C (the anodes) may substantially constrain stimulation field 167 from propagating past electrode segments 156A and 156C (the anodes). In the example illustrated in FIG. 6C, stimulation field 167 is substantially centered over electrode segment 156B. For example, substantially similar voltage amplitudes may vary by no more than 0.1 volts, and substantially similar current amplitudes may vary by no more than 0.1 milliamps. IMD 20 may activate each of electrode segments 156A-156C with substantially the same amplitude to generate stimulation field 167 substantially centered over electrode segment 156B. IMD 20 may activate electrode segments 156A-156D in different configurations based on the desired direction of the stimulation field.

Figure 6D:
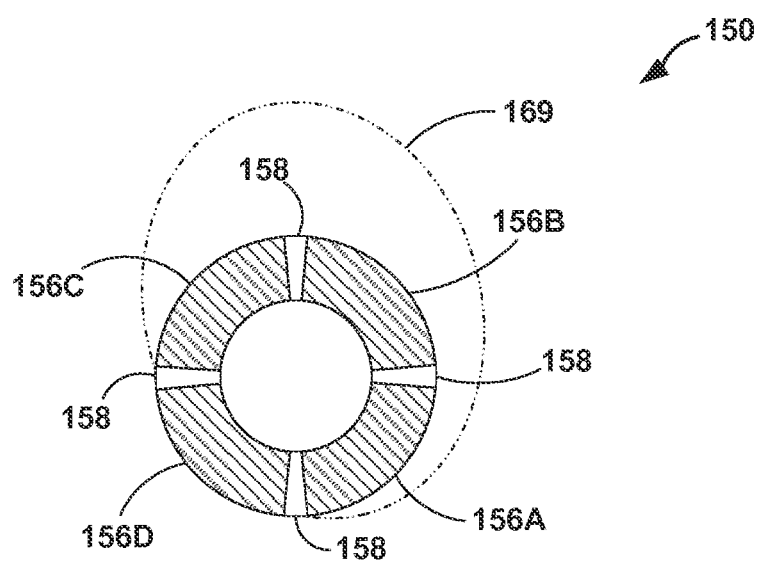

FIG. 6D is another cross-sectional view of electrode segments 156A-156D. FIG. 6D illustrates stimulation field 169 emanating from lead body 152. As described with respect to FIGS. 6B and 6C, IMD 20 may configure electrode segment 156B as a cathode and adjacent electrodes segments 156A and 156C on opposite sides of electrode segment 156B as anodes. Electrode segments 156A and 156C (the anodes) may substantially constrain stimulation field 169 from propagating past electrode segments 156A and 156C (the anodes). In the example illustrated in FIG. 6D, stimulation field 169 is skewed toward electrode 156C compared to stimulation field 167 of FIG. 6C. Rather than being substantially centered over electrode 156B (the central cathode), stimulation field 169 is shifted toward electrode 156C. IMD 20 may activate electrode segments 156A-156C with different current or voltage amplitudes to generate stimulation field 169 shifted toward electrode 156C. Additionally, IMD 20 may activate electrode segments 156A-156D in different configurations based on the desired direction of the stimulation field. For example, IMD 20 may selectively activate two of electrode segments 26A-26D, i.e., one as a cathode and another as an anode, to form a bipolar configuration.

Figure 7:
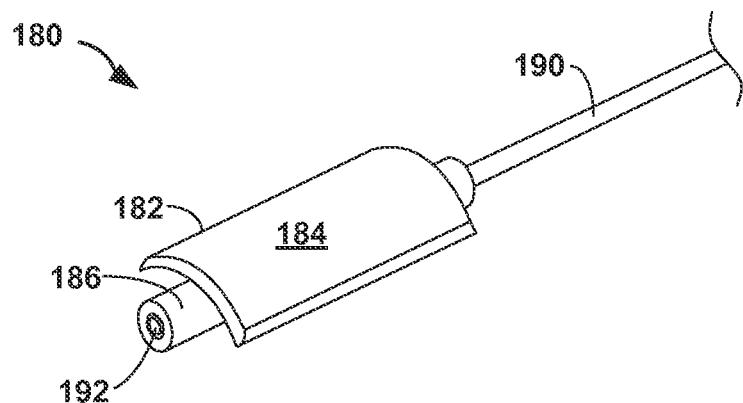
FIGS. 7-9F illustrate techniques for manufacturing a medical lead including an electrode segment holder to hold electrode segments within a mold during manufacturing.
Figure 8:
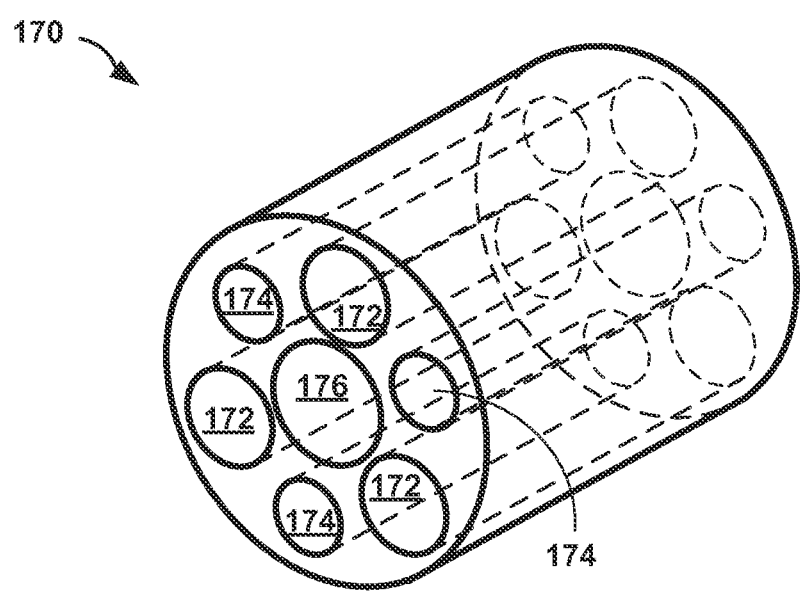

FIGS. 7-9F illustrate techniques for manufacturing a medical lead including an electrode segment holder to hold electrode segments within a mold during manufacturing. More specifically, FIG. 7 illustrates electrode segment 180, and FIG. 8 illustrates electrode segment holder 170. FIGS. 9A-9F illustrate exemplary steps for manufacturing medical lead 200 (FIG. 9F) using segment holder 170 and electrode segments 180.

As shown in FIG. 7, electrode segment 180 includes an electrode 182 forming an exposed outer surface 184 suitable for stimulation and/or sensing functions of medical lead 200. Tubular member 186 is connected to electrode 182, e.g., tubular member 186 is electrically conductive and may be soldered, welded, or brazed to electrode 182. Tubular member 186 is suitable to receive exposed end 192 of conductor 190. In some examples, conductor 190 may be a straight or coil conductor. Electrode segment 180 is formed from a conductive biocompatible material such as a platinum alloy, stainless steel or other metal.

As shown in FIG. 8, electrode segment holder 170 includes receptacles 172, which are configured to receive tubular members 186 of electrode segments 180 for manufacturing medical lead 200 as well as allow electrical conductors 190 of medical lead 200 to pass through electrode segment holder 170 to reach electrode segments 180. Electrode segment holder 170 further includes flow channels 174, which allow for material of the lead body 198 (FIG. 9F) to pass through electrode segment holder 170 and envelop electrode segment holder 170 during the molding of medical lead 200. In some examples, conductors may also be routed through flow channels 174, e.g., to electrode segments that are not adjacent to electrode segment holder 170. Electrode segment holder 170 also includes a center stylet channel 176.

Electrode segment holder 170 is an insulative element formed from an insulative material to electrically isolate electrode segments 180 from each other. In some examples, electrode segment holder 170 may be formed from polyurethane or a different polymeric material.

Figure 9A:
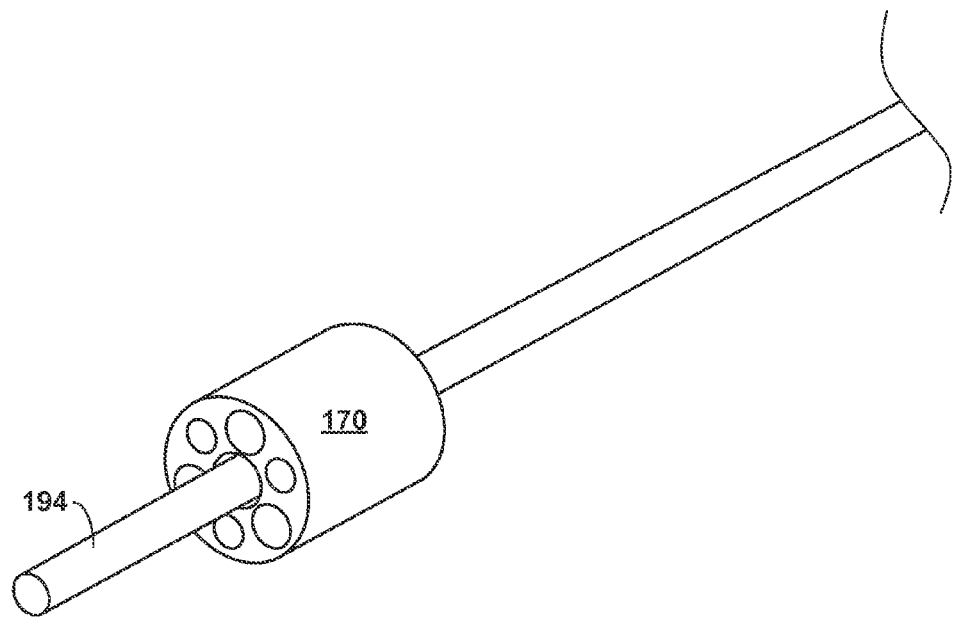

As mentioned above, FIGS. 9A-9F illustrate exemplary steps for manufacturing medical lead 200 using segment holder 170 and electrode segments 180. As shown in FIG. 9A, electrode segment holder 170 is first positioned over stylet 194 such that stylet 194 is within stylet channel 176 of electrode segment holder 170.

Figure 9B:
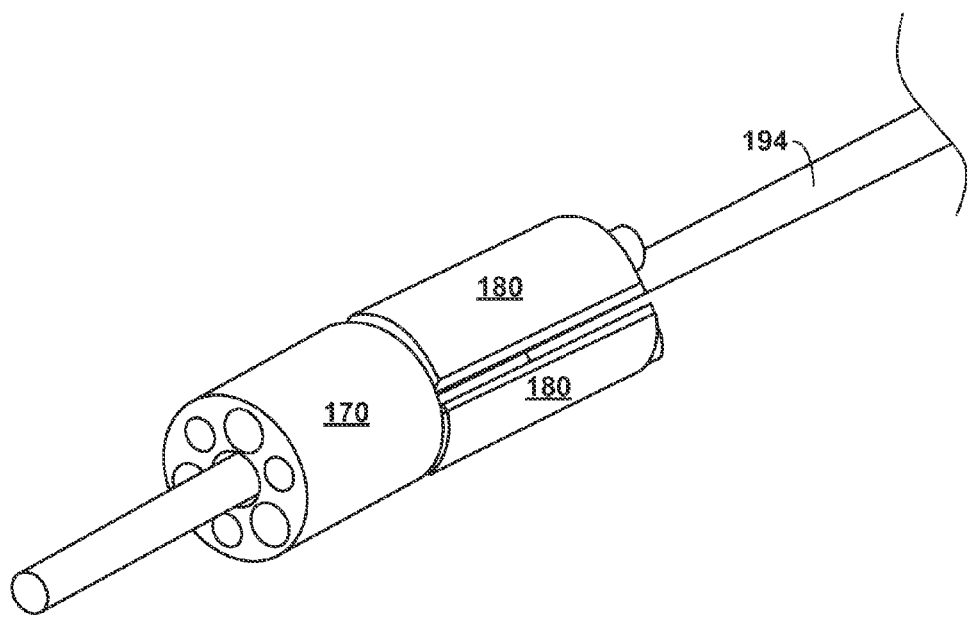

Next, as shown in FIG. 9B, electrode segments 180 assembled with electrode segment holder 170 such that the exposed ends of tubular members 186 are positioned within receptacles 172 of electrode segment holder 170 to position electrode segments 180 in a circular arrangement and couple electrode segments 180 to electrode segment holder 170. In this manner, the exposed ends of tubular members 186 serve as protrusions suitable for mounting electrode segments 180 into electrode segment holder 170. Note that conductors 190 (FIG. 7) for electrode segments 180 are not shown in FIGS. 9A-9F; however, conductors 190 may be secured to electrode segments 180 of medical lead 200 prior to assembling electrode segments 180 with electrode segment holder 170. Each of the conductors 190 may extend between one of electrode segments 180 and a proximal end of medical lead 200.

Figure 9C:
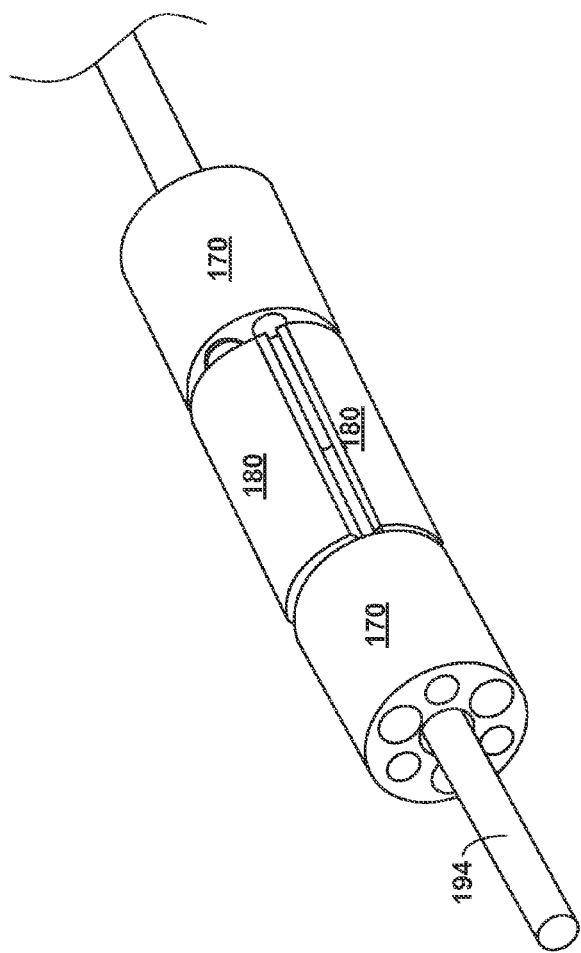
Figure 9D:
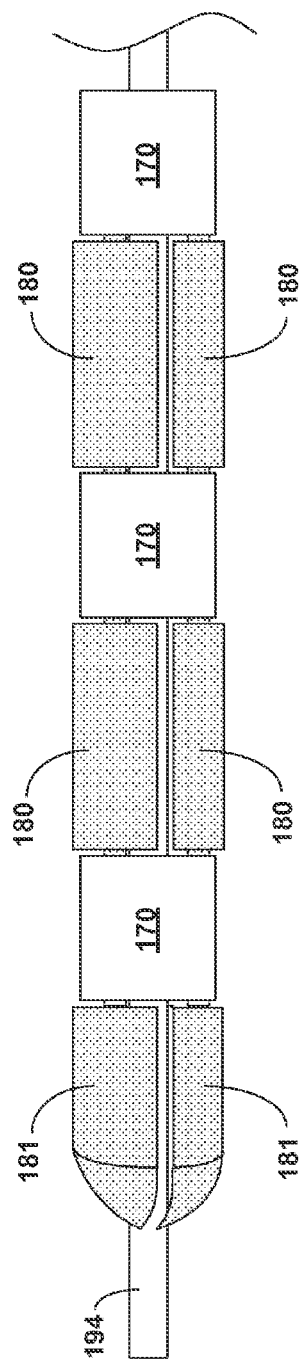

As shown in FIGS. 9C and 9D, additional electrode segments 180 and electrode segment holders 170 may be added to the assembly. In the example of medical lead 200, medical lead 200 includes two sets of electrode segments 180, each set within a circular arrangement as well as one set of tip electrode segments 181. Tip electrode segments 181 are similar to electrode segments 180 except that tip electrode segments 181 form a rounded distal surface for medical lead 200. Tip electrode segments 181 include tubular members that are received by receptacles 172 of the adjacent electrode segment holder 170. As shown in FIG. 9C, electrode segment holders 170 are interspersed between the set of tip electrode segments 181 and each set of electrode segments 180. The assembly shown in FIG. 9C also includes stylet 194.

Figure 9E:
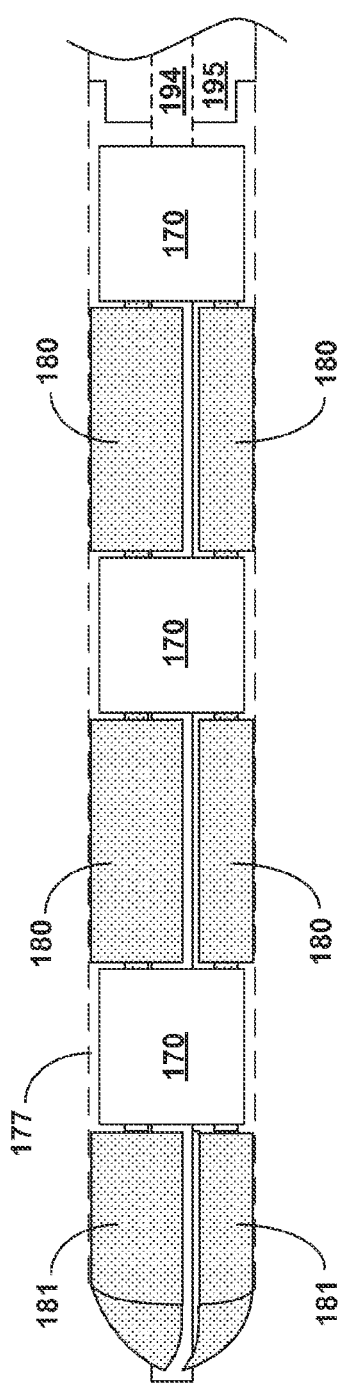
Figure 9F:
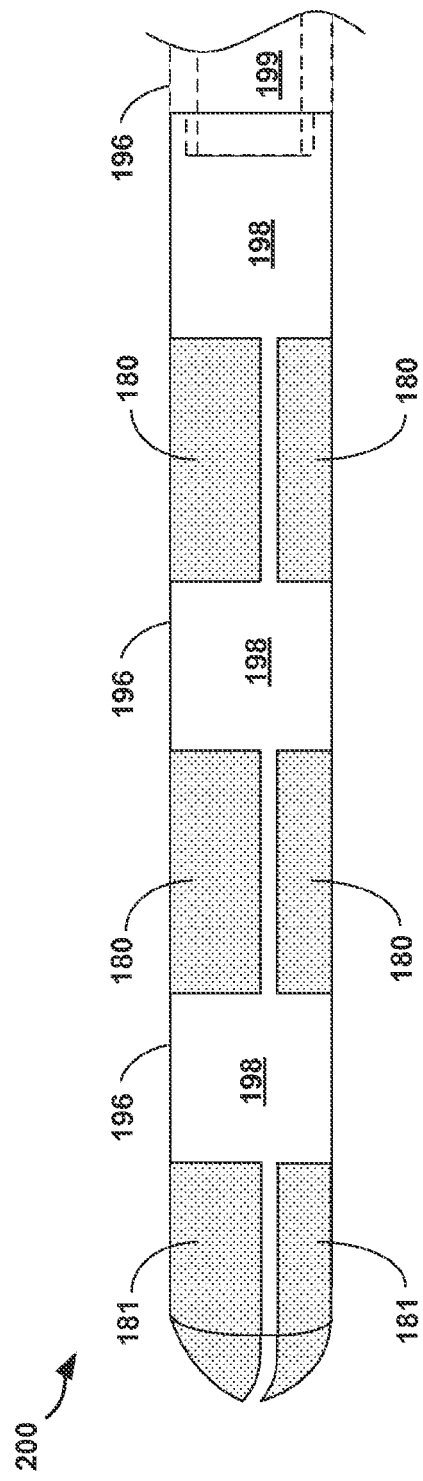

As shown in FIG. 9E, the entire assembly shown in FIG. 9D may then be placed in mold 177 to facilitate forming lead body 198. As also shown in FIG. 9E, mold mandrel 195 is located at the end of mold 177 opposite tip electrode segments 181. Within mold 177, electrode segment holders 170 constrain the set of tip electrode segments 181 and each set of electrode segments 180 in a circular arrangement at common longitudinal positions within mold 177.

In the example of medical lead 200, each circular arrangement of electrode segments 180 includes three equally spaced electrode segments 180. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

Once the components discussed above are positioned in mold 177, an overmold material may be injected into mold 177 to form lead body 198. Because the exposed outer surfaces 184 of electrode segments 180 were adjacent to the cavity of mold 177, outer surface 196 of lead body 198 is substantially congruent with outer surface 196 of lead body 198. Stylet 194 is removed to provide a central lumen within lead body 198. Lead 200 further includes tubular lead body 199, which is received by the features left by mold mandrel 195 during the overmolding process. For example, tubular lead body 199 may be secured with adhesive to the proximal end of the overmold component.

As mentioned above, each tip electrode segment 181 and electrode segment 180 is electrically coupled to a conductor 190. Each of the conductors 190 may extend between one of tip electrode segments 181 or electrode segments 180 and a proximal end of medical lead 200. In some examples, each of the conductors 190 may extend between one of electrode segments 180 and a connector at the proximal end of medical lead 200 to electrically connect the connector to electrode segments 180 and tip electrode segments 181.

In some examples, lead body 198 and medical lead 200 may have a substantially circular cross-sectional shape, although other cross-sectional shapes may also be used.

In some examples, medical lead 200 may be included in a system with a stimulation generator configured to deliver electrical stimulation via a selected combination of electrode segments 180 and tip electrode segments 181 of medical lead 200. In such a system, the proximal end of medical lead 200 is electrically connected to the stimulation generator, e.g., via a connector or otherwise. In some examples, the stimulation generator may be configured to deliver DBS and medical lead 200 may comprise a DBS lead.

Figure 10A:
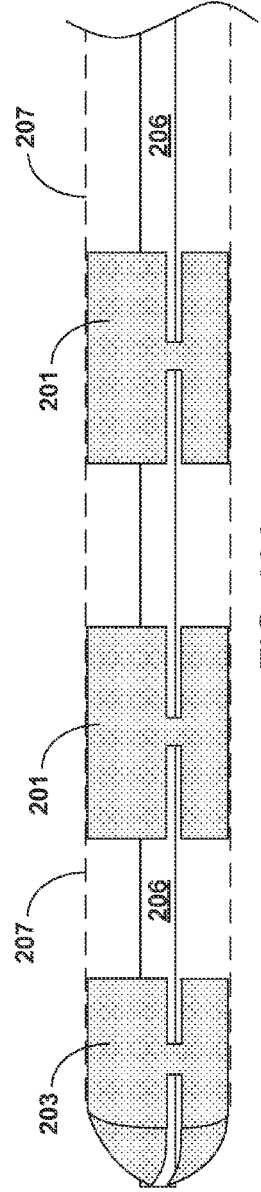
FIGS. 10A-10C illustrate techniques for manufacturing a medical lead including removing material from a conductive element to form two or more electrode segments from the conductive element.
Figure 10B:
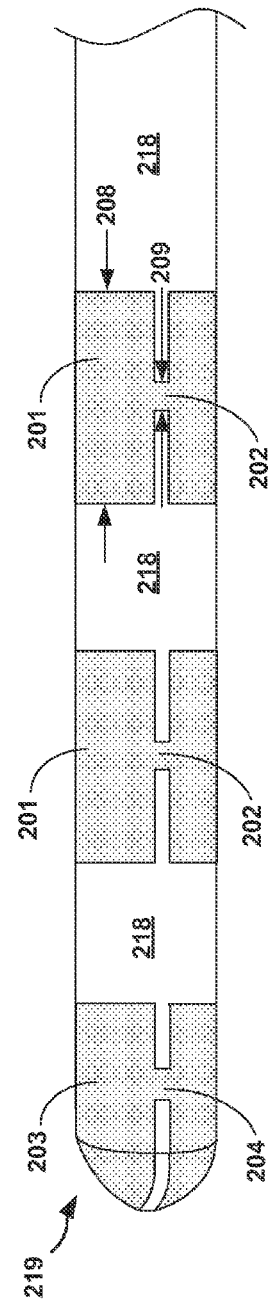
Figure 10C:
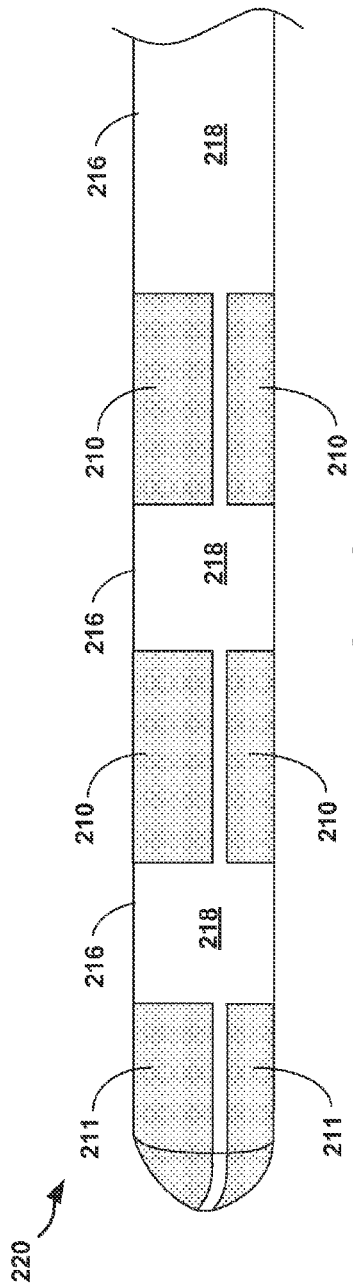

FIGS. 10A-10C illustrate techniques for manufacturing medical lead 220. The techniques of FIGS. 10A-10C including removing material from a conductive element to form two or more electrode segments from the conductive element.

As shown in FIG. 10A, three conductive elements: two conductive elements 201 configured to provide electrode segments 210 (FIG. 10C) and one distal tip conductive element 203 configured to provide tip electrode segments 211 (FIG. 10C), are positioned over stylet 206 and into mold 207.

Prior to locating conductive elements 201 and distal tip conductive element 203 within mold 207, conductive elements 201 and distal tip conductive element 203 are first coupled to conductors (not shown) to provide electrical connections for electrode segments 210 and tip electrode segments 211. As discussed with respect to medical lead 200, each of the conductors will extend within lead body 218 between one of electrode segments 210 or tip electrode segment 211 and a proximal end of medical lead 220.

Once the components discussed above are secured within elongated mold 207, an overmold material, such as a polymeric material, may be injected into mold 207 to form elongated lead body 218. After overmolding elongated lead body 218, stylet 206 is removed to provide a central lumen within lead body 218. The overmolding process produces assembly 219 (FIG. 10B). Within assembly 219, conductive elements 201 and distal tip conductive element 203 are located at a distal portion of lead body 218. Conductive elements 201 and distal tip conductive element 203 include exposed outer surfaces that were adjacent to the cavity of mold 207 such that these outer surfaces are substantially congruent with the outer surface of lead body 218. Further, each of conductive elements 201 substantially encircles a longitudinal axis of lead body 218 in assembly 219. In some examples, a tubular lead body as described with respect to lead 200 may be added to the proximal end of assembly 219.

As shown in assembly 219, each of conductive elements 201 as well as distal tip conductive element 203 is configured to facilitate mechanical and electrical separation of different circumferential portions of the conductive element to form two or more electrode segments. With respect conductive elements 201, conductive elements 201 include circumferential portions 202 configured to be removed alternating with the portions configured to form the electrode segments 210 for medical lead 220. Likewise, distal tip conductive element 203 includes circumferential portions 204 configured to be removed alternating with the portions configured to form the tip electrode segments 211 for medical lead 220.

As indicated in FIG. 10B, each circumferential portion 202 configured to be removed defines a width 209 as measured in a longitudinal direction about lead body 218 that is substantially less than the width 208 of the portions configured to form electrode segments 218 for the medical lead as measured in the longitudinal direction about lead body 218. In some examples, the portions 202 configured to be removed are approximately centered relative to the portions configured to form electrode segments 218 for the medical lead along the longitudinal dimension of the portions configured to form electrode segments 218. In other examples, circumferential portion 202 configured to be removed can be positioned at an location along the slot between the portions configured to form electrode segments 218, including at the ends or even along the entire width 208.

Figure 13:
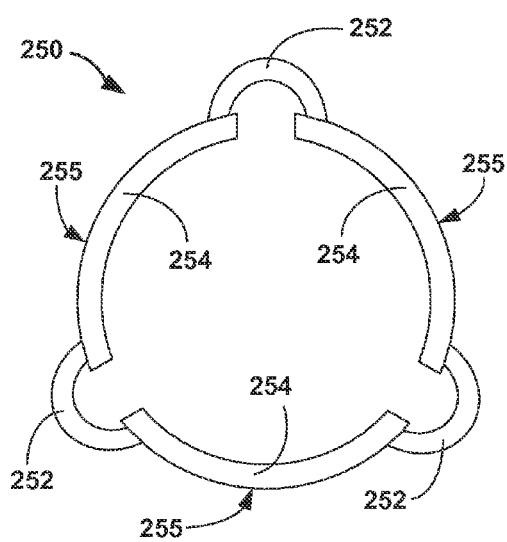
Figure 14:
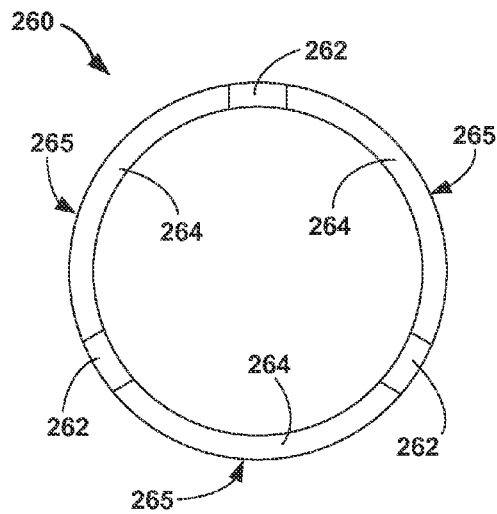

In some examples, as shown with respect to FIG. 14, circumferential portions 202 of conductive elements 201 and circumferential portions 204 of distal tip conductive element 203 are substantially congruent with an outer surface of lead body 218. In other examples, as shown with respect to FIGS. 11-13, circumferential portions 202 of conductive elements 201 and circumferential portions 204 of distal tip conductive element 203 extend outwardly beyond the outer surface of lead body 218.

As mentioned above with respect to FIG. 10A, for each of conductive elements 201 and distal tip conductive element 203, a plurality of insulated conductors is in electrical contact with the conductive element and extend within lead body 218 to a proximal end of lead body 218. These conductors will provide separate electrical connections to each of electrode segments 210 that will be formed from conductive elements 201 and each of tip electrode segments 211 that will be formed from conductive elements 203. In this manner, for each of conductive elements 201 and distal tip conductive element 203, each of the insulated conductors contacts a different circumferential portion of the conductive element.

After overmolding lead body 218 to form assembly 219, material is removed from each of conductive elements 201 to form two sets of electrode segments 210 in a circular arrangements at common longitudinal positions. Likewise, material is removed from distal tip conductive element 203 to form a set of tip electrode segments 211. Removing this material from conductive elements 201 and distal tip conductive element 203 in assembly 219 produces medical lead 220 (FIG. 10C). In different examples, material may be removed by cutting, laser cutting, grinding, bending, melting or other techniques. Following material removal, the remaining electrode segments may be polished to smooth the exposed surfaces.

Within medical lead 220, each of the insulated conductors contacts a different one of electrode segments 210 or tip electrode segments 211. Each of the conductors may extend between one of tip electrode segments 211 or electrode segments 210 and a proximal end of medical lead 220. In some examples, each of the conductors may extend between one of electrode segments 210 or tip electrode segments 211 and a connector at the proximal end of medical lead 220 to electrically connect the connector to electrode segments 210 and tip electrode segments 211.

In the example of medical lead 220, each circular arrangement of electrode segments 210 includes three equally spaced electrode segments 210. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement. In addition, a medical lead may include one or more ring electrodes in combination with one or more sets of electrode segments within a circular arrangement.

In some examples, lead body 218 and medical lead 220 may have a substantially circular cross-sectional shape, although other cross-sectional shapes may also be used.

In some examples, medical lead 220 may be included in a system with a stimulation generator configured to deliver electrical stimulation via a selected combination of electrode segments 210 and tip electrode segments 211 of medical lead 220. In such a system, the proximal end of medical lead 220 is electrically connected to the stimulation generator, e.g., via a connector or otherwise. In some examples, the stimulation generator may be configured to deliver DBS and medical lead 220 may comprise a DBS lead.

FIGS. 11-15B illustrate exemplary conductive elements from which material can be removed suitable to form two or more electrode segments as described with respect to FIGS. 10A-10C.

Figure 11:
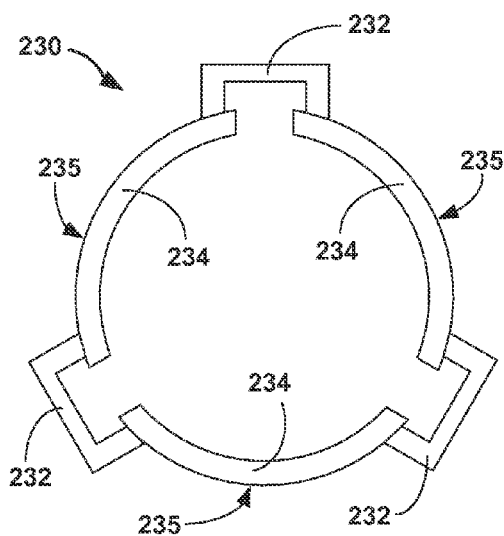
FIGS. 11-15B illustrate exemplary conductive elements from which material can be removed to form two or more electrode segments as described with respect to FIGS. 10A-10C.
Figure 12:
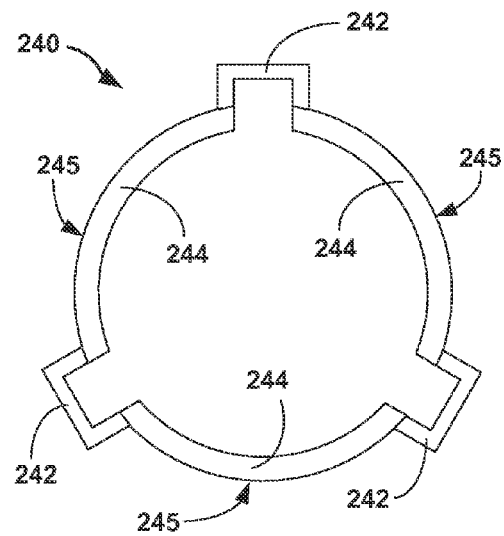

The conductive elements 230, 240, 250 of FIGS. 11-13 include circumferential portions (232, 242, 252) configured to be removed that extend outwardly beyond the outer surface of a lead body when part of an assembly such as assembly 219. In contrast, conductive element 260 of FIG.

14 includes circumferential portions 262 configured to be removed that are substantially congruent with an outer surface of the lead body when part of an assembly such as assembly 219. Conductive element 270 of FIGS. 15A-15B comprises a frame element 272 that maintains the relative positions of the portions of the conductive element configured to form electrode segments for a medical lead. Thus, conductive element 270 also includes portions configured to be removed that extend outwardly beyond the outer surface of the lead body when part of an assembly similar to assembly 219. Generally, conductive elements 230, 240, 250, 260, 270 are each unitary components such that portions configured to be removed are formed from the same conductive material as portions of the conductive element configured to form electrode segments. In other examples, conductive elements 230, 240, 250, 260, 270 may be formed from multiple components such that that portions configured to be removed may be formed from a different material than portions of the conductive element configured to form electrode segments As shown in FIG. 11, conductive element 230 is configured to facilitate mechanical and electrical separation of different circumferential portions of conductive element 230 to form two or more electrode segments for a medical lead. Specifically, conductive element 230 includes circumferential portions 232 configured to be removed alternating with circumferential portions 234 configured to form the electrode segments for the medical lead. Circumferential portions 234 form exposed outer surfaces 235 suitable for stimulation and/or sensing functions of a medical lead.

Circumferential portions 234 configured to form the electrode segments for the medical lead are configured to be substantially congruent with an outer surface of the lead body, whereas circumferential portions 232 configured to be removed are configured to extend outwardly beyond an outer surface of the lead body. Conductive element 230 may be secured within a mold, such as mold 207 (FIG. 10A), by holding circumferential portions 232 prior to injecting material into the mold to form an elongated lead body. In this manner, circumferential portions 232 may facilitate not only maintaining the positions of circumferential portions 234 relative to each other, but also the absolute positions of circumferential portions 234 within the mold.

In the specific example of conductive element 230, each circumferential portion 232 configured to be removed spans two adjacent circumferential portions 234 configured to form the electrode segments for the medical lead. Each circumferential portion 232 configured to be removed provides a rectangular shape that connects to outer surfaces 235 of circumferential portions 234 configured to form the electrode segments for the medical lead, but not on the edges of the outer surfaces 235. In this manner, after removing each circumferential portion 232 from conductive element 230, e.g., by cutting, grinding, laser etching, bending fatigue or otherwise, the former attachment points between circumferential portions 232 and circumferential portions 234 may be smoothed, e.g., by grinding, sanding, burnishing and/or polishing without damaging the lead body. It may be important to smooth outer surfaces 235 to prevent concentration of electrical charges during electrical stimulation of the medical lead.

In some examples, as discussed with respect to conductive elements 201 of assembly 219 (FIG. 10B), each circumferential portion 232 configured to be removed may define a width (not shown) that is substantially less than the width of circumferential portions 234 configured to form electrode segments for a medical lead as measured in the longitudinal direction of a lead body. In some examples, circumferential portions 232 may be approximately centered relative to the circumferential portions 234 in the longitudinal direction of a lead body. In other examples, a circumferential portion 232 may define a width (not shown) that is substantially equal to the width of the circumferential portions 234 as measured in the longitudinal direction of a lead body.

As shown in FIG. 12, conductive element 240 is configured to facilitate mechanical and electrical separation of different circumferential portions of conductive element 240 to form two or more electrode segments for a medical lead. Specifically, conductive element 240 includes circumferential portions 242 configured to be removed alternating with circumferential portions 244 configured to form the electrode segments for the medical lead. Circumferential portions 244 form exposed outer surfaces 245 suitable for stimulation and/or sensing functions of a medical lead.

Circumferential portions 244 configured to form the electrode segments for the medical lead are configured to be substantially congruent with an outer surface of the lead body, whereas circumferential portions 242 configured to be removed are configured to extend outwardly beyond an outer surface of the lead body. Conductive element 240 may be secured within a mold, such as mold 207 (FIG. 10A), by holding circumferential portions 242 prior to injecting material into the mold to form an elongated lead body. In this manner, circumferential portions 242 may facilitate not only maintaining position of circumferential portions 244 relative to each other, but also the absolute positions of circumferential portions 244 within the mold.

In the specific example of conductive element 240, each circumferential portion 242 configured to be removed spans two adjacent circumferential portions 244 configured to form the electrode segments for the medical lead. Each circumferential portion 242 configured to be removed provides a rectangular shape that connects to outer surfaces 245 of circumferential portions 244 configured to form the electrode segments for the medical lead adjacent to the edges of the outer surfaces 245. After removing each circumferential portion 242 from conductive element 240, e.g., by cutting, bending fatigue or otherwise, the former attachment points between circumferential portions 242 and circumferential portions 244 may be smoothed, e.g., by grinding, sanding, burnishing and/or polishing. It may be important to smooth outer surfaces 245 to prevent concentration of electrical charges during electrical stimulation of the medical lead.

In some examples, as discussed with respect to conductive elements 201 of assembly 219 (FIG. 10B), each circumferential portion 242 configured to be removed may define a width (not shown) that is substantially less than the width of circumferential portions 244 configured to form electrode segments for a medical lead as measured in the longitudinal direction of a lead body. In some examples, circumferential portions 242 may be approximately centered relative to the circumferential portions 244 in the longitudinal direction of a lead body. In other examples, a circumferential portion 242 may define a width (not shown) that is substantially equal to the width of the circumferential portions 244 as measured in the longitudinal direction of a lead body.

As shown in FIG. 13, conductive element 250 is configured to facilitate mechanical and electrical separation of different circumferential portions of conductive element 250 to form two or more electrode segments for a medical lead. Specifically, conductive element 250 includes circumferential portions 252 configured to be removed alternating with circumferential portions 254 configured to form the electrode segments for the medical lead. Circumferential portions 254 form exposed outer surfaces 255 suitable for stimulation and/or sensing functions of a medical lead.

Circumferential portions 254 configured to form the electrode segments for the medical lead are configured to be substantially congruent with an outer surface of the lead body, whereas circumferential portions 252 configured to be removed are configured to extend outwardly beyond an outer surface of the lead body. Conductive element 250 may be secured within a mold, such as mold 207 (FIG. 10A), by holding circumferential portions 252 prior to injecting material into the mold to form an elongated lead body. In this manner, circumferential portions 252 may facilitate not only maintaining position of circumferential portions 254 relative to each other, but also the absolute positions of circumferential portions 254 within the mold.

In the specific example of conductive element 250, each circumferential portion 252 configured to be removed spans two adjacent circumferential portions 254 configured to form the electrode segments for the medical lead. Each circumferential portion 252 configured to be removed provides an elliptical shape that connects to outer surfaces 255 of circumferential portions 254 configured to form the electrode segments for the medical lead, but not on the edges of the outer surfaces 255. In this manner, after removing each circumferential portion 252 from conductive element 250, e.g., by cutting, bending fatigue or otherwise, the former attachment points between circumferential portions 252 and circumferential portions 254 may be smoothed, e.g., by grinding, sanding, burnishing and/or polishing without damaging the lead body. It may be important to smooth outer surfaces 255 to prevent concentration of electrical charges during electrical stimulation of the medical lead.

In some examples, as discussed with respect to conductive elements 201 of assembly 219 (FIG. 10B), each circumferential portion 252 configured to be removed may define a width (not shown) that is substantially less than the width of circumferential portions 254 configured to form electrode segments for a medical lead as measured in the longitudinal direction of a lead body. In some examples, circumferential portions 252 may be approximately centered relative to the circumferential portions 254 in the longitudinal direction of a lead body. In other examples, a circumferential portion 252 may define a width (not shown) that is substantially equal to the width of the circumferential portions 254 as measured in the longitudinal direction of a lead body.

As shown in FIG. 14, conductive element 260 is configured to facilitate mechanical and electrical separation of different circumferential portions of conductive element 260 to form two or more electrode segments for a medical lead. Specifically, conductive element 260 includes circumferential portions 262 configured to be removed alternating with circumferential portions 264 configured to form the electrode segments for the medical lead. Circumferential portions 264 form exposed outer surfaces 265 suitable for stimulation and/or sensing functions of a medical lead.

Circumferential portions 264 configured to form the electrode segments for the medical lead are configured to be substantially congruent with an outer surface of the lead body as are circumferential portions 262. Circumferential portions 262 facilitate maintaining position of circumferential portions 264 relative to each other during molding of a lead body. In addition, the entirety of conductive element 260 may be secured within the mold, e.g., by being clamped between two halves of the mold to maintain the absolute position of circumferential portions 264 within the mold.

In the specific example of conductive element 260, each circumferential portion 262 configured to be removed spans two adjacent circumferential portions 264 configured to form the electrode segments for the medical lead. Each circumferential portion 262 configured to be removed touches an inner edge of the adjacent circumferential portions 264 configured to form the electrode segments for the medical lead. In this manner, removing each circumferential portion 262 from conductive element 260 may allow outer surfaces 265 to remain smooth.

In some examples, as discussed with respect to conductive elements 201 of assembly 219 (FIG. 10B), each circumferential portion 262 configured to be removed may define a width (not shown) that is substantially less than the width of circumferential portions 264 configured to form electrode segments for a medical lead as measured in the longitudinal direction of a lead body. In some examples, circumferential portions 262 may be approximately centered relative to the circumferential portions 264 in the longitudinal direction of a lead body. In other examples, a circumferential portion 262 may define a width (not shown) that is substantially equal to the width of the circumferential portions 264 as measured in the longitudinal direction of a lead body.

Figure 15A:
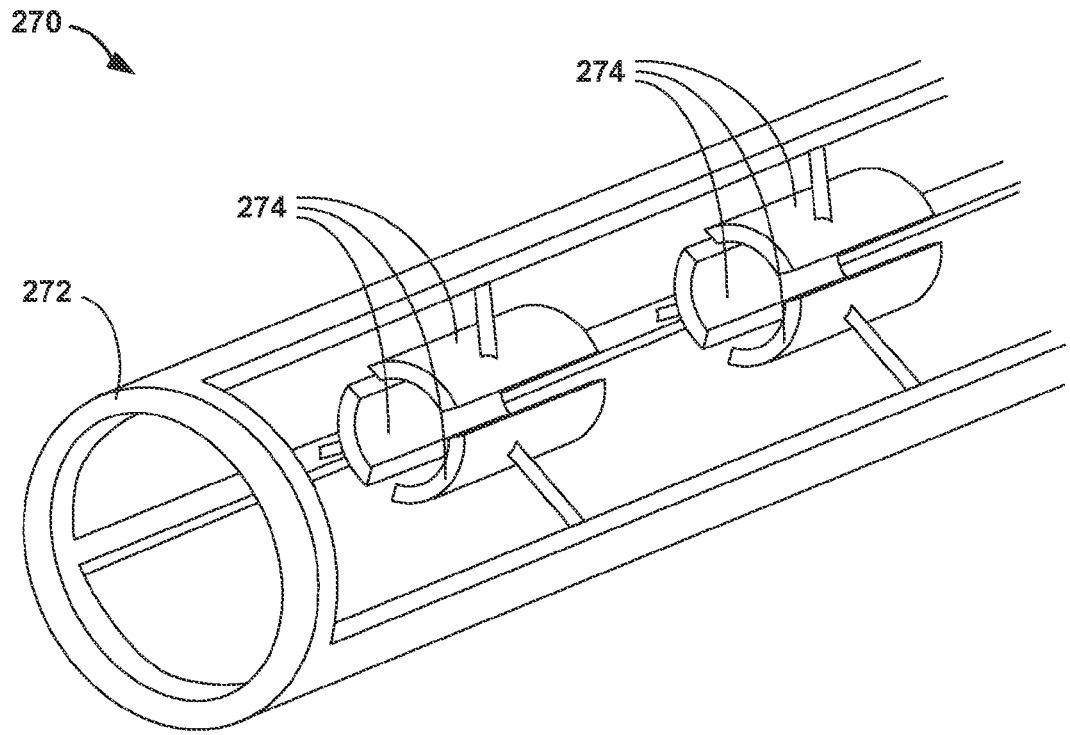
Figure 15B:
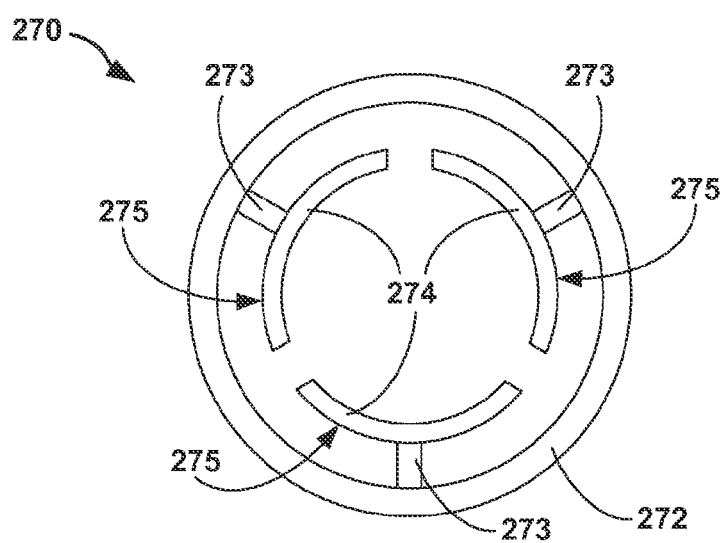

Conductive element 270 of FIGS. 15A-15B comprises a frame element 272 that maintains the relative positions of the portions of the conductive element configured to form electrode segments for a medical lead.

As shown in FIGS. 15A-15B, conductive element 270 of FIGS. 15A-15B comprises frame element 272 that maintains the relative positions of portions 274 of the conductive element configured to form electrode segments for a medical lead. Conductive element 270 is configured to facilitate mechanical and electrical separation of different portions of conductive element 270 to form two or more electrode segments for a medical lead. Specifically, conductive element 270 includes frame element 272 configured to be removed that connects circumferential portions 274 configured to form the electrode segments for the medical lead. Circumferential portions 274 form exposed outer surfaces 275 (FIG. 15B) suitable for stimulation and/or sensing functions of a medical lead.

Circumferential portions 274 configured to form the electrode segments for the medical lead are configured to be substantially congruent with an outer surface of the lead body, whereas frame element 272 is configured to extend outwardly beyond an outer surface of the lead body. Conductive element 270 may be secured within a mold, such as mold 207 (FIG. 10A), by holding frame element 272 prior to injecting material into the mold to form an elongated lead body. In this manner, frame element 272 may facilitate not only maintaining position of circumferential portions 274 relative to each other, but also the absolute positions of circumferential portions 274 within the mold.

In the specific example of conductive element 270, each frame element 272 connects each circumferential portion 274 to each other via posts 273. Posts 273 connect to outer surfaces 275 of circumferential portions 274 configured to form the electrode segments for the medical lead, but not on the edges of the outer surfaces 275. In this manner, after removing frame element 272 from conductive element 270, e.g., by cutting, bending fatigue posts 273 or otherwise, the former attachment points between frame element 272 and circumferential portions 274 may be smoothed, e.g., by grinding, sanding, burnishing and/or polishing without damaging the lead body. It may be important to smooth outer surfaces 275 to prevent concentration of electrical charges during electrical stimulation of the medical lead.

FIGS. 16-23 illustrate exemplary assemblies 280, 290, 300, 310, 320, 330, 340, and 350, each assembly including a set of electrode segments held in a circular arrangement by one or more insulative elements, each of the assemblies being suitable for securing its set of electrode segments in a circular or ring arrangement within a mold during manufacturing of a medical lead. Assemblies 280, 290, 300, 310, 320, 330, 340, and 350 can be used during molding of a medical lead as described with respect to FIGS. 10A-10C in place of the conductive elements from which material can be removed to form two or more electrode segments. In contrast to the techniques described with respect to FIGS. 10A-10C, because assemblies 280, 290, 300, 310, 320, 330, 340, and 350 include electrode segments separated by one of more insulative elements, no cutting is required following the molding of the lead body in order to electrically separate the electrode segments. Rather, the insulative connective pieces may stay in place. For brevity, because the techniques connecting conductors to the electrode segments and the molding of a lead body for a medical lead including one or more of assemblies 280, 290, 300, 310, 320, 330, 340, and 350 is substantially similar to the techniques described with respect to FIGS. 10A-10C, those techniques are not repeated with respect to assemblies 280, 290, 300, 310, 320, 330, 340, and 350.

Assemblies 280, 290, 300, 310, 320, 330, 340, and 350 of FIGS. 16-23 are each formed by holding the electrode segments in the circular arrangement and overmolding the at least one insulative element on the electrode segments held in the circular arrangement. Assemblies 280, 300, 320, and 330 of FIGS. 16, 18, 20, and 21A-21B each include a plurality of insulative elements, each of the plurality of insulative element extending between two adjacent electrode segments of the electrode segments in the ring arrangement. In contrast, assemblies 290, 310, 340, and 350 of FIGS. 17, 19, 22, and 23 each include a single insulative element that is a unitary component holding all of the electrode segments in position relative to one another.

Figure 16:
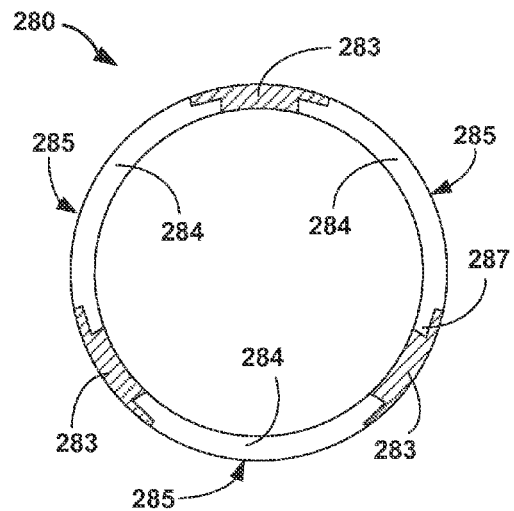
FIGS. 16-23 illustrate exemplary assemblies including a set of electrode segments held in a circular arrangement by one or more insulative elements, each of the assemblies being suitable for securing its set of electrode segments within a mold during manufacturing of a medical lead.

As shown in FIG. 16, assembly 280 includes a set of electrode segments 284 held in a circular arrangement by a set of insulative elements 283. Specifically, assembly 280 includes insulative elements 283 alternating with electrode segments 284 about the circular arrangement. Electrode segments 284 form exposed outer surfaces 285 suitable for stimulation and/or sensing functions of a medical lead.

Electrode segments 284 and insulative elements 283 are configured to be substantially congruent with an outer surface of the lead body. In addition, the inner circumferential surfaces of electrode segments 284 and insulative elements 283 are substantially congruent one another and form a substantially circular inner surface for assembly 280. Insulative elements 283 facilitate maintaining position of electrode segments 284 relative to each other during molding of a lead body. In addition, the entirety of assembly 280 may be secured within the mold for overmolding a lead body, e.g., by being clamped between two halves of the mold to maintain the absolute position of electrode segments 284 within the mold.

In the specific example of assembly 280, each insulative element 283 spans two adjacent electrode segments 284. Each insulative element 283 touches an inner edge of the adjacent electrode segments 284. Further, each electrode segment 284 includes two protrusions having concave features that secure the electrode segment to the lead body following formation of the lead body in that the concave features are embedded in the lead body. For reference, one protrusion is labeled with reference numeral 287 in FIG. 16.

Forming assembly 280 may include holding the electrode segments 284 in a circular arrangement within a mold and overmolding insulative elements 283 on the electrode segments 284. In some examples, electrode segments 284 may include protrusions that extend into the mold for securing the electrode segments within the mold prior to overmolding insulative elements 283. Such protrusions may later be removed. In other examples, electrode segments 284 may be held within a mold used to form insulative elements by other techniques including, e.g., with adhesive or suction.

In some examples, each insulative element 283 may define a width (not shown) that is substantially equal to the width of the electrode segments 284 as measured in the longitudinal direction of a lead body. In other examples, each insulative element 283 may define a width (not shown) that is substantially less than the width of electrode segments 284 as measured in the longitudinal direction of a lead body. In some examples, such insulative elements may be approximately centered relative to the electrode segments 284 in the longitudinal direction of a lead body.

Figure 17:
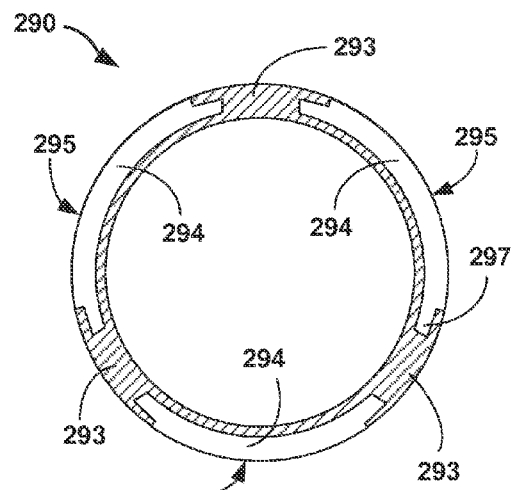

As shown in FIG. 17, assembly 290 includes a set of electrode segments 294 held in a circular arrangement by a unitary insulative element 293. On its outer circumferential surface, assembly 290 includes unitary insulative element 293 alternating with electrode segments 294 about the circular arrangement. Electrode segments 294 form exposed outer surfaces 295 suitable for stimulation and/or sensing functions of a medical lead.

Electrode segments 294 and unitary insulative element 293 are configured to be substantially congruent with an outer surface of the lead body. In addition, unitary insulative element 293 extends between exposed outer surfaces 295 of electrode segments 294 and forms a substantially circular inner surface for assembly 290. Unitary insulative element 293 facilitates maintaining position of electrode segments 294 relative to each other during molding of a lead body. In addition, the entirety of assembly 290 may be secured within the mold for overmolding a lead body, e.g., by being clamped between two halves of the mold to maintain the absolute position of electrode segments 294 within the mold.

In the specific example of assembly 290, each electrode segment 294 includes two protrusions having concave features that secure the electrode segment to unitary insulative element 293 and to the lead body following formation of the lead body. For reference, one protrusion is labeled with reference numeral 297 in FIG. 17.

Forming assembly 290 may include holding the electrode segments 294 in a circular arrangement within a mold and overmolding unitary insulative element 293 on electrode segments 294. In some examples, electrode segments 294 may include protrusions that extend into the mold for securing the electrode segments within the mold prior to overmolding unitary insulative element 293. Such protrusions may later be removed. In other examples, electrode segments 294 may be held within a mold used to form insulative elements by other techniques including, e.g., with adhesive or suction.

In some examples, unitary insulative element 293 may define a width (not shown) that is substantially equal to the width of the electrode segments 294 as measured in the longitudinal direction of a lead body. In other examples, unitary insulative element 293 may define a width (not shown) that is substantially less than the width of electrode segments 294 as measured in the longitudinal direction of a lead body. In some examples, such insulative elements may be approximately centered relative to the electrode segments 294 in the longitudinal direction of a lead body.

Figure 18:
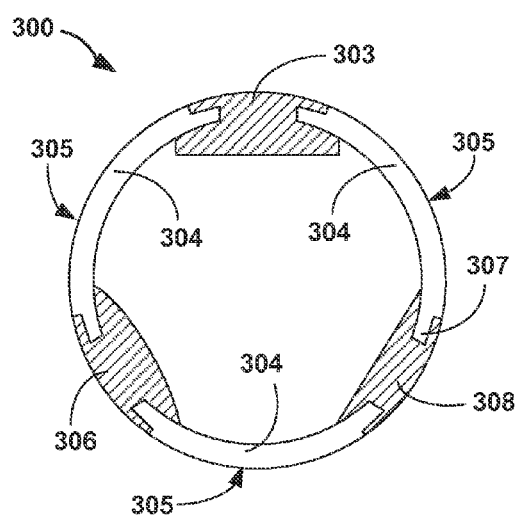

As shown in FIG. 18, assembly 300 includes a set of electrode segments 304 held in a circular arrangement by a set of insulative elements 303, 306, and 308. Electrode segments 304 form exposed outer surfaces 305 suitable for stimulation and/or sensing functions of a medical lead. Assembly 300 includes insulative elements 303, 306, 308 alternating with electrode segments 304 about the circular arrangement. Each of insulative elements 303, 306, 308 is functionally similar, and represents an example configuration of an insulative element suitable for use holding electrode segments 304 in a circular arrangement.

Electrode segments 304 and insulative elements 303, 306, 308 are configured to be substantially congruent with an outer surface of a lead body when assembly 300 is included as part of a medical lead. Insulative elements 303, 306, 308 extend beyond the inner circumferential surfaces of electrode segments 304. Insulative element 303 provides a convex interior surface with three substantially flat sides. Insulative element 306 provides a convex curved interior surface, whereas insulative element 308 provides a substantially flat interior surface. Insulative elements 303, 306, 308 each provide a different example of an insulative element suitable for alternating with electrode segments within a circular arrangement. As such, insulative elements 303, 306, 308 may be combined in any manner within an assembly to hold a set of electrode segments 304 in a circular arrangement although it may be most common to include substantially similar insulative elements within a single assembly including a set of electrode segments 304 in a ring arrangement.

Insulative elements 303, 306, 308 facilitate maintaining position of electrode segments 304 relative to each other during molding of a lead body. In addition, the entirety of assembly 300 may be secured within the mold for overmolding a lead body, e.g., by being clamped between two halves of the mold to maintain the absolute position of electrode segments 304 within the mold.

In the specific example of assembly 300, each insulative element 303, 306, 308 spans two adjacent electrode segments 304. Each insulative element 303, 306, 308 touches an inner edge of the adjacent electrode segments 304. Further, each electrode segment 304 includes two protrusions having concave features that secure the electrode segment to the lead body following formation of the lead body. For reference, one protrusion is labeled with reference numeral 307 in FIG. 18.

Forming assembly 300 may include holding the electrode segments 304 in a circular arrangement within a mold and overmolding insulative elements 303, 306, 308 on the electrode segments 304. In some examples, electrode segments 304 may include protrusions that extend into the mold for securing the electrode segments within the mold prior to overmolding insulative elements 303, 306, 308. Such protrusions may later be removed. In other examples, electrode segments 304 may be held within a mold used to form insulative elements by other techniques including, e.g., with adhesive or suction.

In some examples, each insulative element 303, 306, 308 may define a width (not shown) that is substantially equal to the width of the electrode segments 304 as measured in the longitudinal direction of a lead body. In other examples, each insulative element 303, 306, 308 may define a width (not shown) that is substantially less than the width of electrode segments 304 as measured in the longitudinal direction of a lead body. In some examples, such insulative elements may be approximately centered relative to the electrode segments 304 in the longitudinal direction of a lead body.

Figure 19:
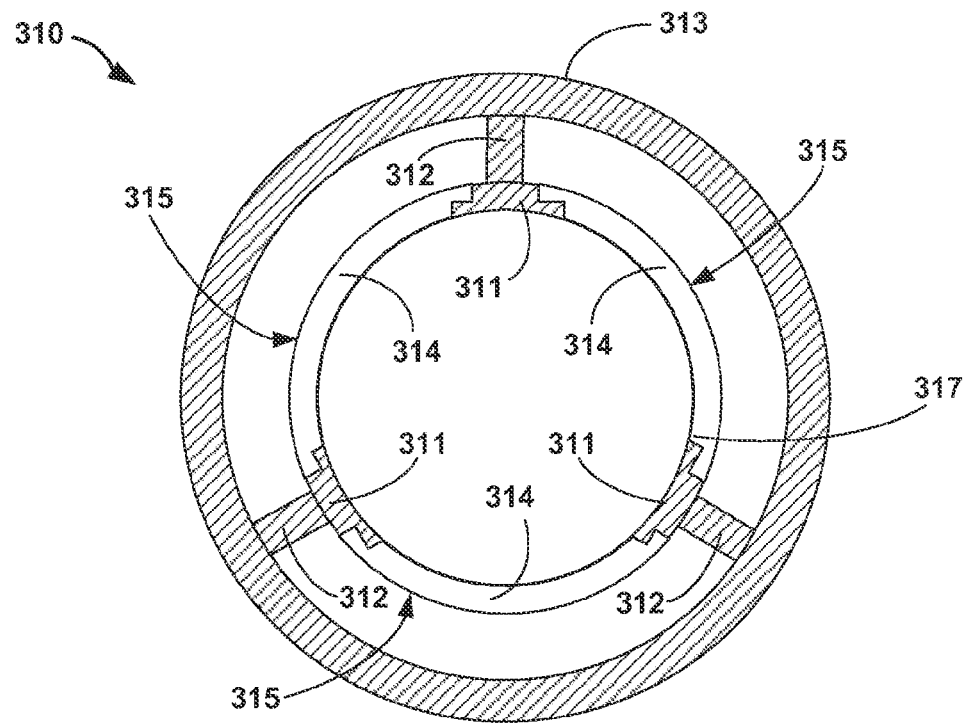

As shown in FIG. 19, assembly 310 includes a set of electrode segments 314 held in a circular arrangement by an insulative element 313. Insulative element 313 is a unitary component that extends between electrode segments 314 and forms a frame surrounding of the ring arrangement. Insulative element 313 includes posts 312 that may be cut to release electrode segments 314 from the frame element. As shown, posts 312 are located directly on the stimulating surface area of the electrode segments. In other examples, posts 312 may be located in the slot in between or at the end of the electrode segments. In other examples, post 312 may be pre-glued or pre-welded posts on the electrode segments, and removed after injection molding of the distal end.

Electrode segments 314 form exposed outer surfaces 315 suitable for stimulation and/or sensing functions of a medical lead. Insulative element 313 alternates with electrode segments 314 about an outer surface of the circular arrangement.

Electrode segments 314 are configured to be substantially congruent with an outer surface of the lead body, whereas the frame configuration of insulative element 313 is configured to extend outwardly beyond an outer surface of the lead body. Assembly 310 may be secured within a mold, such as mold 207 (FIG. 10A), by holding insulative element 313 prior to injecting material into the mold to form an elongated lead body. In this manner, insulative element 313 may facilitate not only maintaining position of electrode segments 314 relative to each other, but also the absolute positions of electrode segments 314 within the mold. After forming the lead body, portions of insulative element 313 that extend beyond an outer surface of the lead body may be removed, e.g., by cutting posts 312 and thereby leaving three separate insulative portions 311 alternating with electrode segments 314 within the ring arrangement.

In the specific example of assembly 310, each electrode segment 314 includes two protrusions having concave features that secure the electrode segment to insulative element 313 and to the lead body following formation of the lead body. For reference, one protrusion is labeled with reference numeral 317 in FIG. 19.

Forming assembly 310 may include holding the electrode segments 314 in a circular arrangement within a mold and overmolding insulative element 313 on electrode segments 314. In some examples, electrode segments 314 may include protrusions that extend into the mold for securing the electrode segments within the mold prior to overmolding insulative element 313. Such protrusions may later be removed. In other examples, electrode segments 314 may be held within a mold used to form insulative elements by other techniques including, e.g., with adhesive or suction.

Figure 20:
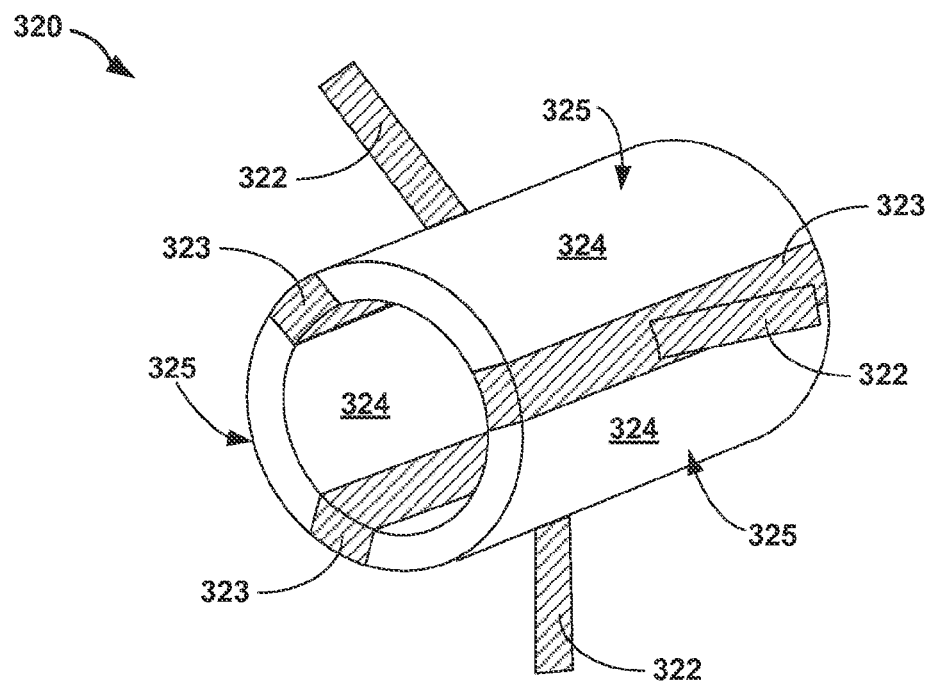

As shown in FIG. 20, assembly 320 includes a set of electrode segments 324 held in a circular arrangement by an insulative element 323. Insulative elements 323 each extend between two adjacent electrode segments 324 within the circular arrangement. Insulative elements 323 alternate with electrode segments 324 about an outer surface of the circular arrangement. Electrode segments 324 form exposed outer surfaces 325 suitable for stimulation and/or sensing functions of a medical lead.

Electrode segments 324 are configured to be substantially congruent with an outer surface of the lead body, whereas posts 322 of insulative elements 323 are configured to extend outwardly beyond an outer surface of the lead body.

Assembly 320 may be secured within a mold, such as mold 207 (FIG. 10A), by holding insulative elements 323 prior to injecting material into the mold to form an elongated lead body. In this manner, insulative elements 323 may facilitate not only maintaining position of electrode segments 324 relative to each other, but also the absolute positions of electrode segments 324 within the mold. After forming the lead body, portions of insulative elements 323 that extend beyond an outer surface of the lead body may be removed, e.g., by cutting posts 322.

As shown, posts 322 are located in the slot in between or at the end of the electrode segments. In other examples, posts 322 may be located in any other position that facilitates holding assembly 320 within a mold for forming a lead body.

Forming assembly 320 may include holding the electrode segments 324 in a circular arrangement within a mold and overmolding insulative elements 323 on electrode segments 324. In some examples, electrode segments 324 may include protrusions that extend into the mold for securing the electrode segments within the mold prior to overmolding insulative elements 323. Such protrusions may later be removed. In other examples, electrode segments 324 may be held within a mold used to form insulative elements by other techniques including, e.g., with adhesive or suction.

Figure 21B:
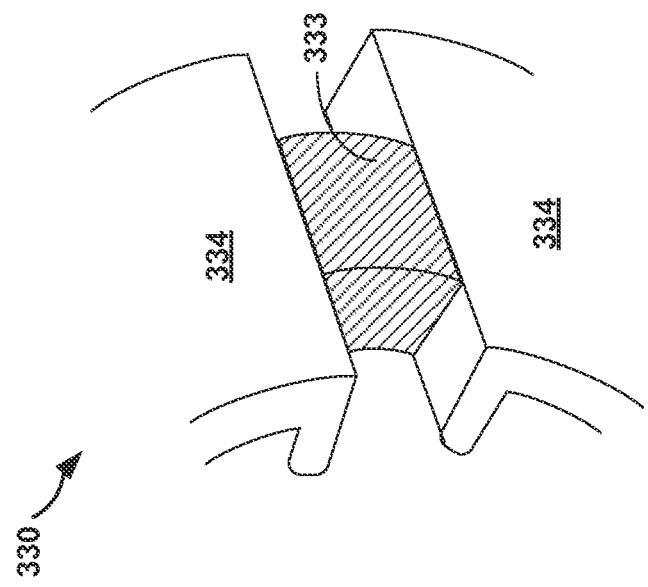
Figure 21A:
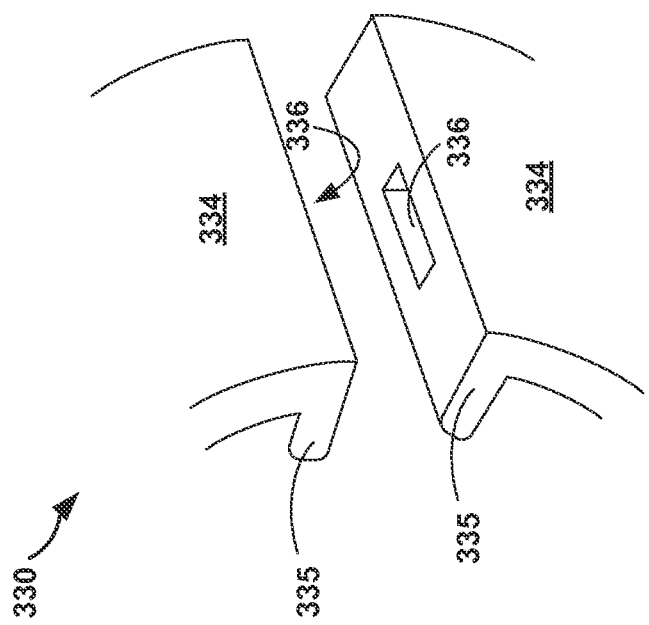

FIGS. 21A-22B illustrate portions of assembly 330, including a set of electrode segments 334 held in a circular arrangement by insulative elements 333. FIG. 21A illustrate two adjacent electrode segments 334, whereas FIG. 21B illustrates the two adjacent electrode segments 334 in an assembly with a mating insulative element 333. While the entirety of assembly 330 is not shown, the ring arrangement of assembly 330 is similar to that of assembly 280 in that on its outer circumferential surface, assembly 330 includes insulative elements 333 (one of which is shown) alternating with electrode segments 334 about the circular arrangement. Electrode segments 334 form exposed outer surfaces suitable for stimulation and/or sensing functions of a medical lead.

Electrode segments 334 and insulative elements 333 are configured to be substantially congruent with an outer surface of the lead body. In addition, insulative elements 333 extend between exposed outer surfaces 335 of electrode segments 334. Insulative elements 333 facilitate maintaining position of electrode segments 334 relative to each other during molding of a lead body. In addition, the entirety of assembly 330 may be secured within the mold for overmolding a lead body, e.g., by being clamped between two halves of the mold to maintain the absolute position of electrode segments 334 within the mold.

In the specific example of assembly 330, each electrode segment 334 is a folded metal element including two protrusions 335 having concave features that secure the electrode segment to insulative elements 333 and to the lead body following formation of the lead body. The concave features of protrusions 335 include through-hole 336. Each through-hole 336 extends in a circumferential direction through its protrusions 335.

Forming assembly 330 may include holding the electrode segments 334 in a circular arrangement within a mold and overmolding insulative elements 333 on electrode segments 334 such that insulative elements 333 engage through-holes 336. In some examples, electrode segments 334 may include protrusions that extend into the mold for securing the electrode segments within the mold prior to overmolding insulative elements 333. Such protrusions may later be removed. In other examples, electrode segments 334 may be held within a mold used to form insulative elements by other techniques including, e.g., with adhesive or suction.

Insulative elements 333 may define a width that is substantially less than the width of electrode segments 334 as measured in the longitudinal direction of a lead body. Insulative elements 333 may be approximately centered relative to electrode segments 334 in the longitudinal direction of a lead body. In other examples, insulative elements otherwise similar to insulative elements 333 may define a width that is substantially equal to the width of the electrode segments 334 as measured in the longitudinal direction of a lead body.

Figure 22:
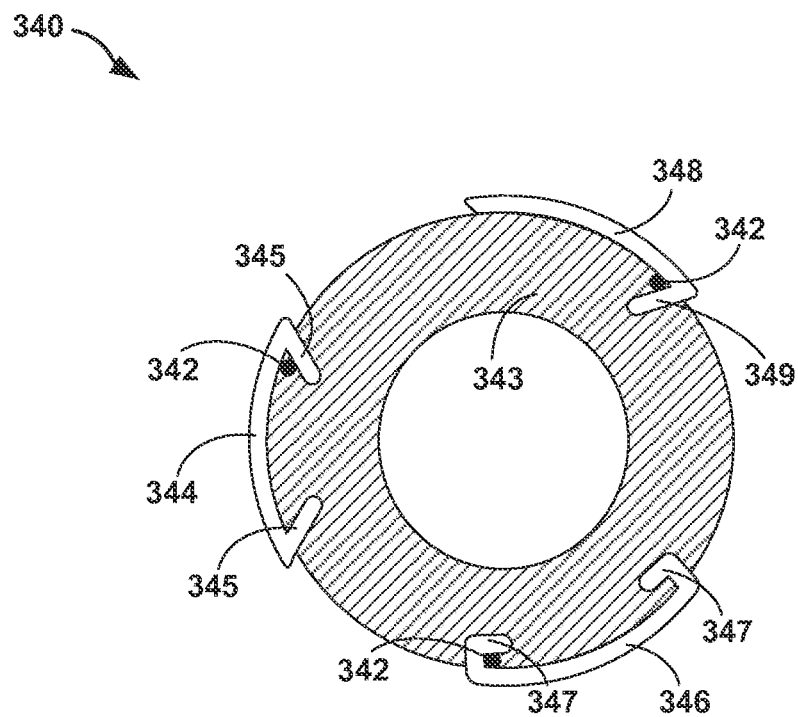

FIG. 22 illustrates portions of assembly 340 including set of electrode segments 344, 346, 348 held in a circular arrangement by unitary insulative element 343. On its outer circumferential surface, assembly 340 includes unitary insulative element 343 alternating with electrode segments 344, 346, 348 about the circular arrangement. Electrode segments 344, 346, 348 form exposed outer surfaces suitable for stimulation and/or sensing functions of a medical lead. Each of electrode segments 344, 346, 348 is functionally similar, and represents an example configuration of an electrode segment.

Electrode segments 344, 346, 348 and unitary insulative element 343 are configured to be substantially congruent with an outer surface of the lead body. In addition, unitary insulative element 343 extends between exposed outer surfaces 345 of electrode segments 344, 346, 348 and forms a substantially circular inner surface for assembly 340. Unitary insulative element 343 facilitates maintaining position of electrode segments 344, 346, 348 relative to each other during molding of a lead body. In this manner, insulative element 343 may facilitate not only maintaining position of electrode segments 344, 346, 348 relative to each other, but also the absolute positions of electrode segments 344, 346, 348 within the mold.

In the specific example of assembly 340, each electrode segment 344, 346, 348 is a folded metal element including one or two protrusions 345, 347, 349 having concave features that secure the electrode segment to unitary insulative element 343 and to the lead body following formation of the lead body. Electrode segment 344 includes two protrusions 345. Protrusions 345 are each formed by a single fold of the metal element forming electrode segment 344. Each of protrusions 345 is suitable for electrically connecting conductor 342 to electrode segment 344 to provide an electrical connection to a proximal end of a medical lead although only one of protrusions 345 is connected to conductor 342. Specifically, one of protrusions 345 pinches conductor 342 to electrically connect conductor 342 to electrode segment 344. The concave features of protrusions 345 may include a through-hole.

Electrode segment 346 includes two protrusions 347. Protrusions 347 are each formed by two folds of the metal element forming electrode segment 346. Each of protrusions 347 is suitable for electrically connecting conductor 342 to electrode segment 346 to provide an electrical connection to a proximal end of a medical lead although only one of protrusions 347 is connected to conductor 342. Specifically, one of protrusions 347 pinches conductor 342 to electrically connect conductor 342 to electrode segment 346. The concave features of protrusions 347 may include a through-hole.

Electrode segment 348 includes a single protrusion 349. Protrusion 349 is formed by a single fold of the metal element forming electrode segment 348. Protrusion 349 pinches conductor 342 to electrically connect conductor 342 to electrode segment 348 to provide an electrical connection to a proximal end of a medical lead. The concave features of protrusion 349 may include a through-hole.

Forming assembly 340 may include holding the electrode segments 344, 346, 348 in a circular arrangement within a mold and overmolding unitary insulative element 343 on electrode segments 344, 346, 348 such that unitary insulative element 343 engage protrusions 345. In some examples, electrode segments 344, 346, 348 may include protrusions that extend into the mold for securing the electrode segments within the mold prior to overmolding unitary insulative element 343. Such protrusions may later be removed. In other examples, electrode segments 344, 346, 348 may be held within a mold used to form insulative elements by other techniques including, e.g., with adhesive or suction.

Unitary insulative element 343 may define a width that is substantially less than the width of electrode segments 344, 346, 348 as measured in the longitudinal direction of a lead body. Unitary insulative element 343 may be approximately centered relative to electrode segments 344, 346, 348 in the longitudinal direction of a lead body. In other examples, unitary insulative element 343 may define a width that is substantially equal to the width of the electrode segments 344, 346, 348 as measured in the longitudinal direction of a lead body.

Figure 23:
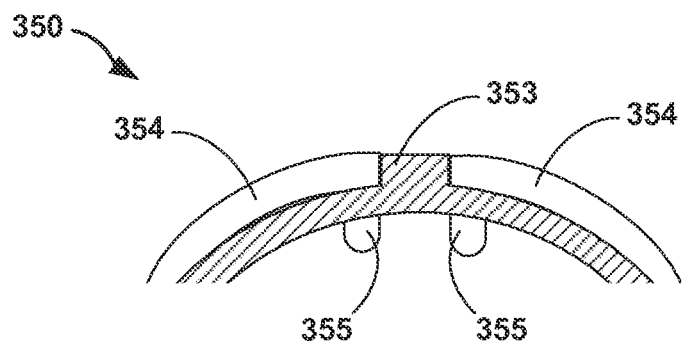

FIG. 23 illustrates portions of assembly 350 including set of electrode segments 354 held in a circular arrangement by unitary insulative element 353. FIG. 23 illustrates two adjacent electrode segments 354 in an assembly with insulative element 353. While the entirety of assembly 350 is not shown, the ring arrangement of assembly 350 is similar to that of assembly 290 in that on its outer circumferential surface, assembly 350 includes unitary insulative element 353 (a portion of which is shown) alternating with electrode segments 354 about the circular arrangement. Electrode segments 354 form exposed outer surfaces suitable for stimulation and/or sensing functions of a medical lead.

Electrode segments 354 and unitary insulative element 353 are configured to be substantially congruent with an outer surface of the lead body. In addition, unitary insulative element 353 extends between exposed outer surfaces of electrode segments 354 and forms a substantially circular inner surface for assembly 350. Unitary insulative element 353 facilitates maintaining position of electrode segments 354 relative to each other during molding of a lead body. In this manner, insulative element 353 may facilitate not only maintaining position of electrode segments 354 relative to each other, but also the absolute positions of electrode segments 354 within the mold.

In the specific example of assembly 350, each electrode segment 354 is a folded metal element including two protrusions 355 having concave features that secure the electrode segment to unitary insulative element 353 and to the lead body following formation of the lead body. The concave features of protrusions 355 may include a through-hole. Protrusions 355 define a width that is substantially less than the width of unitary insulative element 353 as measured in the longitudinal direction of a lead body.

Forming assembly 350 may include holding the electrode segments 354 in a circular arrangement within a mold and overmolding unitary insulative element 353 on electrode segments 354 such that unitary insulative element 353 engage protrusions 355. In some examples, electrode segments 354 may include protrusions that extend into the mold for securing the electrode segments within the mold prior to overmolding unitary insulative element 353. Such protrusions may later be removed. In other examples, electrode segments 354 may be held within a mold used to form insulative elements by other techniques including, e.g., with adhesive or suction.

Unitary insulative element 353 may define a width that is substantially less than the width of electrode segments 354 as measured in the longitudinal direction of a lead body. Unitary insulative element 353 may be approximately centered relative to electrode segments 354 in the longitudinal direction of a lead body. In other examples, unitary insulative element 353 may define a width that is substantially equal to the width of the electrode segments 354 as measured in the longitudinal direction of a lead body.

FIGS. 24A-24E illustrate techniques for manufacturing medical lead 400 including overmolding protrusions 395 electrode segments 382 to facilitate holding electrode segments 382 in a circular arrangement during molding of lead body 418.

Figure 24A:
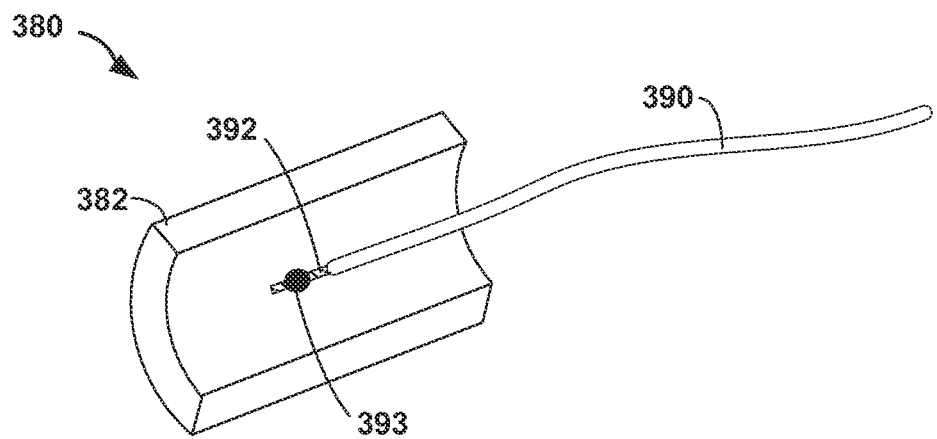

As shown in FIG. 24A, electrode segment 382 is first electrically connected to insulated conductor 390 via connection 393 to form assembly 380. Connection 393 may comprise, e.g., soldered, welded, or brazing between an interior surface of electrode segment 382 and exposed conductor 392 of insulated conductor 390. Similar techniques may be used to electrically connect conductors to any of the other electrode segments or conductive elements configured to provide electrode segments disclosed herein prior to molding of a lead body.

Figure 24B:
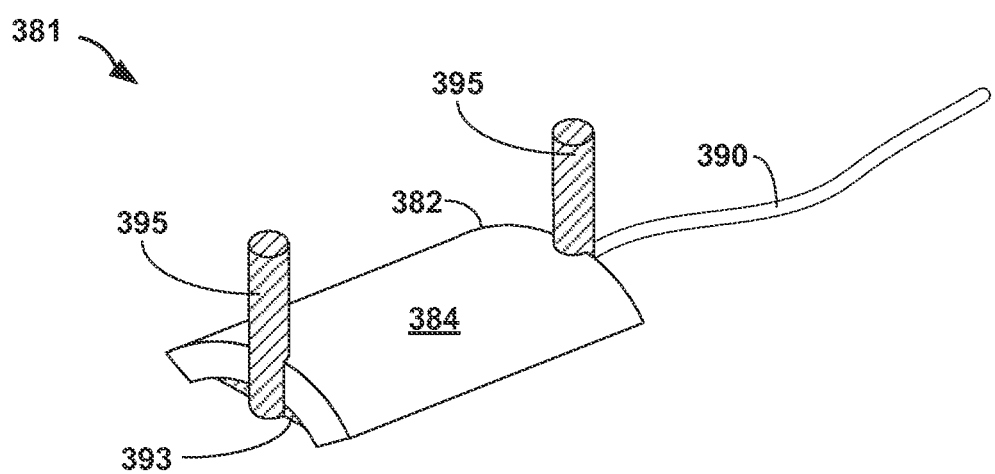

Next, as shown in FIG. 24B, insulative element 393, which includes two posts 395, is overmolded on assembly 380 to form assembly 381. Insulative element 393 envelops connection 393 and the distal end of insulated conductor 390. Electrode segment 382 forms an exposed outer surface 384 suitable for stimulation and/or sensing functions of a medical lead.

Figure 24C:
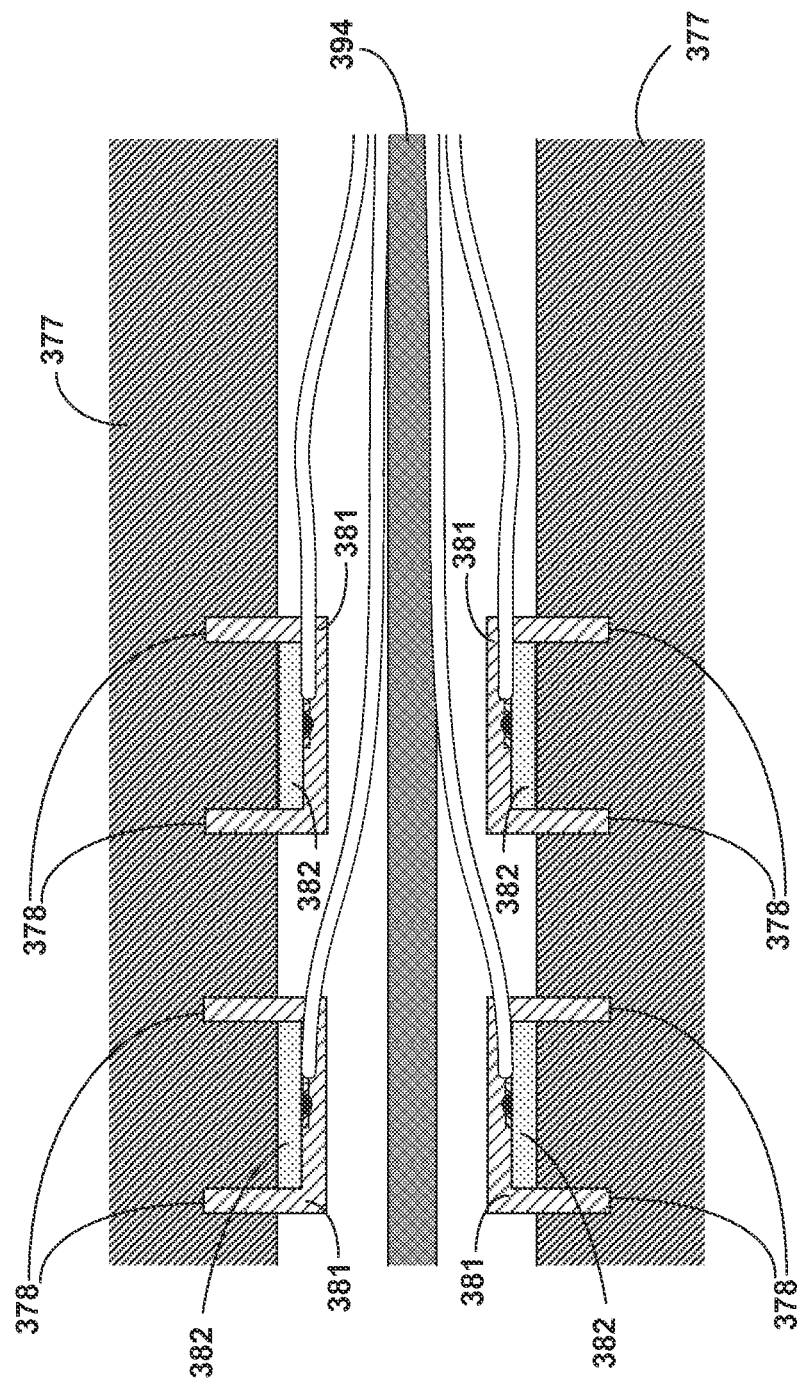

As shown in FIG. 24C, posts 395 are configured to extend outwardly beyond outer surface 384 to facilitate securing assembly 381 during a molding operation to form lead body 418. More specifically, electrode segments 382 are configured to be substantially congruent with an outer surface of the lead body, whereas posts 395 of insulative elements 393 are configured to extend outwardly beyond an outer surface of the lead body. As shown, posts 395 are located in the slot in between or at the end of the electrode segments. In other examples, posts 395 may be located directly on the stimulating surface area of the electrode segments, such as attached through a perpendicular hole inside the electrode segments towards the insulation material underneath the electrode segments. In other examples, post 395 may be pre-glued or pre-welded posts on the electrode segments, and removed after injection molding of the distal end.

Assemblies 381 are secured within mold 377 by positioning posts 395 of insulative elements 393 into ports 378 of mold 377. Ports 378 are arranged to hold electrode segments 382 in a circular arrangement within mold 377. Stylet 394 is also inserted into mold 377 prior to injecting material into mold 377.

Once assemblies 381 and stylet 394 are positioned within mold 377, a lead body material is injected into mold 377 to form lead body 418 as shown in FIG. 24D. Then posts 395 are removed such that electrode segments 382 are configured to be substantially congruent with lead body 418 as shown in FIG. 24E.

In the example of medical lead 400, medical lead 400 includes two sets of electrode segments 382, each set within a circular arrangement, as well as one set of tip electrode segments 411. Tip electrode segments 411 are similar to electrode segments 382 except that tip electrode segments 411 form a rounded distal surface for medical lead 400.

In the example of medical lead 400, each circular arrangement of electrode segments 380 includes three equally spaced electrode segments 380. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

In some examples, lead body 418 and medical lead 400 may have a substantially circular cross-sectional shape, although other cross-sectional shapes may also be used. In some examples, medical lead 400 may be included in a system with a stimulation generator configured to deliver electrical stimulation via a selected combination of electrode segments 382 and tip electrode segments 411 of medical lead 400. In such a system, the proximal end of medical lead 400 is electrically connected to the stimulation generator, e.g., via a connector or otherwise. In some examples, the stimulation generator may be configured to deliver DBS and medical lead 400 may comprise a DBS lead.

FIGS. 25A-29E illustrate medical leads 430, 450, 470, 490, 510. Each of medical leads 430, 450, 470, 490, 510 includes a set of electrode segments within a circular arrangement, wherein the electrode segments include an exposed outer surface and a protrusion extending into the lead body, the protrusion including concave features that secure the electrode segment to the lead body.

Figure 25A:
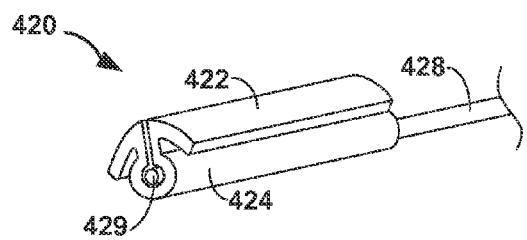
FIGS. 25A-29C illustrate medical leads including a set of electrode segments, each electrode segments including an exposed outer surface and a protrusion extending into the lead body, the protrusion including concave features that secure the electrode segment to the lead body.
Figure 25B:
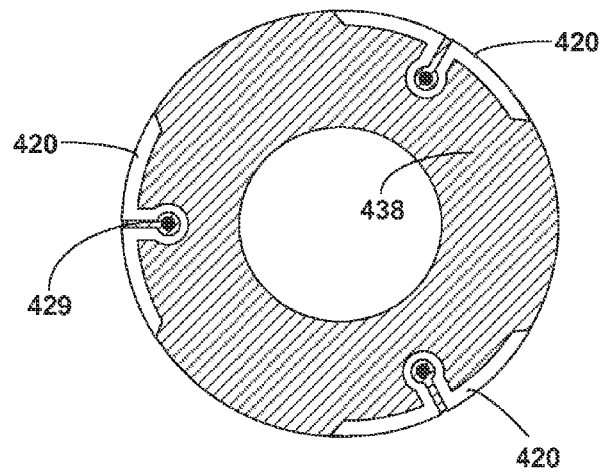
Figure 25C:
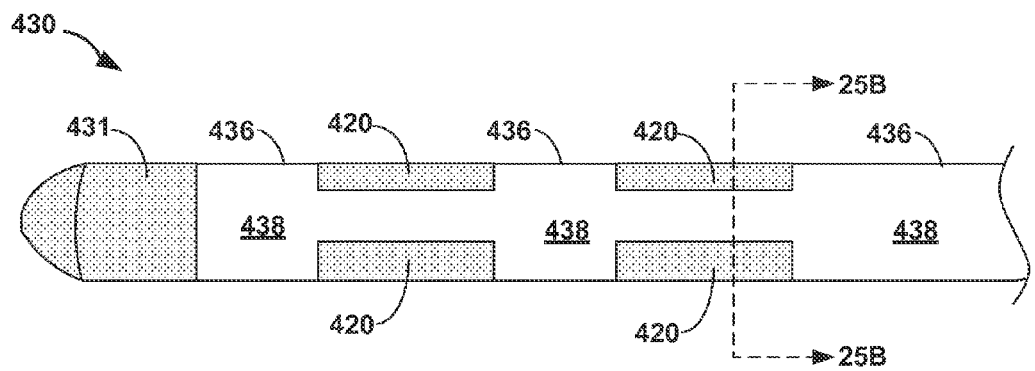

FIGS. 25A-25C illustrate medical lead 430 and its components. More specifically, FIG. 25A illustrates electrode segment 420, which is representative of each of electrode segments 420 within medical lead 430, whereas FIG. 25B illustrates a cross-section of medical lead 430, and FIG. 25C illustrates a side view of medical lead 430. Electrode segment 420 includes protrusion 424, which is configured to extend into lead body 438. As discussed in greater detail below, protrusion 424 includes concave features that secure the electrode segment 420 to lead body 438.

As shown in FIG. 25A, electrode segment 420 includes a top portion forming exposed outer surface 422 and an inner tubular portion forming protrusion 424. Electrode segment 420 is formed from a folded metal element that forms both exposed outer surface 422 and protrusion 424. Exposed outer surface 422 is formed by two portions of the folded metal element and is bisected by the folds of the folded metal element forming electrode segment 420.

Electrode segment 420 is electrically connected to exposed distal end 429 of insulated conductor 428. Distal end 429 of insulated conductor 428 is pinched within the inner tubular portion of protrusion 424 such that distal end 429 of insulated conductor 428 is in electrical contact with electrode segment 420. Many techniques may be used to secure distal end 429 of insulated conductor 428 within the inner tubular portion of protrusion 424 such as mechanical pinching, soldering, welding, brazing, compression fit or other technique.

As shown in FIG. 25C, medical lead 430 includes elongated lead body 438 as well as two sets of electrode segments 420 and a tip electrode 431. Each electrode segment 420 is a separate unitary component. Each set of electrode segments 420 is in a circular arrangement at a common longitudinal position along lead body 438. Medical lead 430 further includes a plurality of conductors 428 (not shown in FIG. 25C) extending within the lead body, each of the conductors being in electrical contact with one of electrode segments 420 or tip electrode 431 and extending to a proximal end of lead body 438. In some examples, medical lead 430 may include a connector at the proximal end of medical lead 430 to electrically connect the connector to electrode segments 420 and tip electrode 431.

As shown in FIG. 25B, the exposed outer surface of each electrode segment 420 is substantially congruent with outer surface 436 of lead body 438. Further, the protrusions 424 (FIG. 25A) provide concave features that secure electrode segment 420 to lead body 438 such that separating one of electrode segments 420 from lead body 438 would require deformation of lead body 438 or the electrode segment 420. Manufacturing of medical lead 430 may include overmolding lead body 438 over electrode segments 420 and insulated conductors 428, e.g., as described with respect to any of medical leads 200, 220 and 400. In some examples, lead body 438 and medical lead 430 may have a substantially circular cross-sectional shape, although other cross-sectional shapes may also be used.

In the example of medical lead 430, medical lead 430 includes two sets of electrode segments 420, each set within a circular arrangement as well as one tip electrode segment 411. Each circular arrangement of electrode segments 430 includes three equally spaced electrode segments 430. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

Figure 26A:
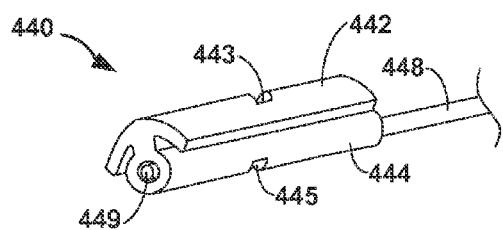
Figure 26B:
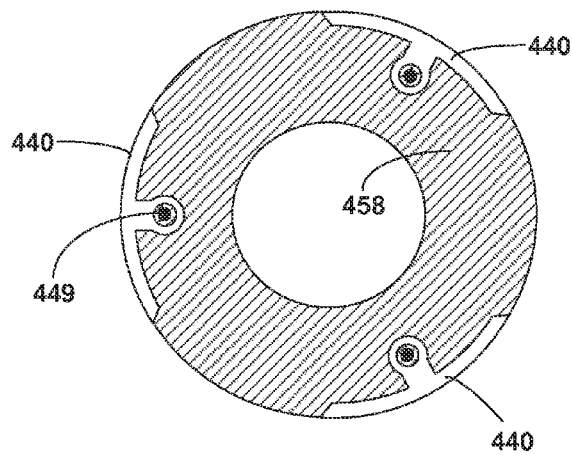
Figure 26C:
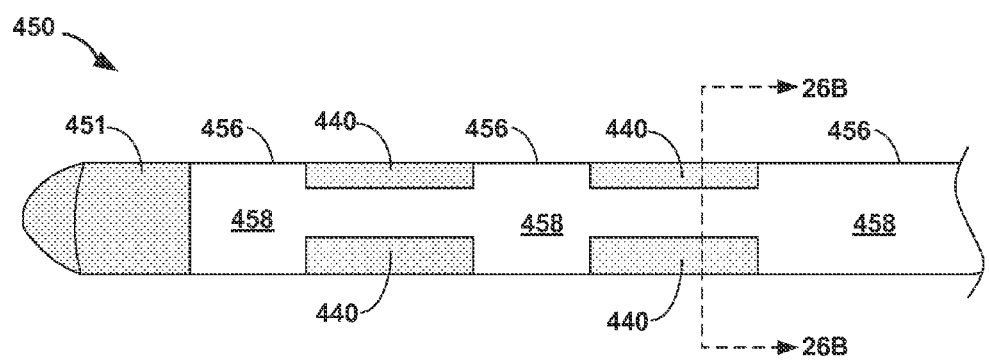

FIGS. 26A-26C illustrate medical lead 450 and its components. FIG. 26A illustrates electrode segment 440, which is representative of each of electrode segments 440 within medical lead 450. FIG. 26B illustrates a cross-section of medical lead 450, and FIG. 26C illustrates a side view of medical lead 450. Electrode segment 440 includes protrusion 444, which is configured to extend into lead body 458. As discussed in greater detail below, protrusion 444 includes concave features that secure the electrode segment 440 to lead body 458.

As shown in FIG. 26A, electrode segment 440 includes a top portion forming exposed outer surface 442 and an inner tubular portion forming protrusion 444.

Electrode segment 440 is electrically connected to exposed distal end 449 of insulated conductor 448. Distal end 449 of insulated conductor 448 is pinched within the inner tubular portion of protrusion 444 such that distal end 449 of insulated conductor 448 is in electrical contact with electrode segment 440. In the example, of FIG. 26A, electrode segment 440 includes a recess 445 in the inner tubular portion forming protrusion 444. Recess 445 may represent a punch or other tool mark used to partially collapse the inner tubular portion forming protrusion 444 in order to pinch and secure distal end 449 of insulated conductor 448 within the inner tubular portion of protrusion 444. As also shown in FIG. 26A, electrode segment 440 further includes a recess 443 in outer surface 442. Recess 443 may also represent a punch or other tool mark used to partially collapse the inner tubular portion forming protrusion 444 in order to secure distal end 449 of insulated conductor 448 is pinched within the inner tubular portion of protrusion 444. In other examples, a single recess punch or tool mark may be used to partially collapse the inner tubular portion forming protrusion 444 in order to pinch and secure distal end 449 of insulated conductor 448 within the inner tubular portion of protrusion 444. Other techniques may also be used to secure distal end 449 of insulated conductor 448 within the inner tubular portion of protrusion 444 such as soldering, welding, brazing, compression fit or other technique.

FIG. 26B illustrates a cross-section of medical lead 450. As shown in FIG. 26B, separating one of electrode segments 440 from lead body 458 would require deformation of lead body 458 or the electrode segment 440 in that protrusion 444 is enveloped by lead body 458.

As shown in FIG. 26C, medical lead 450 includes elongated lead body 458 as well as two sets of electrode segments 440 and a tip electrode 451. Each electrode segment 440 is a separate unitary component. Each set of electrode segments 440 is in a circular arrangement at a common longitudinal position along lead body 458. Medical lead 450 further includes a plurality of conductors 448 (not shown in FIG. 26C) extending within the lead body, each of the conductors being in electrical contact with one of electrode segments 440 or tip electrode 451 and extending to a proximal end of lead body 458. In some examples, medical lead 450 may include a connector at the proximal end of medical lead 450 to electrically connect the connector to electrode segments 440 and tip electrode 451.

As shown in FIG. 26B, the exposed outer surface of each electrode segment 440 is substantially congruent with outer surface 456 of lead body 458. Further, the protrusions 444 (FIG. 26A) provide concave features that secure electrode segment 440 to lead body 458 such that separating one of electrode segments 440 from lead body 458 would require deformation of lead body 458 or the electrode segment 440. Manufacturing of medical lead 450 may include overmolding lead body 458 over electrode segments 440 and insulated conductors 448, e.g., as described with respect to any of medical leads 200, 220 and 400. In some examples, lead body 458 and medical lead 450 may have a substantially circular cross-sectional shape, although other cross-sectional shapes may also be used.

In the example of medical lead 450, medical lead 450 includes two sets of electrode segments 440, each set within a circular arrangement as well as one tip electrode segment 411. Each circular arrangement of electrode segments 450 includes three equally spaced electrode segments 450. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

Figure 27A:
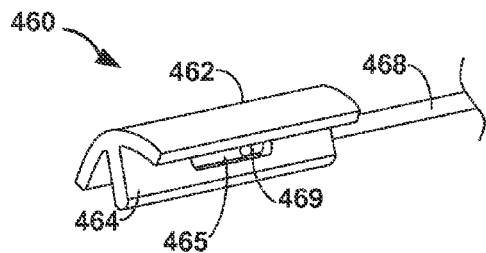
Figure 27B:
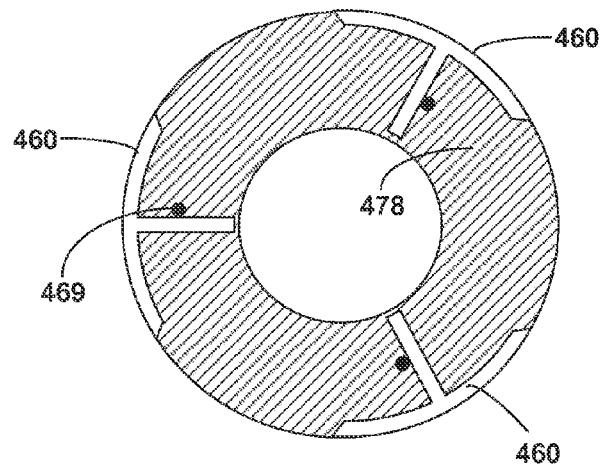
Figure 27C:
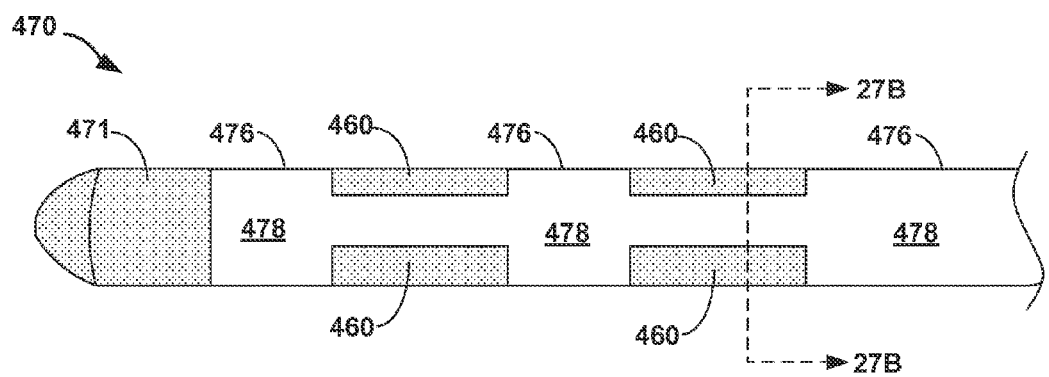

FIGS. 27A-27C illustrate medical lead 470 and its components. More specifically, FIG. 27A illustrates electrode segment 460, which is representative of each of electrode segments 460 within medical lead 470, whereas FIG. 27B illustrates a cross-section of medical lead 470, and FIG. 27C illustrates a side view of medical lead 470. Electrode segment 460 includes protrusion 464, which is configured to extend into lead body 478. As discussed in greater detail below, protrusion 464 includes concave features that secure the electrode segment 460 to lead body 478.

As shown in FIGS. 27A and 27B, electrode segment 460 has a T-shaped profile including a top portion forming exposed outer surface 462 and an inner portion forming protrusion 464. The concave features of protrusion 464 include through-hole 465. Through-hole 465 extends in a circumferential direction through protrusion 464 relative to lead body 478 within medical lead 470.

Electrode segment 460 is electrically connected to exposed distal end 469 of insulated conductor 468. Distal end 469 of insulated conductor 468 extends through through-hole 465 of protrusion 464 such that distal end 469 of insulated conductor 468 is in electrical contact with electrode segment 460. Many techniques may be used to secure distal end 469 of insulated conductor 468 to protrusion 464 such as mechanical pinching, soldering, welding, brazing, compression fit or other technique.

As shown in FIG. 27C, medical lead 470 includes elongated lead body 478 as well as two sets of electrode segments 460 and a tip electrode 471. Each electrode segment 460 is a separate unitary component. Each set of electrode segments 460 is in a circular arrangement at a common longitudinal position along lead body 478. Medical lead 470 further includes a plurality of conductors 468 (not shown in FIG. 27C) extending within the lead body, each of the conductors being in electrical contact with one of electrode segments 460 or tip electrode 471 and extending to a proximal end of lead body 478. In some examples, medical lead 470 may include a connector at the proximal end of medical lead 470 to electrically connect the connector to electrode segments 460 and tip electrode 471.

As shown in FIG. 27B, the exposed outer surface of each electrode segment 460 is substantially congruent with outer surface 476 of lead body 478. Further, the protrusions 464 (FIG. 27A) provide concave features that secure electrode segment 460 to lead body 478 such that separating one of electrode segments 460 from lead body 478 would require deformation of lead body 478 or the electrode segment 460. Manufacturing of medical lead 470 may include overmolding lead body 478 over electrode segments 460 and insulated conductors 468, e.g., as described with respect to any of medical leads 200, 220 and 400. In some examples, lead body 478 and medical lead 470 may have a substantially circular cross-sectional shape, although other cross-sectional shapes may also be used.

Medical lead 470 includes two sets of electrode segments 460, each set within a circular arrangement as well as one tip electrode segment 411. Each circular arrangement of electrode segments 470 includes three equally spaced electrode segments 470. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

Figure 28A:
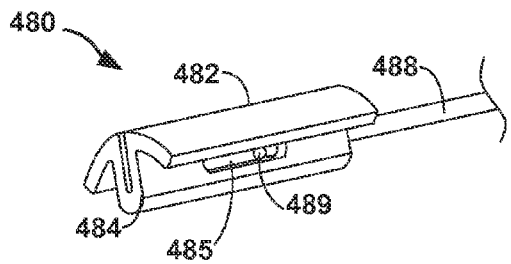
Figure 28B:
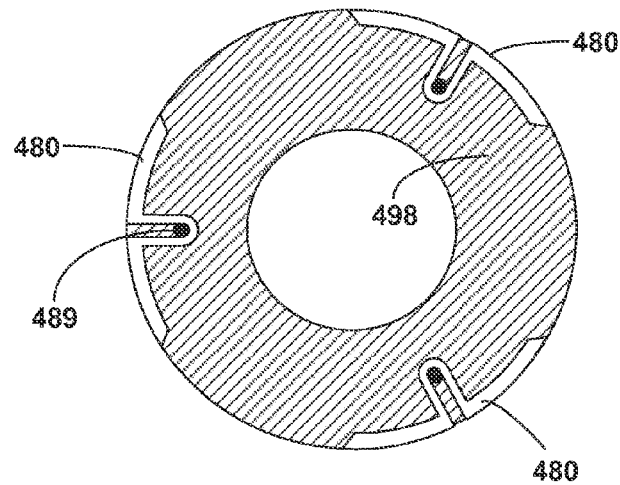
Figure 28C:
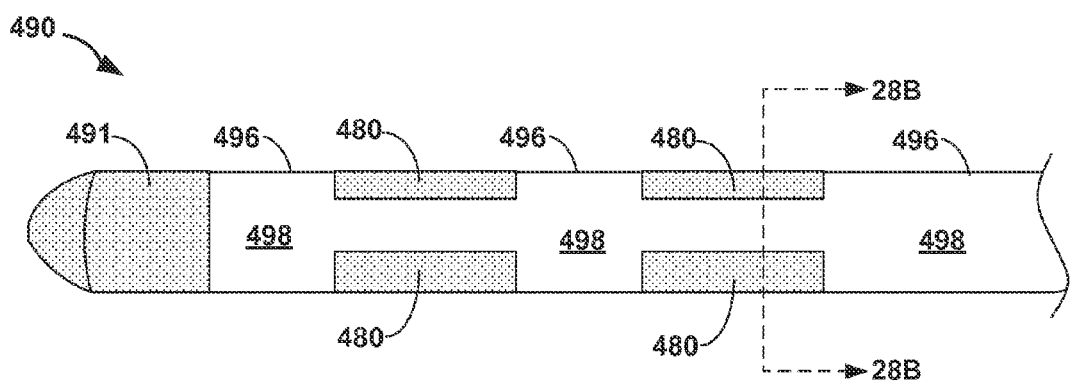

FIGS. 28A-28C illustrate medical lead 490 and its components. In particular, FIG. 28A illustrates electrode segment 480, which is representative of each of electrode segments 480 within medical lead 490. FIG. 28B illustrates a cross-section of medical lead 490. FIG. 28C illustrates a side view of medical lead 490. Electrode segment 480 includes protrusion 484, which is configured to extend into lead body 498. As discussed in greater detail below, protrusion 484 includes concave features that secure the electrode segment 480 to lead body 498.

As shown in FIG. 28A, electrode segment 480 has a T-shaped profiled including a top portion forming exposed outer surface 482 and an inner portion forming protrusion 484. Electrode segment 480 is formed from a folded metal element that forms both exposed outer surface 482 and protrusion 484. Exposed outer surface 482 is formed by two portions of the folded metal element and is bisected by the folds of the folded metal element forming electrode segment 480. The concave features of protrusion 484 include through-hole 485. Through-hole 485 extends in a circumferential direction through protrusion 484 relative to lead body 498 within medical lead 490.

Electrode segment 480 is electrically connected to exposed distal end 489 of insulated conductor 488. Distal end 489 of insulated conductor 488 is pinched within protrusion 484 such that distal end 489 of insulated conductor 488 is in electrical contact with electrode segment 480. Other techniques may be used to further secure distal end 489 of insulated conductor 488 within the inner tubular portion of protrusion 484 such as soldering, welding, brazing, compression fit or other technique.

As shown in FIG. 28C, medical lead 490 includes elongated lead body 498 as well as two sets of electrode segments 480 and a tip electrode 491. Each electrode segment 480 is a separate unitary component. Each set of electrode segments 480 is in a circular arrangement at a common longitudinal position along lead body 498. Medical lead 490 further includes a plurality of conductors 488 (not shown in FIG. 28C) extending within the lead body, each of the conductors being in electrical contact with one of electrode segments 480 or tip electrode 491 and extending to a proximal end of lead body 498. In some examples, medical lead 490 may include a connector at the proximal end of medical lead 490 to electrically connect the connector to electrode segments 480 and tip electrode 491.

As shown in FIG. 28B, the exposed outer surface of each electrode segment 480 is substantially congruent with outer surface 496 of lead body 498. Further, the protrusions 484 (FIG. 28A) provide concave features that secure electrode segment 480 to lead body 498 such that separating one of electrode segments 480 from lead body 498 would require deformation of lead body 498 or the electrode segment 480. Manufacturing of medical lead 490 may include overmolding lead body 498 over electrode segments 480 and insulated conductors 488, e.g., as described with respect to any of medical leads 200, 220 and 400. In some examples, lead body 498 and medical lead 490 may have a substantially circular cross-sectional shape, although other cross-sectional shapes may also be used.

In the example of medical lead 490, medical lead 490 includes two sets of electrode segments 480, each set within a circular arrangement as well as one tip electrode segment 411. Each circular arrangement of electrode segments 490 includes three equally spaced electrode segments 490. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

Figure 29A:
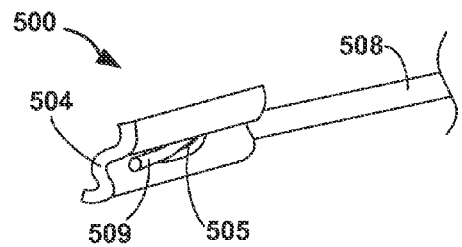
Figure 29B:
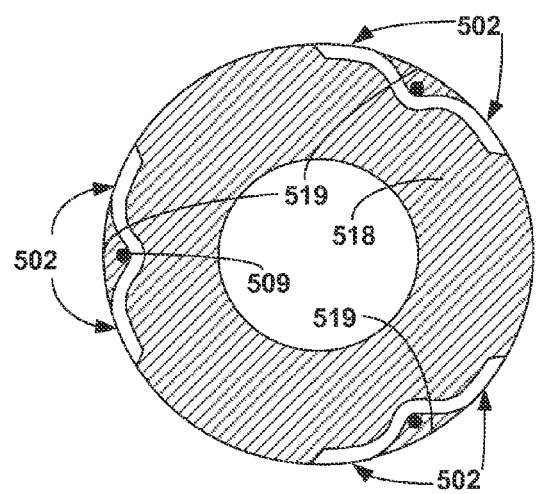
Figure 29C:
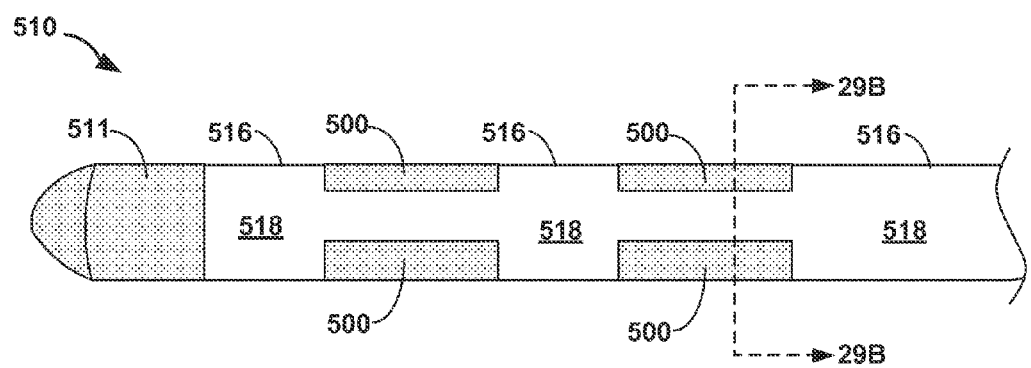

FIGS. 29A-29C illustrate medical lead 510 and its components. More specifically, FIG. 29A illustrates electrode segment 500, which is representative of each of electrode segments 500 within medical lead 510, whereas FIG. 29B illustrates a cross-section of medical lead 510, and FIG. 29C illustrates a side view of medical lead 510. Electrode segment 500 includes protrusion 504, which is configured to extend into lead body 518. As discussed in greater detail below, protrusion 504 includes concave features that secure the electrode segment 500 to lead body 518.

As shown in FIG. 29B, electrode segment 500 has a waved profile in which the exposed outer surface 502 of the electrode segment includes two portions separated by a portion 519 of lead body 518. Electrode segment 500 includes through-hole 505, which extends in a radial direction through a portion of the electrode segment that is adjacent portion 519 of lead body 518.

Electrode segment 500 is electrically connected to exposed distal end 509 of insulated conductor 508. Distal end 509 of insulated conductor 508 extends through through-hole 505 of protrusion 464 such that distal end 509 of insulated conductor 508 is in electrical contact with electrode segment 500. Many techniques may be used to secure distal end 509 of insulated conductor 508 to protrusion 504 such as mechanical pinching, soldering, welding, brazing, compression fit or other technique.

As shown in FIG. 29C, medical lead 510 includes elongated lead body 518 as well as two sets of electrode segments 500 and a tip electrode 511. Each electrode segment 500 is a separate unitary component. Each set of electrode segments 500 is in a circular arrangement at a common longitudinal position along lead body 518. Medical lead 510 further includes a plurality of conductors 508 (not shown in FIG. 29C) extending within the lead body, each of the conductors being in electrical contact with one of electrode segments 500 or tip electrode 511 and extending to a proximal end of lead body 518. In some examples, medical lead 510 may include a connector at the proximal end of medical lead 510 to electrically connect the connector to electrode segments 500 and tip electrode 511.

As shown in FIG. 29B, the exposed outer surface of each electrode segment 500 is substantially congruent with outer surface 516 of lead body 518. Further, the protrusions 504 (FIG. 29A) provide concave features that secure electrode segment 500 to lead body 518 such that separating one of electrode segments 500 from lead body 518 would require deformation of lead body 518 or the electrode segment 500. Manufacturing of medical lead 510 may include overmolding lead body 518 over electrode segments 500 and insulated conductors 508, e.g., as described with respect to any of medical leads 200, 220 and 400. In some examples, lead body 518 and medical lead 510 may have a substantially circular cross-sectional shape, although other cross-sectional shapes may also be used.

In the example of medical lead 510, medical lead 510 includes two sets of electrode segments 500, each set within a circular arrangement as well as one tip electrode segment 411. Each circular arrangement of electrode segments 510 includes three equally spaced electrode segments 510. In other examples, a different number of electrode segments may be positioned within a circular arrangement at equal or unequal intervals. For example, a set of electrode segments within a circular arrangement may include two, three, four, five, six, seven, eight or even more electrode segments may be positioned in a circular arrangement. The electrode segments within a circular arrangement may be spaced at equal or unequal intervals. In addition, the electrode segments within a circular arrangement may be substantially similar or may provide different shapes, such as different surface areas and/or form different size angular portions within the circular arrangement.

In some examples, any of medical leads 430, 450, 470, 490, 510 may be manufactured using the techniques disclosed herein with respect to medical lead 200, medical lead 220 and/or medical lead 400. For example, any of medical leads 430, 450, 470, 490, 510 may be manufactured by securing a set of two or more electrode segments in a circular arrangement at a common longitudinal position within an elongated mold, each of the electrode segments including an outer surface facing outwardly in the circular arrangement and a protrusion located closer to the center of the circular arrangement than the outer surface. The techniques may further include positioning a plurality of conductors within the elongated mold either prior to, at the same time or after positioning the electrode segments within the mold, each of the conductors being in electrical contact with one of the electrode segments and extending to a proximal end of the elongated mold. The techniques may further include injecting a polymeric material into the mold to form an elongated lead body that covers the conductors and the protrusions of the electrode segments.

The techniques disclosed herein may be modified in a variety of ways within the spirit of this disclosure. For example, securing a set of two or more electrode segments in a circular arrangement at a common longitudinal position within an elongated mold may be accomplished, in different examples, with adhesive/glue or even welding or air vacuum as a method to hold the electrode segments in place without mechanical connection during assembling of the lead. In another example, a dissolvable plastic or sugar material may be used to hold the segments in place inside a removable circular holder during manufacturing of the lead including locating the segments within a mold, to facilitate disconnecting the holder from the electrode segments without need for mechanical cutting or milling operations and its related risks for damage or burrs on the electrode segments.

In different examples, any of medical leads 430, 450, 470, 490, 510 may be included in a system with a stimulation generator configured to deliver electrical stimulation via a selected combination of electrode segments and tip electrodes. In such a system, the proximal end of the medical lead is electrically connected to the stimulation generator, e.g., via a connector or otherwise. In some examples, the stimulation generator may be configured to deliver DBS and any of medical leads 430, 450, 470, 490, 510 may comprise a DBS lead.

Various examples have been described. However, modifications may be made to the described examples within the spirit of the present disclosure. For example, leads used in conjunction with the techniques described herein may include fixation mechanisms, such as tines that actively or passively secure a lead in an implanted position or a helix located at a distal end of the lead that requires rotation of the lead during implantation to secure the helix to a body tissue.

As another example, although described herein as being coupled to IMDs, implantable medical leads of according to the present disclosure may be percutaneously coupled to an external medical device for delivery of electrical stimulation to target locations within the patient.

In one example, as disclosed herein, a method of manufacturing a medical lead comprises removing material from a conductive element to form two or more electrode segments from the conductive element. The conductive element is part of an assembly, the assembly comprising an elongated lead body and the conductive element. The conductive element is located at a distal portion of the lead body. The conductive element substantially encircles a longitudinal axis of the lead body. The assembly also comprises a plurality of insulated conductors extending within the lead body, each of the insulated conductors being in electrical contact with the conductive element and extending to a proximal end of the lead body. Each of the insulated conductors contacts a different circumferential portion of the conductive element before removing material from the conductive element. Each of the insulated conductors contacts a different one of the electrode segments after removing the material from the conductive element to form the electrode segments.

In an example, the assembly further includes a connector located at a proximal portion of the lead body, wherein each of the insulated conductors is in electrical contact with the conductive element and the connector.

In an example, the method further comprises securing the conductive element within an elongated mold, and injecting a polymeric material into the mold to form the elongated lead body.

In an example, the conductive element is configured to facilitate mechanical and electrical separation of different circumferential portions of the conductive element to form two or more electrode segments for the medical lead from the conductive element, and the different circumferential portions of the conductive element include portions configured to be removed alternating with the portions configured to form the electrode segments for the medical lead.

In some examples, the portions configured to be removed and the portions configured to form the electrode segments for the medical lead are substantially congruent with an outer surface of the lead body.

In other examples, the portions configured to be removed and the portions configured to form the electrode segments for the medical lead are substantially congruent with an outer surface of the lead body, and wherein the portions configured to be removed extend outwardly beyond the outer surface of the lead body. In such examples, the method may further comprise holding the portions configured to be removed to secure the conductive element within an elongated mold, and injecting a polymeric material into the mold to form the elongated lead body.

In an example, the method further comprises connecting the medical lead to a stimulation generator configured to deliver deep brain stimulation (DBS) to a patient via the medical lead.

In another example, as disclosed herein, an assembly for a medical lead comprises an elongated lead body, a conductive element located at a distal portion of the lead body, wherein the conductive element substantially encircles a longitudinal axis of the lead body, and a plurality of insulated conductors extending within the lead body, each of the insulated conductors being in electrical contact with the conductive element and extending to a proximal end of the lead body. Each of the insulated conductors contacts a different circumferential portion of the conductive element. The conductive element is configured to facilitate mechanical and electrical separation of different circumferential portions of the conductive element to form two or more electrode segments for the medical lead from the conductive element.

In an example, the different circumferential portions of the conductive element include portions configured to be removed alternating with the portions configured to form the electrode segments for the medical lead.

In an example, the portions configured to be removed and the portions configured to form the electrode segments for the medical lead are substantially congruent with an outer surface of the lead body.

In an example, the portions configured to be removed and the portions configured to form the electrode segments for the medical lead are substantially congruent with an outer surface of the lead body, whereas the portions configured to be removed extend outwardly beyond the outer surface of the lead body.

In an example, the portions configured to be removed facilitated holding the conductive element within a mold during an overmolding process used to form the lead body.

In an example, the portions configured to be removed define widths as measured in a longitudinal direction of the lead body that are substantially less than widths of the portions configured to form the electrode segments for the medical lead as measured in the longitudinal direction.

In an example, the portions configured to be removed are approximately centered relative to the portions configured to form the electrode segments for the medical lead along the longitudinal dimension of the portions configured to form the electrode segments for the medical lead.

In an example, assembly further comprises a frame element that maintains the relative positions of the portions of the conductive element configured to form the electrode segments for the medical lead.

In an example, the conductive element is a first conductive element at a first longitudinal position on the distal portion of the lead body, and the assembly further comprises a second conductive element located at a second longitudinal position on the distal portion of the lead body. The second conductive element substantially encircles the longitudinal axis of the lead body. The assembly further comprises additional insulated conductors extending within the lead body, each of the additional insulated conductors being in electrical contact with the second conductive element and extending to the proximal end of the lead body. Each of the additional insulated conductors contacts a different circumferential portion of the second conductive element. The second conductive element is configured to facilitate mechanical and electrical separation of different circumferential portions of the second conductive element to form two or more additional electrode segments for the medical lead from the second conductive element.

In an example, the conductive element is located at the distal tip of the lead body such that the conductive element is configured to form tip electrode segments for the medical lead following the mechanical and electrical separation of the different circumferential portions of the conductive element.

In an example, the assembly further comprises a ring electrode located at a second longitudinal position on the distal portion of the lead body, wherein the ring electrode substantially encircles the longitudinal axis of the lead body, and an additional insulated conductor extending within the lead body, the additional conductor being in electrical contact with the ring electrode and extending to the proximal end of the lead body.

In an example, the assembly further comprises a connector located at the proximal end of the lead body, wherein each of the insulated conductors are in electrical contact with the conductive element and the connector.

In an example, the lead body has a substantially circular cross-sectional shape. In an example, the medical lead comprises a deep brain stimulation (DBS) lead.

In another example, as disclosed herein, a medical lead comprises an elongated lead body, and set of electrode segments located at a common longitudinal position on the lead body. The set of electrode segments were formed by removing radial portions of a conductive element that substantially encircled a longitudinal axis of the lead body. The medical lead further comprises a plurality of insulated conductors extending within the lead body, each of the insulated conductors being in electrical contact with the conductive element and extending to a proximal end of the lead body prior to removal of the radial portions of the conductive element. Each of the insulated conductors contacts a different electrode segment within the set of electrode segments.

In another example, as disclosed herein, a system comprises a medical lead including an elongated lead body, set of electrode segments located at a common longitudinal position on the lead body, wherein the set of electrode segments were formed by removing radial portions of a conductive element that substantially encircled a longitudinal axis of the lead body, and a plurality of insulated conductors extending within the lead body, each of the insulated conductors being in electrical contact with the conductive element and extending to a proximal end of the lead body prior to removal of the radial portions of the conductive element. Each of the insulated conductors contacts a different electrode segment within the set of electrode segments. The system further comprises a stimulation generator configured to deliver electrical stimulation via a selected combination of the electrode segments of the medical lead once the different circumferential portions of the conductive element are mechanically and electrically separated. A proximal end of the medical lead is configured for coupling the medical lead to the stimulation generator.

In an example, the stimulation generator is configured to deliver deep brain stimulation (DBS) to a patient via the medical lead.

In another example, as disclosed herein, a medical lead comprises an elongated lead body, a set of two or more electrode segments in a circular arrangement at a common longitudinal position along the lead body, and a plurality of conductors extending within the lead body, each of the conductors being in electrical contact with one of the electrode segments and extending to a proximal end of the lead body. Each of the electrode segments includes an exposed outer surface and a protrusion extending into the lead body, wherein the protrusion includes concave features that secure the electrode segment to the lead body.

In an example, the concave features of the protrusion include a through-hole that extends in a circumferential direction through the protrusion within the lead body.

In an example, the concave features of the protrusion include a through-hole that extends in a longitudinal direction through the protrusion within the lead body.

In an example, the medical lead further comprises a connector located at the proximal end of the lead body, wherein each of the conductors is in electrical contact with the connector.

In an example, each of the electrode segments has a waved profile in which the exposed outer surface of the electrode segment includes two portions separated by a portion of the lead body.

In an example, each of the electrode segments includes a through-hole that extends in a radial direction relative to a longitudinal axis of the lead body through a portion of the electrode segment that is adjacent to the portion of the lead body separating the two portions of the exposed outer surface of the electrode segment.

In an example, at least one of the electrode segments is a folded metal element including the exposed outer surface and the protrusion.

In an example, the folded metal element forming the at least one electrode segment provides a T-shaped profile such that the exposed outer surface is formed from the end portions of the folded metal element, whereas the protrusion is formed from a center portion of the folded metal element.

In an example, one of the conductors is pinched within the center protrusion such that the conductor is in electrical contact with the folded metal element.

In an example, at least one of the electrode segments includes a top portion forming the exposed outer surface and an inner tubular portion forming the protrusion extending into the lead body.

In an example, one of the conductors is pinched within the inner tubular portion such that the conductor is in electrical contact with the electrode segment.

In an example, the exposed outer surface of each electrode segment is substantially congruent with an outer surface of the lead body.

In an example, for each of the electrode segments, separating the electrode segment from the lead body would require deformation of the lead body or the electrode segment.

In an example, the lead body is an overmold on the protrusions of the electrode segments.

In an example, each of the electrode segments is a separate unitary component. In an example, the lead body has a substantially circular cross-sectional shape.

In an example, the medical lead comprises a deep brain stimulation (DBS) lead.

In another example, as disclosed herein, a method of manufacturing a medical lead comprises securing a set of two or more electrode segments in a circular arrangement at a common longitudinal position within an elongated mold, each of the electrode segments including an outer surface facing outwardly in the circular arrangement and a protrusion located closer to the center of the circular arrangement than the outer surface, positioning a plurality of conductors within the elongated mold, each of the conductors being in electrical contact with one of the electrode segments and extending to a proximal end of the elongated mold, and injecting a polymeric material into the mold to form an elongated lead body that covers the conductors and the protrusions of the electrode segments. Following the formation of the lead body, the outer surfaces of the electrode segments are exposed and the protrusions of the electrode segments extend into the lead body. Each of the protrusions includes a concave feature that secures the electrode segment to the lead body.

In an example, the method further comprises electrically connecting one of the plurality of conductors to each of the electrode segments before injecting the polymeric material into the mold to form the elongated lead body.

In another example, as disclosed herein, a system comprises a medical lead, the medical lead comprising an elongated lead body, a set of two or more electrode segments in a circular arrangement at a common longitudinal position along the lead body, and a plurality of conductors extending within the lead body, each of the conductors being in electrical contact with one of the electrode segments and extending to a proximal end of the lead body. Each of the electrode segments includes an exposed outer surface and a protrusion extending into the lead body, wherein the protrusion includes concave features that secure the electrode segment to the lead body. The system further comprises a stimulation generator configured to deliver electrical stimulation via a selected combination of the electrode segments of the medical lead. A proximal end of the medical lead is configured for coupling the medical lead to the stimulation generator.

In an example, the stimulation generator is configured to deliver deep brain stimulation (DBS) to a patient via the medical lead.

In another example, as disclosed herein, a method of manufacturing a medical lead comprises coupling each of a set of two or more electrode segments to at least one insulative element, securing the electrode segments and the at least one insulative element within an elongated mold, wherein the at least one insulative element combines with the mold to constrain the electrode segments in a circular arrangement at a common longitudinal position within the mold, and injecting a polymeric material into the mold to form an elongated lead body, wherein, following the formation of the lead body, each of the electrode segments includes an exposed outer surface.

In an example, coupling each of the set of two or more electrode segments to at least one insulative element comprises forming an assembly including the set of two or more electrode segments and the at least one insulative element, and securing the electrode segments and the insulative element within the elongated mold comprises locating the assembly within the mold after forming the assembly.

In an example, the at least one insulative element includes an electrode segment holder forming receptacles configured to receive the electrode segments, and forming the assembly including the set of two or more electrode segments and the at least one insulative element includes positioning protrusions of the electrode segments within the receptacles of the electrode segment holder to position the electrode segments in the circular arrangement.

In an example, forming the assembly including the set of two or more electrode segments and the at least one insulative element comprises holding the electrode segments in the circular arrangement and overmolding the at least one insulative element on the electrode segments held in the circular arrangement.

In an example, coupling each of a set of two or more electrode segments to at least one insulative element comprises securing the electrode segments by assembling the electrode segments and the at least one insulative element into a ring arrangement.

In an example, the at least one insulative element is a unitary component that forms an internal surface of the ring arrangement and extends between the electrode segments.

In an example, the at least one insulative element includes a plurality of insulative elements, each of the plurality of insulative element extending between two adjacent electrode segments of the electrode segments in the ring arrangement.

In an example, the at least one insulative element is a unitary component that extends between the electrode segments and forms a frame surrounding of the ring arrangement.

In an example, the method further comprises, after forming the lead body, removing portions of the frame that extend beyond an outer surface of the lead body.

In an example, the at least one insulative element includes a separate insulative element for each of the electrode segments, coupling each of the set of two or more electrode segments to at least one insulative element comprises forming a separate assembly for each of the electrode segments, the separate assemblies each including one of the electrode segments and one of the insulative elements, and securing the electrode segments and the insulative element within the elongated mold comprises locating each of the separate assemblies within the mold after forming the separate assemblies.

In an example, each of the separate insulative elements includes at least one protrusion that extends beyond an external surface of the electrode segment in its assembly, and locating the each of the separate assemblies within the mold after forming the separate assemblies comprises holding the protrusions of the insulative elements to constrain the electrode segments in the circular arrangement within the mold.

In an example, the method further comprises, after forming the lead body, removing portions of the protrusions of the insulative elements that extend beyond an outer surface of the lead body.

In an example, each of the electrode segments includes an exposed outer surface, and the exposed outer surface of each electrode segment is substantially congruent with an outer surface of the lead body.

In an example, the method further comprises electrically connecting one of a plurality of conductors to each of the electrode segments before injecting the polymeric material into the mold to form the elongated lead body, wherein after injecting the polymeric material into the mold to form the elongated lead body, each of the plurality of conductors extends from one of the electrode segments to a proximal end of the lead body.

In an example, the method further comprises electrically connecting the proximal ends of the plurality of conductors to a connector to electrically connect the connector to the electrode segments.

In another example, as disclosed herein, a medical lead comprises an elongated lead body, and an assembly including a set of two or more electrode segments coupled to at least one insulative element in a circular arrangement within the elongated lead body, wherein each of the electrode segments includes an exposed outer surface.

In an example, the at least one insulative element includes an electrode segment holder forming receptacles configured to receive the electrode segments, and protrusions of the electrode segments are positioned within the receptacles of the electrode segment holder.

In an example, the at least one insulative element is an overmold on the electrode segments.

In an example, the electrode segments and the at least one insulative element form a ring arrangement, and the at least one insulative element is a unitary component that forms an internal surface of the ring arrangement and extends between the electrode segments.

In an example, the electrode segments and the at least one insulative element form a ring arrangement, and the at least one insulative element includes a plurality of insulative elements, each of the plurality of insulative element extending between two adjacent electrode segments of the electrode segments in the ring arrangement.

In an example, each of the electrode segments includes an exposed outer surface, and the exposed outer surface of each electrode segment is substantially congruent with an outer surface of the lead body.

In an example, the medical lead further comprises a plurality of conductors, wherein each of the plurality of conductors extends from one of the electrode segments to a proximal end of the lead body.

In an example, the medical lead further comprises a connector on a proximal end of the lead body, wherein the plurality of conductors connect the connector to the electrode segments.

In an example, the lead body has a substantially circular cross-sectional shape.

In an example, the medical lead comprises a deep brain stimulation (DBS) lead.

In another example, as disclosed herein, a system comprises a medical lead, the medical lead comprising an elongated lead body, and an assembly including a set of two or more electrode segments coupled to at least one insulative element in a circular arrangement within the elongated lead body. Each of the electrode segments includes an exposed outer surface. The system further comprises a stimulation generator configured to deliver electrical stimulation via a selected combination of the electrode segments of the medical lead. A proximal end of the medical lead is configured for coupling the medical lead to the stimulation generator.

In an example, the stimulation generator is configured to deliver deep brain stimulation (DBS) to a patient via the medical lead.

What is claimed is:

1. A method of manufacturing a medical lead, the method comprising:
   removing material from a conductive element to mechanically separate a plurality of circumferential portions of the conductive element from each other to form two or more electrode segments from the conductive element,
   wherein the conductive element is part of an assembly, the assembly comprising:
   an elongated lead body,
   the conductive element, wherein the conductive element is located at a distal portion of the lead body, wherein the conductive element substantially encircles a longitudinal axis of the lead body, wherein the plurality of circumferential portions are configured to form the electrode segments of the medical lead, and wherein at least one portion of the conductive element is configured to be removed, the at least one portion being different from the circumferential portions and extending outward beyond an outer surface of the circumferential portions until removed, and
   a plurality of insulated conductors extending within the lead body, each of the insulated conductors being in electrical contact with the conductive element and extending to a proximal end of the lead body,
   wherein each of the insulated conductors is electrically coupled to a different one of the plurality of circumferential portions of the conductive element before removing material from the conductive element, and wherein each of the insulated conductors contacts a different one of the electrode segments after removing the material from the conductive element to form the electrode segments.

2. The method of claim 1, wherein the assembly further includes a connector located at a proximal portion of the lead body, wherein each of the insulated conductors is in electrical contact with the conductive element and the connector.

3. The method of claim 1, further comprising:
securing the conductive element within an elongated mold; and
injecting a polymeric material into the mold to form the elongated lead body.

4. The method of claim 1,
wherein the at least one portion configured to be removed alternates with the portions configured to form the electrode segments for the medical lead.

5. The method of claim 1, wherein the at least one portion configured to be removed forms a frame element configured to maintain position of the portions configured to form the electrode segments relative to each other.

6. The method of claim 1, further comprising connecting the medical lead to a stimulation generator configured to deliver deep brain stimulation (DBS) to a patient via the medical lead.

7. An assembly for a medical lead comprising:
an elongated lead body;
a conductive element located at a distal portion of the lead body, wherein the conductive element substantially encircles a longitudinal axis of the lead body; and
a plurality of insulated conductors extending within the lead body, each of the insulated conductors being in electrical contact with the conductive element and extending to a proximal end of the lead body,
wherein each of the insulated conductors contacts a different one of a plurality of circumferential portions of the conductive element, and
wherein the conductive element is configured to facilitate mechanical and electrical separation of different circumferential portions of the conductive element to form two or more electrode segments for the medical lead from the conductive element,
wherein the plurality of circumferential portions are configured to form the electrode segments of the medical lead, and wherein at least one portion of the conductive element is configured to be removed, the at least one portion being different from the circumferential portions and extending outward beyond an outer surface of the circumferential portions until removed.

8. The assembly of claim 7, wherein the at least one portion configured to be removed alternates with the portions configured to form the electrode segments for the medical lead.

9. The assembly of claim 7, wherein the at least one portion configured to be removed forms a frame element configured to maintain position of the portions configured to form the electrode segments relative to each other.

10. The assembly of claim 8, wherein the at least one portion configured to be removed defines a width as measured in a longitudinal direction of the lead body that is substantially less than widths of the portions configured to form the electrode segments for the medical lead as measured in the longitudinal direction.

11. The assembly of claim 7, further comprising a connector located at the proximal end of the lead body, wherein each of the insulated conductors are in electrical contact with the conductive element and the connector.

12. A medical lead comprising:
an elongated lead body; and
an assembly including a set of two or more electrode segments coupled to at least one insulative element in a circular arrangement within the elongated lead body,
wherein each of the electrode segments includes a protrusion and an exposed outer surface,
wherein the at least one insulative element includes an electrode segment holder forming receptacles configured to receive protrusions of respective electrode segments of the electrode segments, and
wherein protrusions of the electrode segments are positioned within the respective receptacles of the electrode segment holder.

13. The medical lead of claim 12,
wherein the electrode segments and the at least one insulative element form a ring arrangement, and
wherein the at least one insulative element is a unitary component that forms an internal surface of the ring arrangement and extends between the electrode segments.

14. The medical lead of claim 12,
wherein the electrode segments and the at least one insulative element form a ring arrangement, and
wherein the at least one insulative element includes a plurality of insulative elements, each of the plurality of insulative element extending between two adjacent electrode segments of the electrode segments in the ring arrangement.

15. A method of manufacturing a medical lead, the method comprising: coupling each of a set of two or more electrode segments to at least one insulative element in a circular arrangement;
securing the electrode segments and the at least one insulative element within an elongated mold, wherein the at least one insulative element combines with the mold to constrain the electrode segments in the circular arrangement at a common longitudinal position within the mold; and
injecting a polymeric material into the mold to form an elongated lead body, wherein, following the formation of the lead body, each of the electrode segments includes an exposed outer surface.

16. The method of claim 15,
wherein coupling each of the set of two or more electrode segments to at least one insulative element comprises forming an assembly including the set of two or more electrode segments and the at least one insulative element, and
wherein securing the electrode segments and the insulative element within the elongated mold comprises locating the assembly within the mold after forming the assembly.

17. The method of claim 16, wherein forming the assembly including the set of two or more electrode segments and the at least one insulative element comprises holding the electrode segments in the circular arrangement and over-molding the at least one insulative element on the electrode segments held in the circular arrangement.

18. The method of claim 15,
wherein coupling each of a set of two or more electrode segments to at least one insulative element comprises securing the electrode segments by assembling the electrode segments and the at least one insulative element into a ring arrangement, and wherein the at least one insulative element is a unitary component that forms an internal surface of the ring arrangement and extends between the electrode segments.

19. The method of claim 15, further comprising:
electrically connecting one of a plurality of conductors to each of the electrode segments before injecting the polymeric material into the mold to form the elongated lead body,
wherein after injecting the polymeric material into the mold to form the elongated lead body, each of the plurality of conductors extends from one of the electrode segments to a proximal end of the lead body.

* * * * *